(12) United States Patent
Fernandes et al.

(10) Patent No.: US 8,796,232 B2
(45) Date of Patent: Aug. 5, 2014

(54) METHODS FOR TREATING RESISTANT DISEASES USING TRIAZOLE CONTAINING MACROLIDES

(75) Inventors: Prabhavathi B. Fernandes, Chapel Hill, NC (US); David E. Pereira, Apex, NC (US)

(73) Assignee: Cempra Pharmaceuticals, Inc., Chapel Hill, NC (US)

( * ) Notice: Subject to any disclaimer, the term of this patent is extended or adjusted under 35 U.S.C. 154(b) by 147 days.

(21) Appl. No.: 13/125,555

(22) PCT Filed: Oct. 24, 2009

(86) PCT No.: PCT/US2009/061977
§ 371 (c)(1),
(2), (4) Date: Apr. 21, 2011

(87) PCT Pub. No.: WO2010/048600
PCT Pub. Date: Apr. 29, 2010

(65) Prior Publication Data
US 2011/0201566 A1    Aug. 18, 2011

Related U.S. Application Data

(60) Provisional application No. 61/108,110, filed on Oct. 24, 2008, provisional application No. 61/108,137, filed on Oct. 24, 2008, provisional application No. 61/108,112, filed on Oct. 24, 2008, provisional application No. 61/108,168, filed on Oct. 24, 2008, provisional application No. 61/108,134, filed on Oct. 24, 2008, provisional application No. 61/162,109, filed on Mar. 20, 2009.

(51) Int. Cl.
*A61K 31/70* (2006.01)

(52) U.S. Cl.
CPC ..................... *A61K 31/70* (2013.01)
USPC ........................................... 514/29

(58) Field of Classification Search
USPC ........................................... 514/29
See application file for complete search history.

(56) References Cited

U.S. PATENT DOCUMENTS

| | | |
|---|---|---|
| 4,331,803 A | 5/1982 | Watanabe |
| 4,474,768 A | 10/1984 | Bright |
| 4,742,049 A | 5/1988 | Baker |
| 5,444,051 A | 8/1995 | Agouridas |
| 5,527,780 A | 6/1996 | Agouridas |
| 5,543,400 A | 8/1996 | Agouridas |
| 5,635,485 A | 6/1997 | Agouridas |
| 5,656,607 A | 8/1997 | Agouridas |
| 5,747,467 A | 5/1998 | Agouridas |
| 5,760,233 A | 6/1998 | Agouridas |
| 5,770,579 A | 6/1998 | Agouridas |
| 5,834,428 A | 11/1998 | Drucker |
| 5,985,844 A | 11/1999 | Heck |
| 6,011,142 A | 1/2000 | Bonnet |
| 6,020,521 A | 2/2000 | Randolph |
| 6,028,181 A | 2/2000 | Or |
| 6,096,714 A | 8/2000 | Agouridas |
| 6,121,432 A | 9/2000 | Bonnet |
| 6,395,710 B1 | 5/2002 | Chu |
| 6,407,074 B1 | 6/2002 | Bronk |
| 6,420,535 B1 | 7/2002 | Phan |
| 6,437,106 B1 | 8/2002 | Stoner |
| 6,440,941 B1 | 8/2002 | Denis |
| 6,455,505 B2 | 9/2002 | Agouridas |
| 6,515,116 B2 | 2/2003 | Suh |
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,419,961 B2 | 9/2008 | Napoletano |
| 7,601,695 B2 | 10/2009 | Liang |
| 2002/0028781 A1 | 3/2002 | Agouridas |
| 2003/0176327 A1 | 9/2003 | Cassell |
| 2004/0009930 A1 | 1/2004 | Su et al. |
| 2005/0014706 A1 | 1/2005 | Falzari |
| 2005/0022242 A1 | 1/2005 | Rosetti |
| 2005/0153905 A1 | 7/2005 | Burger |
| 2005/0222427 A1 | 10/2005 | Sharpless |
| 2006/0100164 A1 | 5/2006 | Liang et al. |
| 2006/0264385 A1 | 11/2006 | Wang |
| 2007/0167382 A1 | 7/2007 | Finkelstein |
| 2007/0197518 A1 | 8/2007 | Johnson et al. |
| 2008/0113926 A1 | 5/2008 | Ivezic |
| 2008/0221048 A1 | 9/2008 | Woo |
| 2008/0287376 A1 | 11/2008 | Das |
| 2009/0075916 A1 | 3/2009 | Upadhyay |
| 2009/0156517 A1 | 6/2009 | Zhang |

FOREIGN PATENT DOCUMENTS

| | | |
|---|---|---|
| EP | 0248279 A2 | 12/1987 |
| EP | 0680967 A1 | 11/1995 |
| EP | 1024145 A2 | 8/2000 |
| WO | 9830574 A1 | 7/1998 |

(Continued)

OTHER PUBLICATIONS

European Search Report for EP 09 82 2827, dated Mar. 21, 2012.
Liang C. H. et al., "Synthesis and biological activity of new 5-0-sugar modified ketolide and 2-fluoro-ketolide antiobiotics," Bioorganic & Medicinal Chemistry Letters, Pergamon, Elsevier Science, GB, vol. 15, No. 5, Mar. 1, 2005, pp. 1307-1310.
International Search Report for PCT/US2009/061977, dated Dec. 23, 2009, (3 pages).

(Continued)

*Primary Examiner* — Elli Peselev
(74) *Attorney, Agent, or Firm* — Barnes & Thornburg LLP

(57) ABSTRACT

Triazole-containing macrolide and ketolide antibiotics, therapeutic compositions containing them and methods of use for treating diseases caused by one or more resistant organisms are described.

30 Claims, 7 Drawing Sheets

(56) References Cited

FOREIGN PATENT DOCUMENTS

| | | | |
|---|---|---|---|
| WO | 9856800 | A1 | 12/1998 |
| WO | 9921866 | A1 | 5/1999 |
| WO | 9928311 | A1 | 6/1999 |
| WO | 0012521 | A1 | 3/2000 |
| WO | 0031099 | A1 | 6/2000 |
| WO | 0044761 | A2 | 8/2000 |
| WO | 0062783 | A2 | 10/2000 |
| WO | 0110878 | A1 | 2/2001 |
| WO | 0250092 | A1 | 6/2002 |
| WO | 03004509 | | 1/2003 |
| WO | 03004509 | A2 | 1/2003 |
| WO | 03072141 | A1 | 9/2003 |
| WO | 2004080391 | A2 | 9/2004 |
| WO | 2005105821 | | 11/2005 |
| WO | 2007059307 | A2 | 5/2007 |
| WO | 2009055557 | | 4/2009 |
| WO | WO 2009/055557 | A1 | 4/2009 |

OTHER PUBLICATIONS

Barcia-Macay, M., et al., Pharmacodynamic Evaluation of the Intracellular Activities of Antibiotics against *Staphylococcus aureus* in a Model of THP-1 Macrophages, Antimicrob. Agents Chemother. 50:841-851 (2006).

Bebear, C.M., et al., In vitro activity of trovafloxacin compared to those of five antimicrobials against mycoplasmas including *Mycoplasma hominis* and *Ureaplasma* urealyticum fluoroquinolone-resistant isolates that have been genetically characterized, Antimicrob Agents Chemother 44:2557-2560 (2000).

Duffy, L., et al., Fluoroquinolone resistance in *Ureaplasma parvum* in the United States, J Clin Microbiol 44:1590-1591(2006).

Jensen, J.S., et al., Azithromycin Treatment Failure in *Mycoplasma genitalium*—Positive Patients with Nongonococcal Urethritis Is Associated with Induced Macrolide Resistance, Clin Infect Dis 47:1546-53 (2008).

Waites, K.B., et al., Mycoplasmas and ureaplasmas as neonatal pathogens, Clin Microbiol Rev 18:757-89 (2005).

Li, X., et al., Emerging macrolide resistance in *Mycoplasma pneumoniae* in children: detection and characterization of resistant isolates, Pediatr Infect Dis J, 28:693-696 (2009).

Liang, Chang-Hsing, et al. "Synthesis and biological activity of new 5-O-sugar modified ketolide and 2-fluoro-ketolide antibiotics." *Bioorganic & medicinal chemistry letters* 15.5 (2005): 1307-1310.

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Romero et al., 'An efficient entry to new sugar modified ketolide antibiotics' Tetrahedron Letters, vol. 46, 2005, pp. 1483-1487.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

Vince, R., Almquist, R. G., Ritter, C. L., and Deluge, S., Antimicrobial Agents and Chemotherapy, vol. 8, No. 4, 1975, 439-443.

Or et al., 'Design, Synthesis, and Antimicrobial Activity of 6-0-Substituted Ketolides Active Against Resistant Respiratory Tract Pathogens', J. Med. Chem., 43:1045-49 (2000).

Champney et al., 'Structure-Activity Relationships for Six Ketolide Antibiotics', Current Microbiology, 42:203-10 (2001).

Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 37:3057-64 (2002).

Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).

Baker, W.R. et al., 'Modification of macrolide antibiotics. Synthesis of 11-deoxy-11-(carboxyamino)-6-0-methylerythromycin A 11,12-(-cyclic esters) via an intramolecular Michael reaction of O-carbamates with an alpha , beta-unsaturated ketone,' J. Org. Chem., 53:2340-2345, 1988.

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

Phan, L.T. et al., 'Synthesis of 2-Fluoro-6-O-propargy1-11,12-carbamate Ketolides. A Novel Class of Antibiotics,' Org. Ltrs., 2:2951-2954 (2000).

Plata et al., "The synthesis of ketolide antibiotic ABT-773 (cethromycin)," Tetrahedron, vol. 60, 2004, pp. 10171-10180.

Ma et al., Curr. Med. Chem., "Anti-Infective Agents," vol. 1, 2002, pp. 15-34.

Holzer, G., et al., "Ka1,2 and KB1,3 X-Ray Emission Lines of the 3d Transition Metals", Dec. 1997, Physical Review, vol. 56, No. 6, pp: 4554-4568.

Berge, Stephen M., et al., "Pharmaceutical Salts", 1977, Journal of Pharmaceutical Sciences, vol. 66, No. 1, pp. 1-19.

Bermudez, Luiz E., et al., "Telithromycin is Active Against Mycobacterium Avium in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.

Bermudez, Luiz E., et al., "EDP-420, a Bicyclolide (Bridged Bicyclic Macrolide), Is Active Against Mcyobacterium Avium", 2007, Antimicrobal Agents and Chemotherapy, vol. 51, No. 5, pp. 1666-1670.

Cynamon, M. H., et al., "Activity of ABT-773 Against Mycobacterium Avium Complex in the Beige Mouse Model", 2000, Antimicrobal Agents and Chemotherapy, vol. 44, No. 10, pp. 2895-2896.

Patel, Ramesh N., "Stereoselective Biocatalysis", 2000, Bristol-Myers Squibb Research Institute; pp. 775-797.

Vennerstrom, Jonathan L., et al., "Identification of an Antimalarial Synthetic Trioxolane Drug Development Candidate", 2004, Letters to Nature, vol. 430, pp. 900-904.

Zuckerman, "Macrolides and ketolides: azithromycin, clarithromycin, telithromycin", Infectious Disease Clinics of North America, vol. 18, (2004), pp. 621-649.

Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.

Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.

Lee, Adrian, et al., "A standard mouse model of Helicobacter pylori infection: introducing the Sydney Strain," 1997, Gastroenterology, vol. 112, pp. 1386-1397.

Drusano, G. L., et al., "Is 60 Days of Ciprofloxacin Adminstration Necessary for Postexposure Prophylaxis for *Bacillus Anthracis*?", 2008, Antimicrobial Agents and Chemotherapy. vol. 52, No. 11, pp. 3973-3979.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Inglesby, Thomas V., et al., "Anthrax as a Biological Weapon, 2002", 2002, Journal of the American Medical Association, vol. 287, No. 17, pp. 2236-2252.

Celebuski, J.E. et al., 'Chemical Modification of Erythromycin: Novel Reaction Observed by Treatment with Metalloporphyrins', vol. 35, No. 23, pp. 3837-3850, 994, Elsevier Science Ltd.

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.

Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.

Physicians' Desk Reference, p. 2905, (2007).

(56) References Cited

OTHER PUBLICATIONS

Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.

LeMaire, Sandrine, et al., "Cellular Accumulation and Pharmacodynamic Evaluation of the Intracellular Activity of CEM-101, a Novel Fluoroketolide, Against *Staphylococcus aureus, Listeria monocytogenes* and *Legionella pneumophila* in Human THP-1 Macrophages", 2009, Antimicrobial Agents and Chemotherapy. vol. 53, No. 9, pp. 3734-3743.

Caira MR, "Crystalline polymorphism of orgainic compounds," Design of Organic Solids, Topics in Current Chemistry, Springer Berlin Heidelberg, 1998, p. 163-208.

Pathak et al., "Enzymatic Protecting Group Techniques in Organic Synthesis," Stereosel, Biocatal., 2000; pp. 775-797.

METHODS FOR TREATING RESISTANT DISEASES USING TRIAZOLE CONTAINING MACROLIDES

CROSS-REFERENCE TO RELATED APPLICATIONS

This application is a U.S. national application under 37 C.F.R. 371(b) of International Application Serial No. PCT/US2009/061977 filed Oct. 24, 2009, which claims priority under 35 USC §119(e) to U.S. Provisional Application Ser. No. 61/108,110, filed on Oct. 24, 2008, U.S. Provisional Application Ser. No. 61/108,112, filed on Oct. 24, 2008, U.S. Provisional Application Ser. No. 61/108,134, filed on Oct. 24, 2008, U.S. Provisional Application Ser. No. 61/108,137, filed on Oct. 24, 2008, U.S. Provisional Application Ser. No. 61/108,168, filed on Oct. 24, 2008, and U.S. Provisional Application Ser. No. 61/162,109, filed on Mar. 20, 2009, the entire disclosure of each of which are incorporated herein by reference.

TECHNICAL FIELD

The invention described herein relates to the treatment of resistant diseases, or more particularly, diseases caused at least in part by one or more resistant organisms. In particular, the invention described herein relates to the treatment of resistant diseases, or more particularly, diseases caused at least in part by one or more resistant organisms with triazole-containing macrolide and ketolide antibiotics.

BACKGROUND AND SUMMARY OF THE INVENTION

Since the discovery of erythromycin A (ERY), macrolide antibiotics (macrolides) have been an important class of molecules for treating a wide variety of bacterial infections. Further, research on macrolides has provided the discovery of several new generations of macrolide antibiotics. One group is the clarithromycin (CLR) class of compounds, where the ring structure was stabilized by the methylation of the C-6 hydroxyl. Another group is the 15-membered ring aza analogs, of which azithromycin (AZI) is a notorious member. Another groups is the 3-desglycosyl-3-oxo analogs, also known as ketolides, of which telithromycin (TEL) and cethromycin (CTH) are notorious members. However, as has been true for other antibiotic classes of molecules, such as the penecillins, cephalosporins, quinolones, vancomycin, and others, resistant organisms have emerged throughout the world. Macrolide resistance, which is now predominant in some countries such as Japan and Korea, has been blamed on the overuse of AZI and CLR during the past 15 years. It has also been observed that macrolide resistance also usually occurs together with penicillin G resistance (though genetically unlinked). For example, though all strains of group A streptococci are still β-lactam susceptible, macrolide resistance has occurred, especially in Asia and in southern, central and eastern Europe. Infections caused by drug-resistant group A streptococci are encountered worldwide and sometimes life-threatening infections caused by these organisms are encountered. Further, *Streptococcus pyogenes* strains, although retaining their β-lactam susceptibility are becoming more macrolide resistant. It is estimated that nearly 40% of *Streptococcus* strains in the US are resistant to both penicillin and macrolide antibiotics.

In fact, it has been suggested that the introduction of TEL into the therapeutic armamentarium was intended to solve the problem of macrolide resistance in streptococci. TEL is effective against penicillin and erythromycin-resistant *S. pneumoniae* and is a non-inducer of Macrolide-Lincosamide-Streptogramin B ($MLS_B$) resistance. However, even with TEL, which is active against many macrolide resistant *S. pyogenes* genotypes, resistant species have and continue to emerge. In particular, ketolide resistant species, namely to TEL, but also possibly cross resistant with CTH, have been reported worldwide, and most recently in *S. pyogenes* from Europe. Further, TEL is not active against erm(B) group A streptococci (which are naturally TEL resistant). Moreover, observed TEL toxicities have limited the clinical utility of this drug. The rapid emergence of resistant strains may not be surprising; when the free AUC/MIC of TEL against macrolide-resistant pneumococci even with low MICs is examined carefully, it is observed that the number was not significantly above 25. Thus, the high probability of resistance developing might be predicted to occur.

In addition, though the pediatric conjugate vaccine has dramatically decreased meningitis and bacteremia caused by most of the usual drug-resistant pneumococcal clones, outbreaks of serious cases of otitis media caused by pan-resistant strains with a serotype (19A) not included in the vaccine have been reported. Thus, the problem of drug-resistant pneumococci causing community-acquired respiratory infection, especially in children, is likely to worsen with the spread of this clone.

Several specific macrolide resistant mechanisms have been reported, including ribosomal methylation-based resistance (erm(A), erm(B)), efflux-based resistance (mef(A), mef(E), mef(I)), and resistance arising from mutation of the rRNA or ribosomal protein, such as 23S and L4 mutations.

Accordingly, a continuing need for new antibiotics and anti-bacterial agents remains. Further, those new agents would desirably have the property of a low potential for resistance development or induction, and a low potential for naturally occurring resistance.

It has been surprisingly discovered herein that triazole-containing macrolides, including ketolides, exhibit high activity in vitro and in vivo against numerous organisms. Moreover, it has been discovered that the triazole-containing macrolides described herein exhibit high activity in vitro and in vivo against numerous resistant organisms, including both macrolide and ketolide resistant organisms.

In one illustrative embodiment, compounds of Formula (I) are described herein

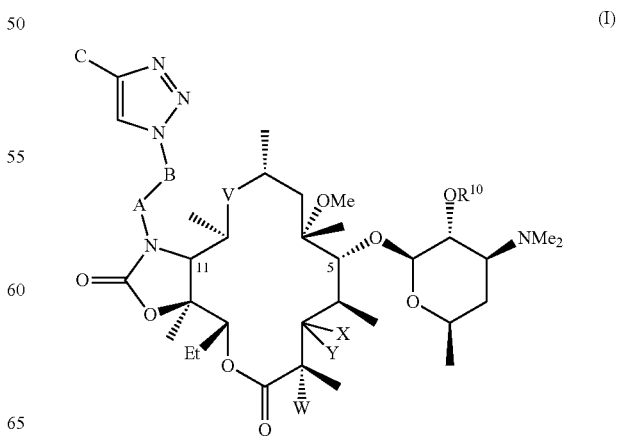

including pharmaceutically acceptable salts, hydrates, solvates, esters, and prodrugs thereof.

In one aspect, $R_{10}$ is hydrogen or acyl. In another aspect, X is H; and Y is $OR_7$; where $R_7$ is a monosaccharide or disaccharide, alkyl, aryl, heteroaryl, acyl, or $C(O)NR_8R_9$, where $R_8$ and $R_9$ are each independently selected from the group consisting of hydrogen, hydroxy, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl.

In another aspect, V is C(O), C(=$NR_{11}$), CH($NR_{12}$, $R_{13}$), or $N(R_{14})CH_2$, where $N(R_{14})$ is attached to the C-10 carbon of the compounds of Formulae 1 and 2; wherein $R_{11}$ is hydroxy or alkoxy, $R_{12}$ and $R_{13}$ are each independently selected from the group consisting of hydrogen, hydroxy, akyl, aralkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl.

In another aspect, W is H, F, Cl, Br, I, or OH.

In another aspect, A is $CH_2$, C(O), C(O)O, C(O)NH, $S(O)_2$, $S(O)_2NH$, $C(O)NHS(O)_2$. In another aspect, B is $(CH_2)_n$ where n is an integer ranging from 0-10, or B is an unsaturated carbon chain of 2-10 carbons. In another aspect, C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureido, or carbamoyl.

In another embodiment, compositions including a therapeutically effective amount of one or more compounds of formula (I), or the various subgenera thereof are described herein. The pharmaceutical compositions may include additional pharmaceutically acceptable carriers, diluents, and/or excipients.

In another embodiment, methods are described herein for treating diseases arising from pathogenic organism populations. The methods include the step of administering a therapeutically effective amount of one or more compounds of formula (I), or the various subgenera thereof are described herein, to a patient in need of relief or suffering from a disease caused by a pathogenic organism.

In another embodiment, uses are described herein for the manufacture of medicaments. The medicaments include a therapeutically effective amount of one or more compounds of formula (I), or the various subgenera thereof are described herein, or one or more compositions thereof described herein. The medicaments are suitable for treating diseases arising from pathogenic organism populations.

DETAILED DESCRIPTION

Figure 1:
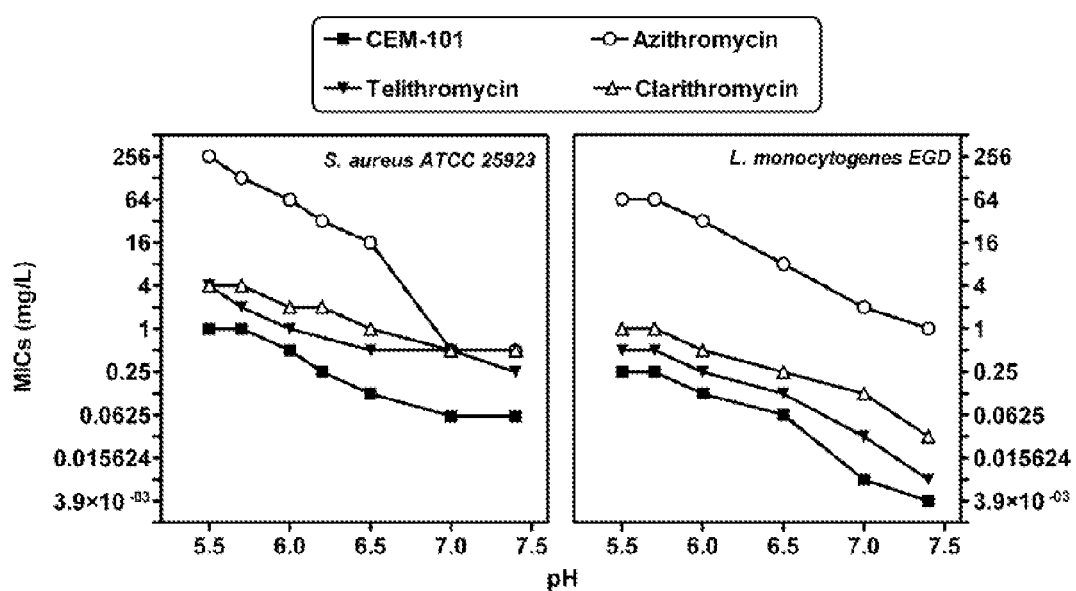
FIG. 1. Comparative susceptibilities of *S. aureus* ATCC 25923 and *L. monocytogenes* EGD to CEM-101, TEL, AZI, and CLR, based on MIC determinations in pH-adjusted broth.

The compounds, compositions, methods, and medicaments described herein including triazole-containing macrolides and ketolides are useful in treating various diseases caused by pathogenic organism populations. Such pathogenic organisms are well known to cause a variety of diseases and disease states. It is appreciated that in some cases the disease or disease state may be characterizable as a symptom of some other underlying disease. In such cases, it is to be understood that such symptom or symptoms are a disease treatable using the compounds, compositions, methods, and medicaments described herein.

In one embodiment, the compounds, compositions, methods, and medicaments described herein are useful for treating respiratory tract infections (RTIs), including community acquired RTIs, such as those arising from or complicated by susceptible bacterial pathogens and/or $MLS_B$ resistant pathogens.

In another embodiment, the compounds, compositions, methods, and medicaments described herein are useful for treating diseases caused by *H. influenzae*, such as lower respiratory tract infections, bacteremia, pneumonia, otitis media, conjunctivitis, sinusitis and acute bacterial meningitis, such as may occur in infants and young children, and caused more specifically by *H. influenzae* type b (Hib). In another embodiment, the diseases include cellulitis, osteomyelitis, epiglottitis, and joint infections.

In another embodiment, the compounds, compositions, methods, and medicaments described herein are useful for treating diseases caused by or complicated by *Mycoplasma*, including *M. pneumoniae, M. hominis, M. genitalium*, and the like. Both *Mycoplasma*, including *M. pneumoniae, M. hominis, M. genitalium*, and *M. fermentans*, and *Ureaplasma*, including *U. parvum* and *U. urealyticum* can be responsible for infections in the respiratory and urogenital tracts. Illustrative diseases that may be treated using the compounds, compositions, methods, and medicaments described herein, that may be caused by mycoplasma include, but are not limited to, respiratory disorders, including atypical pneumonia, human primary atypical pneumonia (PAP), walking pneumonia, and the like, such as may be caused by *M. pneumoniae*, pelvic inflammatory diseases, such as may be caused by *M. genitalium*, contagious bovine pleuropneumonia (CBPP), such as may be caused by *M. mycoides*, or subspecies of mycoides SC (small-colony type), and the like. Illustrative diseases that may be treated using the compounds, compositions, methods, and medicaments described herein, that may be caused by ureaplasma include, but are not limited to, amniolysis disorders, premature delivery disorders, and the like. *M. pneumoniae* is a very small bacterium in the class Mollicutes, and is known to cause *Mycoplasma pneumonia*, a form of bacterial pneumonia. *M. hominis* is a strain of bacteria present in the vagina, and is believed to be a cause of pelvic inflammatory disease. *M. hominis* is known to frequently colonize the genital tract of sexually active men and women. This bacterium has also been associated with post-abortal and post-partum fever. *M. genitalium* was originally isolated in 1980 from urethral specimens of two male patients with non-gonococcal urethritis. Infection by *M. genitalium* is fairly common and can be transmitted between partners during unprotected sexual intercourse.

In another embodiment, the compositions, methods, and medicaments described herein in a therapeutically amount of one or more compounds described herein, where the therapeutically effective amount is capable of exhibiting bactericidal activity against one or more mycoplasma and/or ureaplasma organisms. In another embodiment, the compounds, compositions, methods, and medicaments described herein are useful for treating diseases caused by or complicated by *Mycoplasma* that are resistant to macrolides, including ketolides. In another embodiment, the compounds, compositions, methods, and medicaments described herein are useful for treating diseases caused by or complicated by *Mycoplasma* that are resistant to TEL and/or CTH. In another embodiment, the compounds, compositions, methods, and medicaments described herein are useful for treating diseases caused by or complicated by *Mycoplasma* that are resistant to CLR. In another embodiment, the compounds, compositions, methods, and medicaments described herein are useful for treating diseases caused by or complicated by *Mycoplasma* that are resistant to doxycycline.

It is appreciated that macrolides reportedly have been the treatments of choice for *M. pneumoniae* respiratory infections of adults and children because they have the advantages of being safe and well tolerated in oral formulations, possess anti-inflammatory properties independent of their antibacterial activities, and activity against other microorganisms that may cause clinically similar illness. These properties have also made macrolides attractive for empiric treatment since most mycoplasmal infections are never confirmed by microbiological testing. However, many macrolides lack activity against *M. fermentans* and *M. hominis*. Moreover, it has been suggested that the likelihood that macrolide resistance will develop naturally in *M. pneumoniae* is plausible since there is only a single rRNA operon in the genome and in vitro selected point mutations in domain V of 23S rRNA reduce their affinity for ribosomes.

For example, recent publications have confirmed the emergence of macrolide resistance in 10-33% of *M. pneumoniae* isolates that may have clinical implications on patient outcome. It has been reported that those isolates typically have mutations in domain V of 23S rRNA and erythromycin MICs of 32→64 µg/ml. A recent report from Shanghai, China described 39/50 (78%) of *M. pneumoniae* were macrolide-resistant. The US Centers for Disease Control and Prevention described 3 of 11 cases (27%) of *M. pneumoniae* infections from a recent outbreak that were macrolide-resistant and had a 23S rRNA mutation. In addition, it has been reported that two pediatric patients in Birmingham, Ala. with macrolide-resistant *M. pneumoniae* infections of the lower respiratory tract did not respond initially to treatment with AZI and required several days of hospitalization (Xiao et al., Emerging macrolide resistance in *Mycoplasma pneumoniae* in children: detection and characterization of resistant isolates. Pediatr Infect Dis J In Press (2009)). Fluoroquinolone resistance has been described in genital mycoplasmas (Bebear et al., In vitro activity of trovafloxacin compared to those of five antimicrobials against mycoplasmas including *Mycoplasma hominis* and *Ureaplasma urealyticum* fluoroquinolone-resistant isolates that have been genetically characterized. Antimicrob Agents Chemother 44:2557-60 (2000); Duffy et al., Fluoroquinolone resistance in *Ureaplasma parvum* in the United States. J Clin Microbiol 44:1590-1 (2006)) and tetracycline resistance may now exceed 40% in some populations (Waites et al., *Mycoplasmas* and *ureaplasmas* as neonatal pathogens. Clin Microbiol Rev 18:757-89 (2005)). AZI resistance associated with clinical treatment failure has also been documented in *M. genitalium* (Jensen et al., AZI treatment failure in *Mycoplasma* genitalium-positive patients with non-gonococcal urethritis is associated with induced macrolide resistance. Clin Infect Dis 47:1546-53 (2008)). Despite these challenges, it has been discovered that the triazole-containing macrolides and ketolides described herein are useful in treating diseases caused at least in part by *Mycoplasmas* and/or *Ureaplasmas*, such as urethritis and other infections of the urethra and urogenital tract, including *Mycoplasmas* and/or *Ureaplasmas* resistant to other anti-bacterial agents, macrolides, and ketolides, such as TEL and CTH.

In another embodiment, the compounds, compositions, methods, and medicaments described herein are useful for treating diseases caused by or complicated by *Legionella* sp., such as *L. pneumophila*, and the like. *L. pneumophila* is known to cause legionellosis, also known as Legionnaires' disease.

In another embodiment, the compounds, compositions, methods, and medicaments described herein are useful for treating diseases caused by or complicated by In another embodiment, the compounds, compositions, methods, and medicaments described herein are useful for treating diseases caused by or complicated by *staphylococcus* and/or streptococci organisms, such as skin and skin structure infections (SSSIs). In one variation, the SSSI is a complicated SSSI. In another variation, the SSSI is an uncomplicated SSSI. Illustrative diseases caused by or complicated by *S. aureus* include, but are not limited to, minor skin infections, such as pimples, impetigo, boils, cellulitis, folliculitis, furuncles, carbuncles, scalded skin syndrome and abscesses, and more serious or even life-threatening diseases such as pneumonia, meningitis, osteomyelitis, endocarditis, toxic shock syndrome (TSS), and septicemia.

In another embodiment, the compounds, compositions, methods, and medicaments described herein are useful for treating diseases caused by or complicated by gonococci. Symptoms of infection with *N. gonorrhoeae* differ depending on the site of infection. Illustrative diseases caused by or complicated by gonococci include both gonococcal and non-gonococcal urethritis, which can result in a purulent (or pus-like) discharge from the genitals, inflammation, redness, swelling, dysuria, and/or a burning sensation during urination. Infection of the genitals in females with *N. gonorrhoeae* can result in pelvic inflammatory disease, and if left untreated, may result in infertility. Pelvic inflammatory disease may result if untreated *N. gonorrhoeae* travels into the pelvic peritoneum (via the cervix, endometrium and fallopian tubes).

In another embodiment, the compounds, compositions, methods, and medicaments described herein are useful for treating diseases caused by or complicated by one or more Neisseria, such as *N. meningitides*, including organisms that are resistant nalidixic acid. It is appreciated herein that resistance to nalidixic acid may correlate to resistance to fluoroquinolones. Accordingly, in another embodiment, the compounds, compositions, methods, and medicaments described herein are useful for treating diseases caused by or complicated by one or more Neisseria, such as *N. meningitides*, that are resistant to fluoroquinolones, such as trimethoprim/sulfamethoxazole. *N. meningitides* infections may occur in the nasopharynx.

*N. gonorrhoeae* can also cause conjunctivitis, pharyngitis, proctitis or urethritis, prostatitis and orchitis when present in other tissues. For example, conjunctivitis is reportedly common in neonates; accordingly silver nitrate or antibiotics are often applied to newborns eyes as a preventive measure against gonorrhoea. Neonatal gonorrheal conjunctivitis is contracted when the infant is exposed to *N. gonorrhoeae* in the birth canal, and can result in corneal scarring or perforation. Disseminated *N. gonorrhoeae* infections can also occur, resulting in endocarditis, meningitis, and/or gonococcal dermatitis-arthritis syndrome. Dermatitis-arthritis syndrome is often accompanied by arthralgia, tenosynovitis, and/or painless non-pruritic dermatitis.

In another embodiment, the compounds, compositions, methods, and medicaments described herein are useful for treating diseases caused by or complicated by Enterococcus spp., including *E. faecalis*. *Enterococcus* spp., cause or contribute to diseases such as urinary tract infections, bacteremia, bacterial endocarditis, diverticulitis, and meningitis.

In another embodiment, the compounds, compositions, methods, and medicaments described herein are useful for treating diseases caused by or complicated by ureaplasma sp, such as *U. parvum, U. urealyticum*, and the like. *U. urealyticum* has been reportedly associated with a number of diseases in humans, including non-specific urethritis (NSU), infertility, chorioamnionitis, stillbirth, premature birth, and, in the perinatal period, pneumonia, bronchopulmonary dysplasia, and meningitis.

In another embodiment, the compounds, compositions, methods, and medicaments described herein are useful for treating diseases caused by or complicated by *Chlamydia* sp., including *C. trachomatis, C. pneumoniae*, and the like. Like gonococci, *Chlamydia* causes different diseases depending upon the organ or tissue infected. *Chlamydia* sp. reportedly cause genital disease. For example, *C. pneumoniae* is well recognized as an important pathogen of respiratory tract infections worldwide, being responsible for almost 10% of cases of community-acquired pneumonia. Chlamydial infection of the neck of the womb (cervicitis) is a sexually transmitted illness which is asymptomatic for about 50-70% of women infected with the disease. However, the infection can be passed through vaginal, anal, and/or oral sex. Even when asymptomatic, chlamydial infection that is not detected will progress to pelvic inflammatory disease (PID), in approximately half of affected persons. PID is a generic term for infection of the uterus, fallopian tubes, and/or ovaries. PID can cause scarring inside the reproductive organs, later causing more serious complications, including chronic pelvic pain, difficulty becoming pregnant, ectopic (tubal) pregnancy, and other dangerous complications of pregnancy. In addition, it has been reported that women infected with chlamydia are up to five times more likely to become infected with HIV, if exposed. In men, *Chlamydia* reportedly shows symptoms of infectious urethritis (inflammation of the urethra) in about 50% of cases. If left untreated, it is possible for *Chlamydia* in men to spread to the testicles causing epididymitis, which in rare cases can cause sterility if not treated. *Chlamydia* has also been suggested as a potential cause of prostatitis in men.

*Chlamydia* also reportedly causes eye disease, and in particular conjunctivitis due to chlamydia infection. *Chlamydia* conjunctivitis or trachoma was once the most important cause of blindness worldwide, but its role is reportedly diminished. Newborns can also develop chlamydia eye infection through childbirth via exposure to the organism in the birth canal. *Chlamydia* also reportedly causes rheumatological conditions, such as reactive arthritis, or the the triad of arthritis, conjunctivitis, and urethritis, especially in young men. *Chlamydia* also reportedly causes perinatal infections. It has been reported that as many as half of all infants born to mothers with chlamydia will be born with the disease. *Chlamydia* can affect infants by causing spontaneous abortion; premature birth; conjunctivitis, which may lead to blindness; and pneumonia. *Chlamydia* also reportedly causes other conditions, such as lymphogranuloma venereum, an infection of the lymph nodes and lymphatics, caused by *C. trachomatis*. *Lymphogranuloma venereum* usually is evidenced by genital ulceration and swollen lymph nodes in the groin, but it may also manifest as proctitis (inflammation of the rectum), fever or swollen lymph nodes in other regions of the body.

In another embodiment, the compounds, compositions, methods, and medicaments described herein are useful for treating diseases caused by or complicated by Steptococci sp., such as *S. pneumoniae, S. pyogenes*, alpha-hemolytic streptococci, *Streptococcus* Viridans-group, the beta-hemolytic streptococci of Lancefield groups A and B (also known as "Group A Strep" and "Group B Strep"), and the like. In addition to strep throat, certain *Streptococcus* species are also reportedly responsible for cases of meningitis, bacterial pneumonia, endocarditis, erysipelas, and necrotizing fasciitis (also known as flesh-eating bacterial infections). In the medical setting, the most important groups are the In another embodiment, the compounds, compositions, methods, and medicaments described herein are useful for treating blood borne infectious diseases such as bacteremia, which may be caused by a number of pathogenic organisms.

In another embodiment, the compounds, compositions, methods, and medicaments described herein are useful for treating diseases such as respiratory tract infects (RTIs), including community acquired RTIs, such as community acquired pneumonia (CAP), community acquired bacterial pneumonia (CABP), and nosocomial RTIs, sinusitis, chronic bronchitis, pharyngitis, otitis media, asthma, and the like, skin and skin structure infections (SSSIs), including both complicated and uncomplicated SSSI, and the like, urinary tract infections (UTIs), including uthreitis, gonorrhea, non-GC urethritis, prostatitis, and the like, blood-borne bacterial infections, such as bacteremia, and the like, traveler's diarrhea, and others.

In each of the foregoing embodiments, it is to be understood that the compounds, compositions, methods, and medicaments described herein, may be used in treating diseases arising from various organisms that are resistant to other compounds, including organisms that are resistant to penicillins, cephalosporins, quinolones, vancomycin, and/or macrolides, including ketolides, such as TEL and CTH. Illustratively, described herein are compounds, compositions, methods, and medicaments useful for treating diseases caused by clinically important mycoplasmal and ureaplasmal species of humans, including AZI and TEL-resistant *M. pneumoniae*, doxycycline-resistant *M. hominis*, and doxycycline-resistant *Ureaplasma* spp.

In each of the foregoing embodiments, the methods include the step of administering one or more compounds of formula (I), and/or any of the various subgenera of formula (I) described herein, and/or a pharmaceutically composition of any one or more of the foregoing compounds. The compound(s) and/or composition(s) are administered to a patient suffering from or in need of relief from a disease caused at least in part by one or more of the organisms described herein. In another embodiment, the disease is caused at least in part by one or more of the organisms exhibiting resistance to one or more macrolide antibiotics. In another embodiment, the disease is caused at least in part by one or more of the organisms exhibiting resistance to one or more ketolide antibiotics. In another embodiment, the disease is caused at least in part by one or more organisms selected from MRSA, MRSA 300 (CA), VRSA, Macrolide-Lincosamide-Streptogramin B (MLS$_B$) resistant organism, MDR pneumococcus, *S. pneumoniae* serotype 19A (also known as Multidrug-Resistant Pneumococcal Serogroup 19A), erythromycin resistant *S. pyogenes*, erythromycin resistant staphylococci, or *S. pneumoniae* with at least one erm(B), erm(A), mef(A), mef(E), mef(I), erm(B)+mef(A), L4, or 23S ribosomal protein mutation, or a combination thereof. In another embodiment, the disease is caused at least in part by one or more *S. pyogenes*. In another embodiment, the disease is caused at least in part by one or more *S. pneumoniae*. In another embodiment, the disease is caused at least in part by one or more organisms selected from *S. pyogenes* and a *S. pneumoniae* with any one or more of erm(B), erm(A), mef(A), mef(E), mef(I), erm(B)+mef(A), L4, or 23S ribosomal protein mutation, and combinations thereof. In another embodiment, the disease is caused at least in part by one or more organisms selected from an erythromycin resistant *S. pyogenes*, and a *S. pneumoniae* with at least one erm(B), erm(A), mef(A), mef(E), mef(I), erm(B)+mef(A), L4, or 23S ribosomal protein mutation, and combinations thereof. In another embodiment, the disease is caused at least in part by one or more organisms selected from a *S. pneumoniae* with at least one erm(B), erm(A), mef(A), erm(B)+mef(A), L4, or 23S ribosomal protein mutation, and combinations thereof. In another embodiment, the disease is caused at least in part by one or more organisms resistant to CLR. In another embodiment, the disease is caused at least in part by one or more organisms resistant to AZI. In another embodiment, the disease is caused at least in part by one or more organisms resistant to TEL. In another embodiment, the disease is caused at least in part by one or more organisms resistant to CTH.

In each of the foregoing embodiments, the methods include the step of administering one or more compounds of formula (I), and/or any of the various subgenera of formula (I) described herein, and/or a pharmaceutically composition of any one or more of the foregoing compounds to a patient suffering from or in need of relief from a disease caused at least in part by one or more organisms selected from *Gonococcus*, such as *Neisseria gonorrhoeae Mycoplasma*, such as *M. pneumoniae, M. genitalium, M. fermentans*, and *M. hominis, Ureaplasma*, including *U. parvum* and *U. urealyticum, Moraxella*, including *M. catarrhalis, Enterococcus*, including *E. faecalis, Staphylococcus*, including *S. aureus, S epidermidis*, MSSA, MRSA, MRSA 300, and VRSA, *Streptococcus*, including *S. pneumoniae, l* such as serotype 19A *S. pneumoniae*, erythromycin resistant *S. pyogenes*, coagulase-negative staphylococci, Emerging TEL-Resistant β-Haemolytic Streptococci, *H. haemolyticus*, including beta haemolytic streptococci, *S. mitis*, and viridans group strep, *Chlamydia*, including *C. pneumoniae* and *C. trachomatis, H. influenzae, H. parainfluenzae, Legionella*, such as *L. pneumophila, Listeria*, such as *L. monocytogenes, Neisseria*, such as *N. meningitides, Mycobacterium leprae, Bacillus* spp., *Corynebacterium* spp., *Micrococcus* spp., and *Anaerobic* organisms.

It has been unexpectedly discovered that compounds like CEM-101 show similar activity compared to TEL towards TEL susceptible isolates, but lower MICs towards TEL intermediate and TEL resistant isolates, such as in the Belgian collection of *S. pneumoniae* described herein with confirmed CAP resistant to macrolides and ketolides, such as TEL. The compounds described herein exhibit the widest spectrum and best activity against RTI pathogens among all tested MLSB-ketolide agents, including AZI. CLR, ERY, TEL, clindamycin (CLN), and Synercid® (SYN), and comparable spectrum and activity to levofloxacin (LEV). For example, CEM-101 MIC values were at ≤0.5 and ≤4 µg/ml for *S. pneumoniae, L. pneumophila*, and *H. influenzae*, respectively.

Without being bound by theory, it is believed that the efficacy observable with the compounds described herein may be due at least in part to one or more features of the compounds, including the intracellular accumulation, intracellular activity, distribution to many compartments at high concentration, high activity on resistant organisms, low potential for and low inducible resistance, and bactericidal activity of the compounds described herein. It was surprisingly found herein that the compounds described herein are not PGP substrates or are poor PGP substrates.

The ketolides differ structurally from the macrolides, (1) lacking the 3-O-cladinose, (2) including the presence of 3-keto group, and (3) in the case case of the compounds described herein, including the presence of an aromatic functionality to interact with domain II of the bacterial ribosome. It is believed herein that in addition to the other interactions common to macrolides, ketolides, such as the compounds described herein, have additional interactions with the ribosome, including H-bonding to the 2-fluoro when present, interactions with the 3-oxo group, and interactions with the pendant aromatic group attached to the C-11, C-12 cyclic carbamate. Without being bound by theory, it is believed that these features may contribute to activity against resistance orgs, the low observed inducible resistance, and/or the bactericidal activity of the compounds described herein.

In another embodiment, compounds are described herein that are active against macrolide, including ketolide, resistant organisms, and also have a low potential for resistance development, and/or low inducible resistance rates. Without being bound by theory, it is believed herein that the compounds bind more tightly to the ribosome of the infecting organism. In addition, though again not being bound by theory, it is believed herein that the compounds bind to the ribosome of the infecting organism more tightly and/or in a manner different from other macrolides or even other ketolides. In particular, it is believed herein that the compounds described herein bind to the ribosome with a different orientation. In addition, it is believed herein that the compounds described herein have an additional binding site to the ribosome that other macrolides or ketolides, allowing for tighter binding. In each of the foregoing, it is believed herein that the 1,2,3-triazole is responsible for the differences in binding interactions between the compounds described herein and other macrolides and ketolides.

For example, a common mechanism that leads to macrolide resistance involves Erm-mediated methylation of a key bacterial ribosomal nucleotide (A2058EC) found in domain V of the 23S RNA. This nucleotide was shown to play a major role in the ribosomal binding of macrolide antibiotics through interactions with the macrolide desosamine sugar. Methylation of A2058 effectively interferes with the binding of the desosamine sugar thereby reducing the binding affinity of the macrolide to the bacterial ribosome. A possible explanation for the enhanced activity of the compounds described herein against macrolide-resistant bacteria stems from additional domain II interactions through the pendant aryl-1,2,3-triazolyl side chain. It has been suggested that this additional interaction helps compensate for alterations at the domain V binding site in resistant bacteria. In addition, though without being bound by theory, and unlike other macrolides or ketolides, it is believed that the compounds described herein are able to bind both domain II and V of ribosomal RNA, and able to maintain in vitro activity against macrolide-resistant *M. pneumoniae* that have altered binding sites in domain V due to the A2063G mutation. For example, one such compound, CEM-101 has lower MICs than TEL for the human mycoplasmas. CEM-101 maintained in vitro activity against two AZI resistant *M. pneumoniae* with MICs of 0.5 µg/ml while TEL MICs of 4 µg/mL exceeded the breakpoint of 1 µg/mL used to designate susceptibility for other bacterial species. The difference between the $MIC_{50}$ for the *M. pneumoniae* group overall and the MICs for the two resistant isolates was the same at 14 two-fold dilutions for each drug. Therefore, the modest lowering of the CEM-101 in vitro MIC may be more profound in vivo when treating diseases caused at least in part by mycoplasmas. It was also surprisingly found that both CEM-101 and CEM-103 (3-cladinose of 101) show considerable binding to the ribosome erm-dimethylated at A2058. CEM-103 is the macrolide analog of CEM-101 having a 3-cladinose rather than a 3-oxo group, and therefore supports the theory that the 1,2,3-triazole is responsible for the differences in binding interactions between the compounds described herein and other macrolides and ketolides.

In addition, the compounds described herein have low potential for and/or low inducible resistance. In single step mutational resistance and also in multi-step passage to resistance, no growth of mutants was observed when the strains were exposed to 4×, 8× and 16× CEM-101 MIC with any of the 4 strains tested. The mutation rates by organism were: *E. faecium* at $<4.0 \times 10^{-9}$, *S. aureus* at $<6.0 \times 10^{-9}$ and *S. pneumoniae* at $<6.4 \times 10^{-8}$ to $<1.4 \times 10^{-9}$. Among 18 isolates tested for resistance selection during passaging in sub-inhibitory concentrations of antimicrobial agents, no significant variation (more than±one $log_2$ dilution) of the MIC values of CEM-101 was observed with eight strains (44.4%), including one *S. aureus*, three enterococci, three *S. pneumoniae*, and one β-hemolytic *Streptococcus*. The remaining 10 strains exhibited modest increases of CEM-101 MICs of four-fold (seven strains) to eight-fold (three strains), with no reversion or only a two-fold decrease in the MIC value after three consecutive daily passages in antimicrobial free media. Resistance selection during passaging in sub-inhibitory concentrations was less overall for CEM-101 when compared to other agents evaluated.

In another embodiment, compounds are described herein that are active intracellularly. It has also been discovered herein that the intracellular accumulation and intracellular activity of triazole-containing macrolides was not affected by Pgp or Multidrug Resistant Protein (MRP) inhibitors. Accordingly, it is believed that the compounds described herein are not substrates or are poor substrates of P-glycoprotein (plasma or permeability gycoprotein, Pgp). It is appreciated that Pgp is an efflux mechanism that may lead to resistance by some organisms against certain antibiotics, such as has been reported for AZI and ERY in macrophages in which both antibiotics are substrates of the P-glycoprotein. Accordingly, it has been surprisingly found that the compounds described herein accumulate intracellulary. In addition to the intracellular accumulation, it has been surprisingly discovered that the triazole-containing macrolide and ketolide compounds described herein have high intracellular activity. It has also been surprising found herein that the compounds described herein have lower protein binding than is typical for macrolides at lower pH, such as the pH found in bacterial infections, including but not limited to abscesses. It is appreciated that the lack of intracellular activity typically observed with anti-bacterial agents, including other macrolides and ketolides, may be due to high protein binding, and/or to the relatively lower pH of the intracellular compartments, such as is present in abscesses.

However, even when not removed by active efflux, the concentration of other anti-bacterial agents, including other macrolides and ketolides, in macrophages may not be efficacious in treating disease because of the low pH of the lysozomal compartment. For example, the acidic environment prevailing in the phagolysosomes (where *S. aureus* sojourns during its intracellular stage) may impair the activity of antibiotics, such as the AZI, CLR and TEL. It has been unexpectedly found that the compounds described herein retain their anti-bacterial activity at low pH. It is appreciated that the intracellular activity of the compounds described herein may be an important determinant for fast and complete eradication and, probably also, for prevention of resistance in the target organism.

Lack of effective antimicrobial therapy results in intracellular survival of bacteria, which remains a major cause of bacterial spreading, life-threatening therapeutic failures, and establishment of chronic, relapsing infections. These situations are observed during the course of infections caused by many organism, including meningitis from *L. monocytogenes*, invasion of lung macrophages from *L. pneumophila*, and endocarditis, osteomyelitis, and skin and skin structure infections from *S. aureus*.

While it has been reported that intracellular accumulation of an antibiotic is indicative of efficient activity against bacteria, pharmacodynamic evaluation of a large series of commonly used antibiotics has revealed that other parameters such as intracellular bioavailability and modulation of activity in the infected compartment are also important. The observations described herein confirm and extend previous observations made with macrolides in this context due to the surprising differential behavior exhibited by the triazole-containing macrolides described herein, compared to known macrolide and ketolides, such as TEL, AZI, and CLR.

It is surprisingly found that triazole-containing macrolides accumulate to a considerably larger extent than the comparators, including AZI, and consistently expresses greater potency (decreased values of $E_{50}$ and $C_s$) while showing similar maximal efficacy ($E_{max}$) to comparators. Without being bound by theory, it is believed that this indicates that the improvements resulting from the structural modifications introduced in CEM-101 relate to modulation of pharmacokinetic properties and intrinsic activity (including its reduced susceptibility to physico-chemical conditions prevailing in the infected compartment) rather than to a change in its mode of action. Thus, triazole-containing macrolides exhibit the essentially bacteriostatic character of macrolides, but express it better in the intracellular milieu and at considerably lower extracellular concentrations than the comparators.

Without being bound by theory, it is believed that the cellular accumulation of triazole-containing macrolides, such as CEM-101, results from the general mechanism of proton trapping of weak organic bases envisaged for all macrolides as accumulation is almost completely suppressed, in parallel with AZI, by exposure to acid pH or to the proton ionophore monensin. Based on the general model of diffusion/segregation of weak bases in acidic membrane-bound compartments, accumulation is determined by the number of ionizable groups and the ratios between the membrane permeability coefficients of the unionized and ionized forms of the drug. While CEM-101 has two ionizable functions, the pKa of the aminophenyltriazole is calculated to be less than 4, suggesting that the molecule is largely monocationic (similar to CLR and TEL) at neutral and even at lysosomal pH (~5). In contrast, AZI has two ionizable functions with $pK_a s > 6$ and is therefore dicationic intracellularly. CEM-101, however, possesses a fluoro substituent in position 2, which should make it more lipophilic than CLR or TEL. Without being bound by theory, it is believed that the ratio of the permeability constants of the unionized and ionized forms of CEM-101 in comparison with LR or TEL may be as important as the number of ionizable functions to determine the level of cellular accumulation of weak organic bases. Without being bound by theory, it is believed that the greater cellular accumulation of CEM-101 may be partially due to its lack of susceptibility to Pgp-mediated efflux (which is expressed by THP-1 macrophages under our culture conditions) in contrast to AZI.

It has been observed that many known macrolides have a large volume of distribution, which it is believed is related to their ability to accumulate inside eukaryotic cells by diffusion/segregation in acidic compartments, namely lysosomes and related vacuoles. As a consequence, known macrolides had been considered candidates for the treatment of infections localized in these compartments. Thus, it might be assumed that macrolides are suitable for treating infections caused by typical intracellular pathogens such Legionella and Chlamydia, based on a large array of both in vitro and clinical data. However, direct quantitative comparisons between intracellular and extracellular activities using facultative intracellular pathogens, such as S. aureus or L. monocytogenes, suggest that known macrolides express only a minimal fraction of their antibacterial potential intracellularly, especially considering their great intracellular accumulation. This minimized antibacterial potential against organisms replicating in phagolysosomes and related vacuoles is believed to be related to acidic pH which is known to reduce the activity of known macrolides. Another factor is that some organisms, such as L. monocytogenes, may actually replicate in other subcellular compartments. In addition, certain macrolides, such as AZI, are subject to active efflux from macrophages, which further contributes to suboptimal intracellular activity.

In contrast, the cellular accumulation and intracellular activity of the triazole-containing compounds described herein, using models that have been developed for the study of the intracellular pharmacodynamics of antibiotics, is substantially improved over known macrolides, including ketolides. Thus, the compounds described herein maintain the maximal efficacy of their MICs, and show greater potency against intracellular forms of for example, Staphylococcus, Listeria, and Legionella compared to TEL, AZI, and CLR. Without being bound by theory, it is believed that this improved intracellular potency of the triazole-containing compounds described herein results from the combination of the higher intrinsic activity against Staphylococcus, Listeria, and Legionella coupled with the retained activity at low pH, and the ability to distribute to a wide variety of intracellular compartments.

In another embodiment, the triazole-containing macrolide and ketolide compounds have intracellular activity, such as intracellular activity against Staphylococcus, such as S. aureus. Survival of S. aureus within eukaryotic cells is critical for the persistence of infection. It is appreciated that routine susceptibility testing are usually determined against extracellular bacterial only, and therefore may be misleading in their prediction of efficacy against intracellular organisms. In another embodiment, compounds, compositions, methods, and uses are described herein for treating a disease caused at least in part by an intracellular Staphylococcus infection. In another embodiment, the disease caused by the Staphylococcus infection is community acquired MRSA (CA-MRSA), community acquired pneumonia (CA-P), or a skin and skin structure infection (SSSIs). It is further appreciated that S. aureus is considered a virulent strain, and thus treatment with bacteriostatic agents may be ineffective. For example, recurrence may be a problem when treating such strains. It has been unexpectedly discovered herein that the compounds described herein are also bactericidal and therefore useful in treating diseases caused by Staphylococcus, and in particular intracellular Staphylococcus, such as S. aureus in either instance.

In another embodiment, the triazole-containing macrolide and ketolide compounds have intracellular activity, such as intracellular activity against Listeria, such as L. monocytogenes. In another embodiment, the triazole-containing macrolide and ketolide compounds have intracellular activity, such as intracellular activity against Legionella, such as L. pneumophila.

In another embodiment, the triazole-containing macrolide and ketolide compounds have intracellular activity against Mycobacterium, such as M. leprae. In another embodiment, compositions, methods, and medicaments are described herein for treating diseases caused at least in part by M. leprae, including but not limited to Hansen's disease (leprosy). In one aspect, the compositions, methods, and medicaments include a therapeutically effective amount of one or more compounds described herein. In another embodiment, compounds, compositions, methods, and medicaments are described herein for treating diseases caused at least in part by M. leprae that are resistant to CLR. For example, CEM-101 has been found to be 2-4 times more active than other antibiotics of the same class mainly CLR and TEL. It is active against a variety of macrolide resistant pathogenic strains of *S. aureus, S. pyogenes,* and *S. pneumoniae.*

In another embodiment, the compounds, methods, and medicaments described herein include a therapeutically effective amount of one or more compounds described herein, wherein the therapeutically effective amount is an amount effective to exhibit intracellular antibacterial activity.

In another embodiment, compounds are described herein that are bactericidal. In another embodiment, the compounds, methods, and medicaments described herein include a therapeutically effective amount of one or more compounds described herein, wherein the therapeutically effective amount is an amount effective to exhibit bactericidal activity, including in vivo bactericidal activity. It has been reported that macrolides are generally bacteriostatic. Bacteriostatic compounds do not kill the bacteria, but instead for example inhibit growth and reproduction of bacteria without killing them; killing is accomplished by bactericidal agents. It is understood that bacteriostatic agents must work with the immune system to remove the microorganisms from the body. Bacteriostatic antibiotics may limit the growth of bacteria via a number of mechanisms, such as by interfering with bacterial protein production, DNA replication, or other aspects of bacterial cellular metabolism. In contrast, bactericidal antibiotics kill bacteria; bacteriostatic antibiotics only slow their growth or reproduction. Penicillin is a bactericide, as are cephalosporins, all belonging to the group of β-lactam antibiotics. They act in a bactericidal manner by disrupting cell wall precursor leading to lysis. In addition, aminoglycosidic antibiotics are usually considered bactericidal, although they may be bacteriostatic with some organisms. They act by binding irreversibly to 30s ribosomal subunit, reducing translation fidelity leading to inaccurate protein synthesis. In addition, they inhibit protein synthesis due to premature separation of the complex between mRNA and ribosomal proteins. The final result is bacterial cell death. Other bactericidal antibiotics include the fluoroquinolones, nitrofurans, vancomycin, monobactams, co-trimoxazole, and metronidazole.

In another embodiment, the compounds, compositions, methods, and medicaments described herein include a therapeutically effective amount of one or more compounds described herein, wherein the therapeutically effective amount is an amount effective to exhibit bactericidal activity against one or more pneumococcus. It has been reported that resistance by pneumococcus occurs very rapidly. Accordingly, without being bound by theory, it is believed herein that treating such diseases using bacteriostatic agents may be unsuccessful in two respects. First, simply stopping the progression of the disease with a bacteriostatic agent may be insufficient because the immune system may not intervene to assist in curing the disease at a necessary level. For example, some bacterial organisms are not killed by the immune system because they reside in intracellular compartments. Thus, once the treatment course has ended, rapid recurrence of disease may result. Second, because some portion of the bacterial population will likely be eliminated, the remaining population may be selected for resistance development. It is believed herein that an intracellularly active agent, and/or an intracellularly active and bactericidal agent, will be efficacious in treating such diseases. In one illustrative embodiment, compounds described herein that achieve an intracellular concentration of 20× the MIC of the targeted bacteria. It has been reported that most, if not all, macrolide antibiotics, though bactericidal in vitro, are only bacteriostatic in vivo. For example, as described hereinbelow, when the time between the last dose of compound was extended, the bioload reduction levels remained the same for the triazole-containing compounds described herein, indicating a bactericidal response. In contrast, the TEL and CLR dose groups demonstrated bioload increases when the time interval was extended. Thus, those latter two macrolide/ketolide agents demonstrated a more classical bacteriostatic response.

In another embodiment, compounds, compositions, methods, and medicaments are described herein having a long post-antibiotic effect (PAE). In another embodiment, compounds, compositions, methods, and medicaments are described herein that are synergistic with other anti-bacterial agents. In another embodiment, the other anti-bacterial agents are selected from aminoglycoside antibiotics, cephalosporins, and dihydrofolate reductase and dihydropteroate synthetase inhibitors, such as gentamicin (GEN), ceftriaxone (CRO), trimethoprim/sulfamethoxazole (TMP/SMX).

In each of the forgoing embodiments, it is to be understood that the disease treatable by the compounds, compositions, and methods described herein is caused by at least one organism other than one or more of the following: *S. aureus* (ATCC 29213, MSSA, MLS-S), *E. faecum* (ATCC 19434), *K. pneumonia* (13883), *E. coli* (ATCC 25922), *S. typhimurium* (ATCC 14028), *S. pneumonia* (ATCC 49619), *S. pyogenes* (ATCC 19615), *S. pneumonia* (163, Mef A), *S. pneumonia* (303, ErmB), *S. aureus* (MRSA, 33591), *H. influenzae* (ATCC 49247), *S. pneumonia* (3773, ErmB), *S. pneumonia* (5032), *S. pyogenes* (1721), *S. pyogenes* (1850), *S. pyogenes* (3029), and *S. pyogenes* (3262).

In another illustrative embodiment, compounds of Formula (I) are described herein where X and Y are taken together with the attached carbon to form a C(O) group. In another embodiment, X is H, Y is $OR^7$, where $R^7$ is a monosaccharide radical, such as cladinosyl. In another embodiment, compounds of Formula (I) are described herein where W is fluoro. In another embodiment, compounds of Formula (I) are described herein where A and B are taken together to form an alkylene group, including but not limited to propylene, butylene, and pentylene. In another embodiment, compounds of Formula (I) are described herein where A and B are taken together to form butylene. In another embodiment, compounds of Formula (I) are described herein where A and B are taken together to form pentylene. In another embodiment, compounds of Formula (I) are described herein where A and B are taken together to form butylenes and C is 2-pyridinyl or aminophenyl, such as 3-aminophenyl. In another embodiment, compounds of Formula (I) are described herein where A and B are taken together to form propylenes, butylenes, or pentylenes; and C is aminophenyl, such as 3-aminophenyl. In another embodiment, compounds of Formula (I) are described herein where A and B are taken together to form pentylene and C is 3-pyridinyl or benzotriazole. In another embodiment, compounds of Formula (I) are described herein where C is an optionally substituted aryl or heteroaryl group. In another embodiment, compounds of Formula (I) are described herein where V is a carbonyl group. In another embodiment, compounds of Formula (I) are described herein where $R^{10}$ is hydrogen. In another embodiment, X is H, Y is $OR^7$, where $R^7$ is a monosaccharide radical, such as cladinosyl, and C is 3-pyridinyl or benzotriazolyl.

In another embodiment, C is optionally substituted phenyl, such as phenyl, halophenyl, haloalkylphenyl, aminophenyl, and the like, optionally substituted pyridinyl, such as 2-pyridinyl and 3-pyridinyl, optionally substituted benzotriazole, and the like.

In another embodiment, A and B are taken together to form butylene or pentylene, and X and Y are taken together with the attached carbon to form a C(O) group.

In another embodiment, compounds described in any of the preceding embodiments wherein V is C(O) are described. In another embodiment, compounds described in any of the preceding embodiments wherein W is H or F are described. In another embodiment, compounds described in any of the preceding embodiments wherein A is $CH_2$, B is $(CH_2)_n$, and n is an integer from 2-4 are described. In another embodiment, compounds described in any of the preceding embodiments wherein C is aryl or heteroaryl are described. In another embodiment, compounds described in any of the preceding embodiments wherein C is 3-aminophenyl or 3-pyridinyl are described. In another embodiment, compounds described in any of the preceding embodiments wherein $R_{10}$ is hydrogen. In another embodiment, compounds described in any of the preceding embodiments wherein A and B are taken together to form butylene or pentylene, and X and Y are taken together with the attached carbon to form a C(O) group. In another embodiment, compounds described in any of the preceding embodiments wherein A and B are taken together to form butylene or pentylene, and X and Y are taken together with the attached carbon to form a C(O) group, and W is F.

In another embodiment, an antibacterial composition is described herein, wherein the composition includes an effective amount of one or more compounds described herein, and a pharmaceutically acceptable carrier, excipient, or diluent therefor, or a combination thereof.

As used herein, the term "composition" generally refers to any product comprising the specified ingredients in the specified amounts, as well as any product which results, directly or indirectly, from combinations of the specified ingredients in the specified amounts. Illustratively, compositions may include one or more carriers, diluents, and/or excipients. The compounds described herein may be formulated in a therapeutically effective amount in conventional dosage forms for the methods described herein, including one or more carriers, diluents, and/or excipients therefor. Such formulation compositions may be administered by a wide variety of conventional routes for the methods described herein in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known in the medical arts.

In one embodiment, the compounds described herein are administered to a human orally at a dose of about 1 to about 10 mg/kg, about 2 to about 8 mg/kg, or about 4 to about 6 mg/kg of patient body weight. In another embodiment, the daily adult human dose is about 100 to about 1,000 mg, which may be administered qd, bid, tid, and the like. In another embodiment, the daily adult human dose is about 400 to about 600 mg, which may be administered qd, bid, tid, and the like. Such doses may be administered, once, twice, or thrice per day. Illustrative oral unit dosages are 50, 100, 200, and 400 mg (single or divided). Without being bound by theory, it is believed that such illustrative dosages are sufficient to achieve plasma levels of about 1 μg/mL, which may be sufficient to observe bactericidal activity of the compounds described herein, such as for macrolide-susceptible pneumococci. It is appreciated that as described herein, the compounds described herein, including CEM-101, reach high concentration in tissues, such as lung tissues. Without being bound by theory, it is believed herein that the compounds described herein, including CEM-101, may achieve tissue levels that are at least about 10-times the MIC for strains, including macrolide-resistant strains, such as but not limited to *H. influenzae* and *H. influenzae* resistant to AZI, *S. pyogenes* and *S. pneumoniae* resistant to any one of AZI, CLR, CTH, and/or TEL, and other resistant organisms described herein.

The compounds described herein may be prepared as described herein, or according to US Patent Application Publication No. 2006/0100164 and in PCT International Publication No. WO 2009/055557, the disclosures of which are incorporated herein by reference in their entirety.

Briefly, the synthesis of triazole containing ketolides begins with the known two step preparation of the 12-acyl-imidazole intermediate 4 (Scheme I) from CLR (2). Intermediate 4 is converted into the 11,12-cyclic carbamates 5a-c by the reaction with the corresponding 3-, 4- or 5-carbon linked amino alcohols. Treatment of 5a-c with tosyl chloride provides tosylates 6a-c. Displacement of the tosyl group with $NaN_3$ gives the corresponding azido compounds 7a-c. Cleavage of the cladinose sugar of 7a-c to 8a-8c is accomplished by treatment with HCl in MeOH. Swern oxidation of the 3-hydroxy group of 8a-c gives the corresponding protected ketolides 9a-c which are subsequently deprotected with methanol to afford the required azido ketolides 10a-c, respectively. These azido compounds were reacted with terminally-substituted alkynes in the presence of copper iodide in toluene at 60° C. to regio-selectively afford the corresponding 4-substituted-[1,2,3]-triazoles 11a-18a, 11b-18b, and 11c-18c.

The azide of intermediates 10a-c is converted to the 4-substituted-[1,2,3]-triazoles via a cycloaddition reaction with substituted acetylenes. Triazole rings may be formed via a Huisgen 1+3 cycloaddition reaction between an azide and an alkyne resulting in a mixture of 1,4- and 1,5-regioisomers as depicted in Route A of Scheme II. Alternatively, the procedure of Rostovtsev et al.[8] may be followed using the addition of a CuI catalyst to the reaction to selectively or exclusively produce the 1,4-regioisomer as depicted in Route B of Scheme II.

The triazole ring side chain is also incorporated into the CLR ring system. In one embodiment, a butyl alkyl side chain is chosen. It is appreciated that many butyl side chain analogs in the ketolide series have improved antibacterial activity based on in vitro MIC results. Intermediate 7b is directly converted into the 4-substituted-[1,2,3]-triazole via copper catalyzed cyclization with terminally substituted acetlyenes, as shown in Scheme III. The acetate protecting groups of 19a-e are removed with LiOH in methanol to afford the corresponding 4-substituted-[1,2,3]-triazoles 20a-e.

Substitution of the 2-position hydrogen with a fluorine is accomplished by electrophilic fluorination of 9b (Scheme IV) using Selectfluor®. The azido group of intermediate 22 is converted to a series of 4-substituted-[1,2,3]-triazoles 23a-b via the standard conditions.

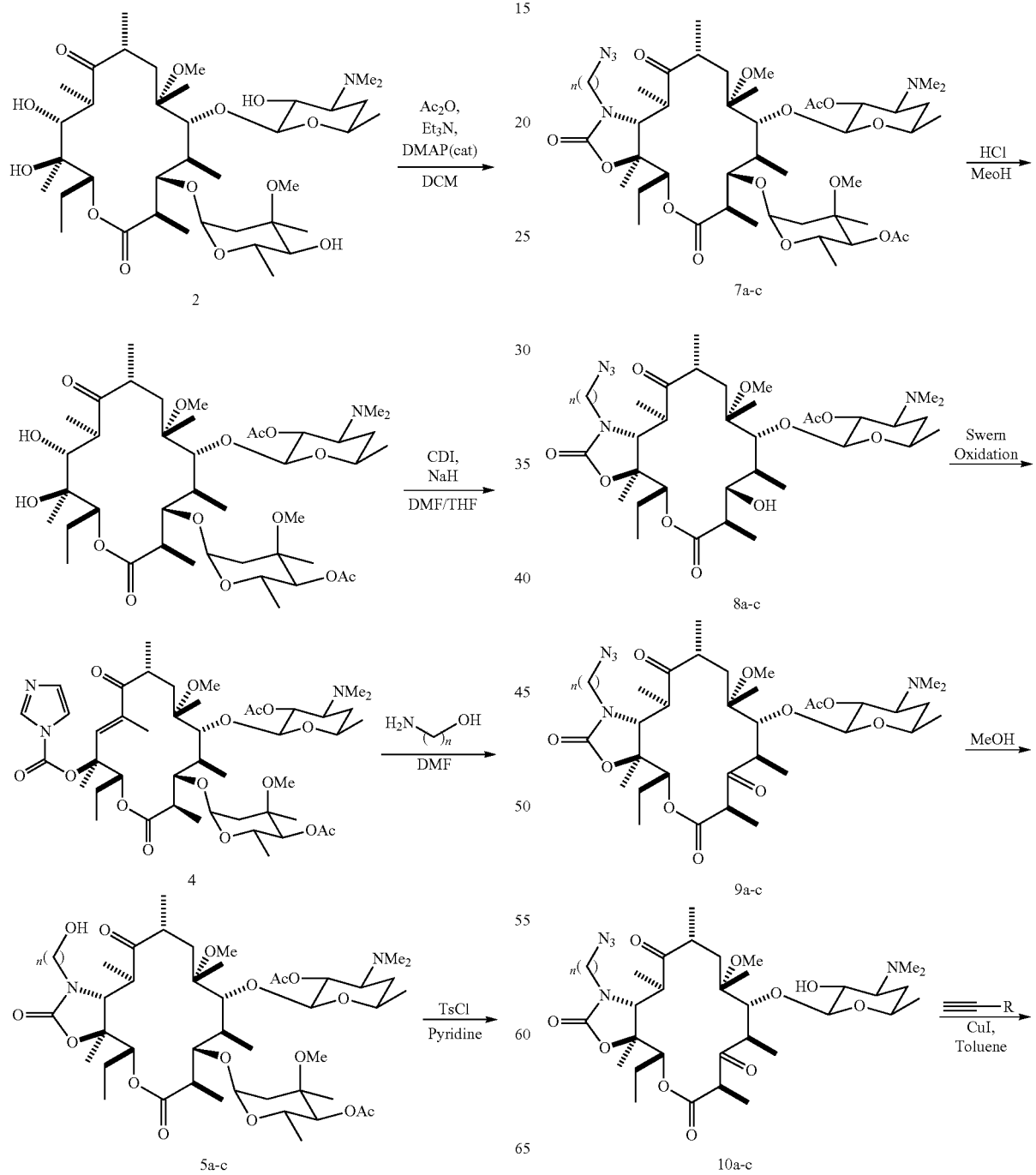

21
-continued
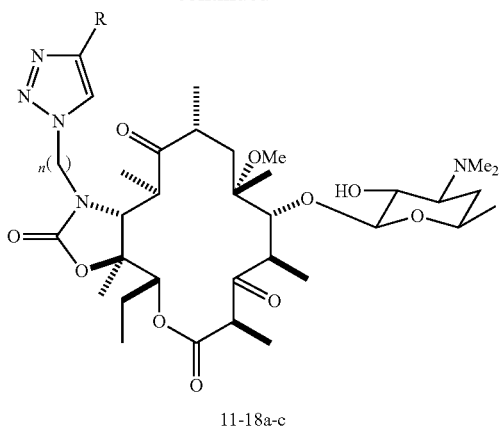
11-18a-c
Scheme II
22
-continued
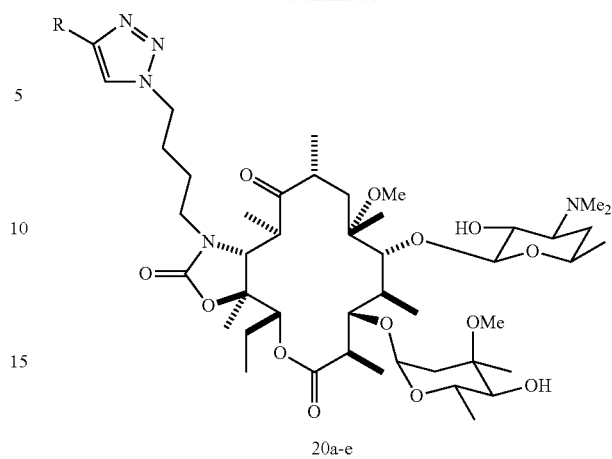
20a-e
Scheme III
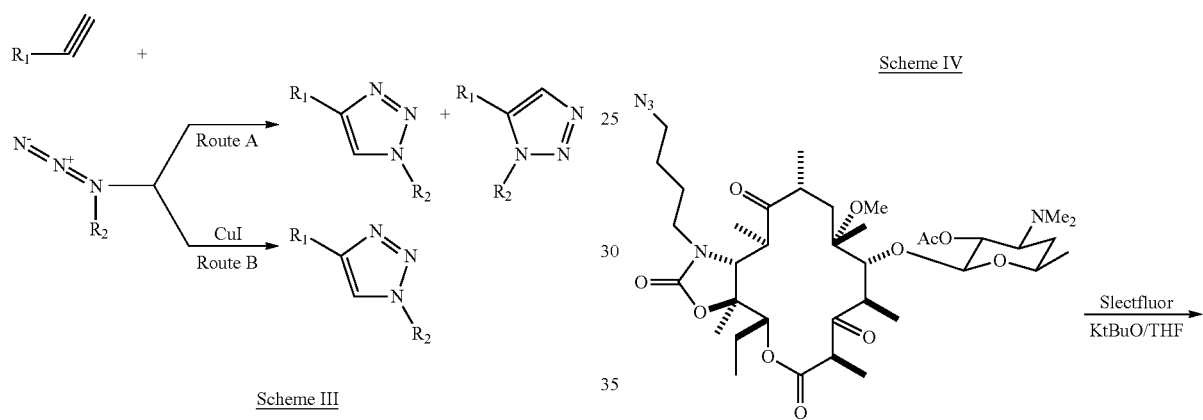
Scheme IV
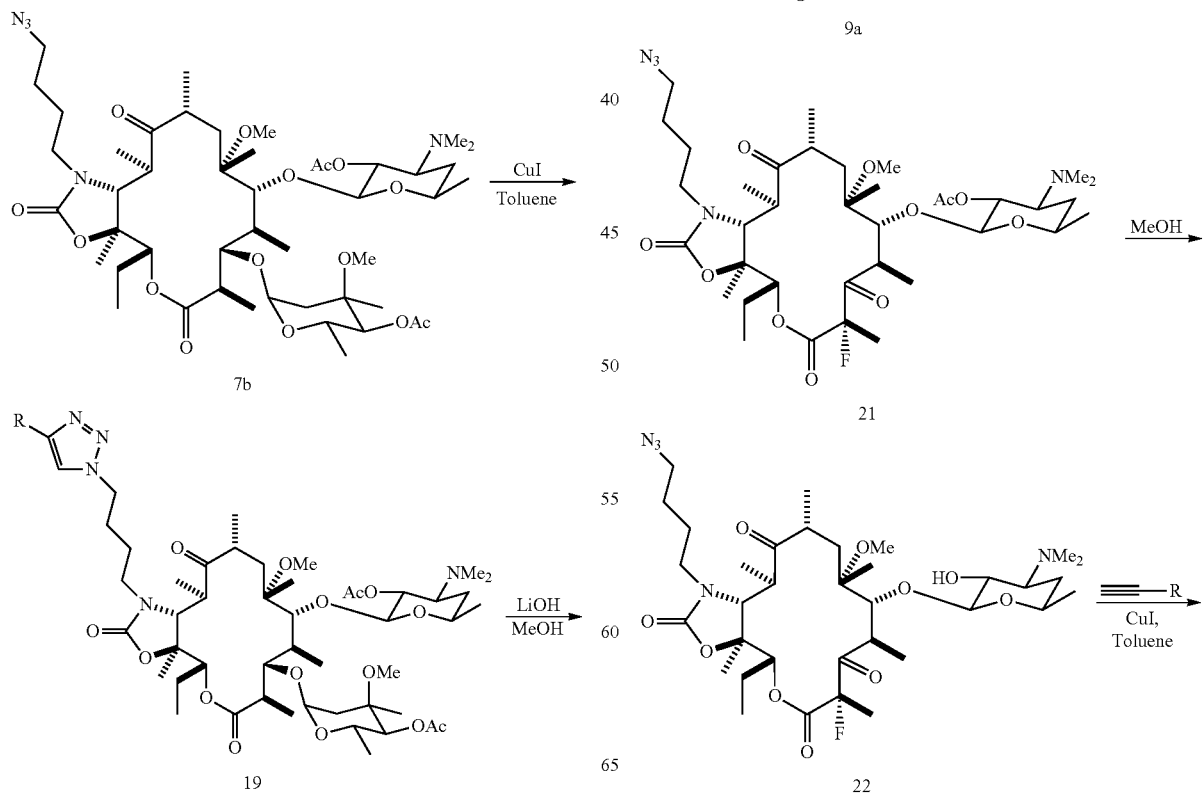

-continued
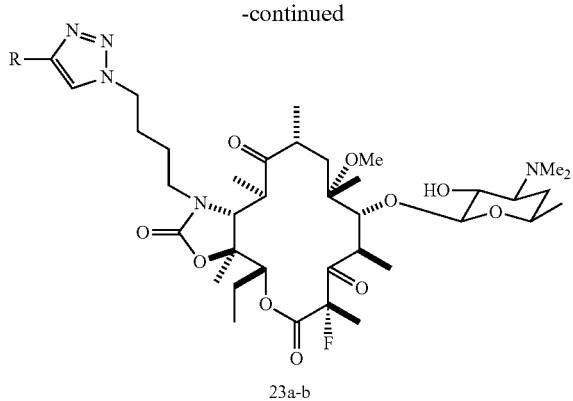
23a-b
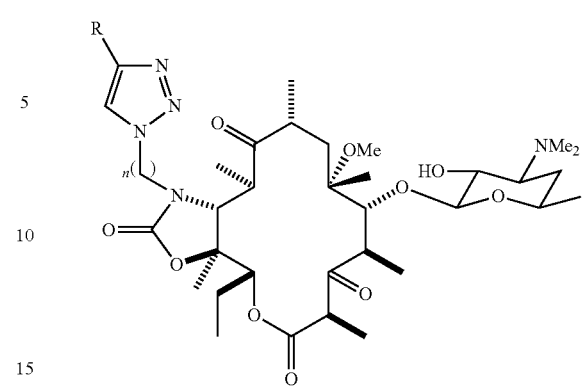
24
In another embodiment, the following compounds are described:
| | | | Minimum inhibitory concentration (µg/mL)[a] | | | | | |
|---|---|---|---|---|---|---|---|---|
| | | | S. aureus | | | S. pneumoniae | | H. influenzae |
| | | | | 96:11480 | | | | |
| Entry | R | n | 29213 Ery-S | Ery-R (MLSb) | 49619 Ery-S | 163 Ery-R (MefA) | 303 Ery-R (emB) | 49247 Ery-S |
| TEL | | | ≤0.125 | ≤0.125 | ≤0.125 | ≤0.125 | ≤0.125 | 4 |
| AZI | | | ≤0.125 | >64 | ≤0.125 | >64 | >64 | 2 |
| 11a | phenyl | 3 | 1 | 1 | ≤0.125 | ≤0.125 | >64 | >64 |
| 11b | | 4 | ≤0.125 | 0.25 | ≤0.125 | ≤0.125 | 2 | 8 |
| 11c | | 5 | ≤0.125 | ≤0.125 | ≤0.125 | ≤0.125 | 0.25 | 16 |
| 12a | 4-Br-phenyl | 3 | 0.25 | 0.5 | ≤0.125 | ≤0.125 | 8 | 64 |
| 12b | | 4 | ≤0.125 | ≤0.125 | ≤0.125 | ≤0.125 | 8 | 8 |
| 12c | | 5 | ≤0.125 | ≤0.125 | ≤0.125 | ≤0.125 | 1 | 16 |
| 13a | 4-CF$_3$-phenyl | 3 | 1 | 2 | ≤0.125 | ≤0.125 | 16 | >64 |
| 13b | | 4 | 0.25 | 0.25 | ≤0.125 | ≤0.125 | 8 | 8 |
| 13c | | 5 | 0.5 | 1 | ≤0.125 | 0.5 | 2 | 64 |
| 14a | 2-pyridyl | 3 | 2 | 2 | ≤0.125 | 0.5 | >64 | >64 |
| 14b | | 4 | ≤0.125 | ≤0.125 | ≤0.125 | ≤0.125 | ≤0.125 | 4 |
| 14c | | 5 | ≤0.125 | ≤0.125 | ≤0.125 | ≤0.125 | 0.25 | 64 |
| 15a | 3-pyridyl | 3 | 2 | 2 | ≤0.125 | 1 | >64 | >64 |
| 15b | | 4 | ≤0.125 | 4 | ≤0.125 | 2 | 64 | 64 |
| 15c | | 5 | ≤0.125 | 0.25 | ≤0.125 | 0.25 | 4 | 16 |

-continued

| | | | Minimum inhibitory concentration (μg/mL)[a] | | | | | |
|---|---|---|---|---|---|---|---|---|
| | | | S. aureus | | | S. pneumoniae | | H. influenzae |
| | | | | 96:11480 | | | | |
| Entry | R | n | 29213 Ery-S | Ery-R (MLSb) | 49619 Ery-S | 163 Ery-R (MefA) | 303 Ery-R (emB) | 49247 Ery-S |
| 16a | 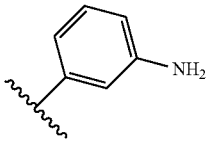 [SMILES: *c1cccc(N)c1] | 3 | 0.5 | nt | ≤0.125 | ≤0.125 | >64 | 16 |
| 16b | | 4 | ≤0.125 | ≤0.125 | ≤0.125 | ≤0.125 | ≤0.125 | 2 |
| 16c | | 5 | ≤0.125 | ≤0.125 | ≤0.125 | ≤0.125 | 0.25 | 8 |
| 17a | 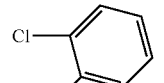 | 3 | 1 | 1 | ≤0.125 | ≤0.125 | >64 | >64 |
| 17b | | 4 | ≤0.125 | ≤0.125 | ≤0.12 | ≤0.12 | 1 | 16 |
| 17c | | 5 | 0.25 | 0.5 | ≤0.125 | ≤0.125 | 2 | 32 |
| 18a | 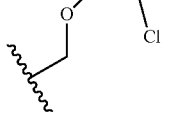 | 3 | 1 | 2 | ≤0.125 | 0.5 | >64 | >64 |
| 18b | | 4 | 1 | 2 | ≤0.125 | 4 | 64 | 32 |
| 18c | | 5 | ≤0.125 | ≤0.125 | ≤0.125 | ≤0.125 | 64 | 8 |

[a]National Committee for Clinical Laboratory Standards. Methods for Dilution Antimicrobial Susceptibility Tests for Bacteria that Grow Aerobically, 6th ed.; Approved standard: NCCLS Document M7-A6, 2003.

In another embodiment, the following compounds are described:

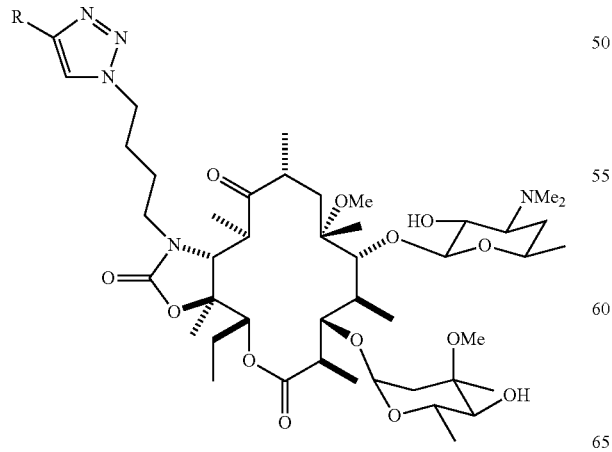

| Entry | R | S. aureus 25923 Ery-S | RN220 | S. pneumoniae 49619 Ery-S | 163 Ery-R (MefA) | 303 Ery-R (emB) | H. influenzae 49247 Ery-S |
|---|---|---|---|---|---|---|---|
| TEL |  | ≤0.25 | 2 | ≤0.125 | ≤0.125 | ≤0.125 | 4 |
| 20a | 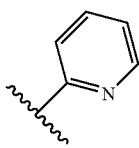 [SMILES: *c1ccccn1] | 0.25 | 8 | ≤0.0625 | 0.125 | 2 | NT |
| 20b | 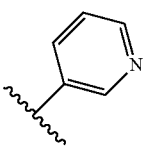 [SMILES: *c1cccnc1] | 0.25 | 8 | ≤0.0625 | ≤0.06 | 1 | NT |
| 20c | 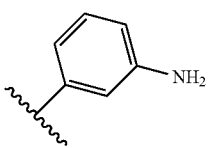 [SMILES: *c1cccc(N)c1] | 1 | 8 | ≤0.0625 | 0.5 | 2 | NT |
| 20d | 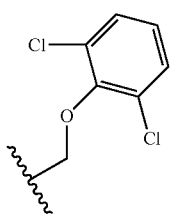 [SMILES: *COc1c(Cl)cccc1Cl] | 1 | 8 | ≤0.0625 | 0.5 | 2 | NT |
| 20e | 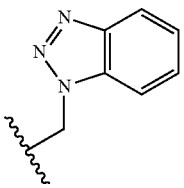 [SMILES: *Cn1nnc2ccccc21] | ≤0.25 | 8 | ≤0.0625 | 0.5 | 2 | NT |
In another embodiment, the following compounds are described:
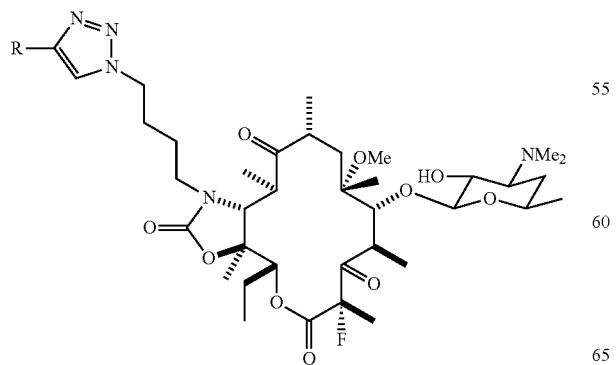

| | | S. aureus | | S. pneumoniae | | | H. influenzae |
|---|---|---|---|---|---|---|---|
| Entry | R | 29213 Ery-S | 96:11480 Ery-R (MLSb) | 49619 Ery-S | 163 Ery-R (MefA) | 303 Ery-R (ermB) | 49247 Ery-S |
| TEL | | ≤0.125 | ≤0.125 | ≤0.125 | ≤0.125 | ≤0.125 | 4 |
| AZI | | ND | ≤0.125 | >64 | ≤0.125 | >64 | >64 |
| 23a | *2-pyridyl* | ≤0.125 | ≤0.125 | ≤0.125 | ≤0.125 | ≤0.125 | 2 |
| 23b (CEM-101) | *3-aminophenyl (NH2)* | ≤0.06 | ≤0.125 | ≤01.25 | ≤0.125 | ≤0.125 | 2 |

In each of the foregoing embodiments, the primary screening panel consisted of relevant *Staph. aureus, S. pyogenes, S. pneumoniae* (including strains resistant to AZI and TEL). MICs against all pathogens were determined using broth microdilution method as per NCCLS guidelines. Compounds described herein, such as CEM-101 were found to be highly potent having MICs against *S. pneumoniae* (3773) of ≤0.125 μg/mL and *S. pyogenes* (1850) of 0.5 μg/mL, compared to 1 and 8 μg/mL, respectively for TEL. CEM-103 (20c), an analogue of CEM-101 that contains the 3-O-cladinose was found to be less active. Non-heteroaromatic substituted triazole containing ketolides were less active.

The ketolides were tested against erythromycin-sensitive (Ery-S) and erythromycin-resistant (Ery-R) strains of *S. aureus* (29213 (Ery-S) and 96:11480 (Ery-R)), *S. pneumoniae* (49619 (Ery-S) and 163 and 303 (Ery-R)) and *H. influenzae* (49247 (Ery-S)) (Tables 1-3). The broth micro-dilution method was used to determine the Minimum Inhibitory Concentrations (MICs) against all pathogens as per the Clinical and Laboratory Standards Institute (CLSI).

The chain length of the alkyl side chain affected activity (Table 1). For example, the 3-carbon linked phenyl substituted triazole 11a was less active against Ery-S and Ery-R *S. aureus* and was inactive against Ery-R *S. pneumoniae* 303 (ermB) a the tested concentrations, whereas the corresponding 4- and the 5-carbon linked phenyl substituted triazoles 11b and 11c were more active against these organisms. A similar trend was observed for the 2-pyridyl substituted triazoles 14a-c, the 3-amino-phenyl substituted triazoles 16a-c, and the 2,5-dichlorophenoxy substituted triazoles 17a-c.

The 4-carbon linked 2-pyridyl substituted triazole 14b and the 3-amino-phenyl substituted triazole 16b possessed the highest potency against *S. pneumoniae* 303, both having MIC values (≤0.125 μg/mL) comparable to TEL. The ketolide containing the 4-carbon linked 3-pyridyl substituted triazole 15b was less active against this strain (MIC of 64 μg/mL). Within this series antibacterial activity was improved by extending the carbon linker to 5 atoms, for example the MIC against *S. pneumoniae* 303 for compound 15c improved from 64 to 4 μg/mL. A similar effect was also observed for the benzo-triazole containing ketolide 18c against *S. aureus* but 18c was still inactive against *S. pneumoniae* 303. It is appreciated that a balance between the length of the linker and nature of the aromatic substitution of the triazole may affect the overall activity against macrolide resistant *S. pneumonia* and *S. aureus*.

A correlation between linker length and activity was also observed for *H. influenzae* (49247) where the most potent ketolide series had the substituted triazole linked through either a 4-carbon (11b-14b, 16b, 17b) or a 5-carbon (15c, 18c) chain. Interestingly, the most potent aromatic series against *H. influenzae* was the 3-amino-phenyl with a 3-, 4- or 5-carbon linker (16a, 16b, 16c) having MICs of 16, 2, and 8 μg/mL, respectively, The macrolides containing a cladinose at the 3 position were all highly active against Ery-S *S. pneumoniae* (49619) (Table 2). However, these analogs were less potent than TEL against Ery-R strains. The MICs were significantly higher for the cladinose containing analogs with either 2-pyridyl, 2-aminophenyl or 2,6-dichlorophenyl triazole substituents than for the corresponding ketolides (20a, 20c, and 20d versus 14b, 16b, and 17b). Conversely, antibacterial activity was re-established for ketolide analogs 15b (3-pyridyl) and 18b (benzo-triazole) by replacing the keto with the cladinose group in analogs 20b (3-pyridyl) and 20e (benzo-triazole). The MICs improved from 64 μg/mL for 15b and 18b to 1 and 2 μg/mL for 20b and 20e, respectively. A similar activity trend was also observed for Ery-R *S. pneumoniae* 163 (MefA).

COMPOUND EXAMPLES

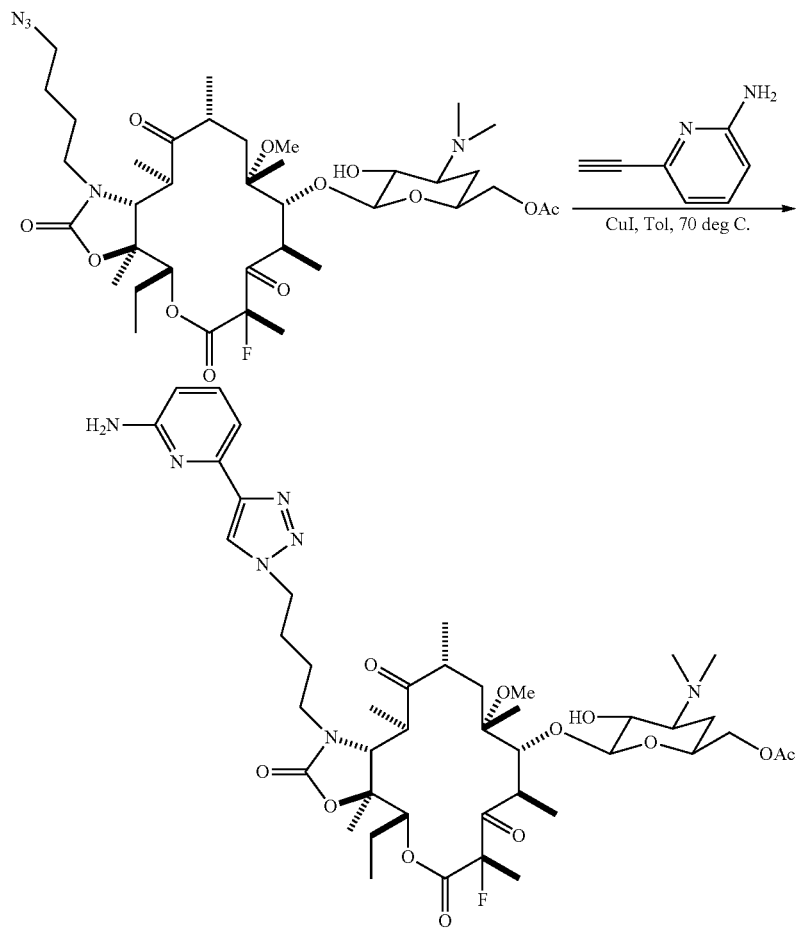

A mixture of 11-N-(4-Azido-butyl)-6-O-methyl-5-(3-dimethylamine-4-deoxy-6-O-acetyl-glu-copyranosyl)-2-fluoro-3-oxo-erythronolide A, 11,12-carbamate (15 mg, 0.019 mmol), 6-Ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 14 mg of the desired compound. MS: $C_{44}H_{66}FN_7O_{12}$ calculated $M^+$=903.5. Found: $M+H^+$=904.5.

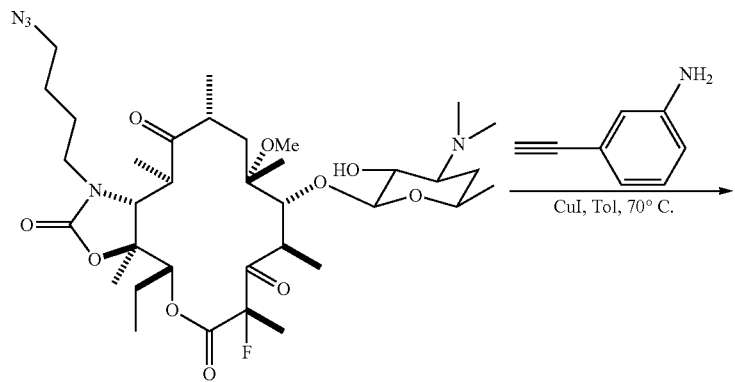

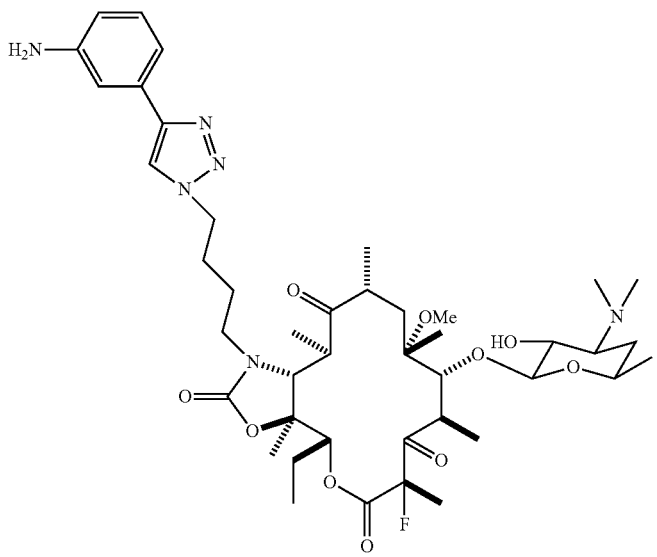

11-N-4-(3-aminophenyl)-[1,2,3]triazol-1-yl]-butyl}-5-desosaminyl-3-oxo-2-fluoro-erythronolide A, -11,12-cyclic carbamate (CEM-101). A mixture of 11-N-(4-azido-butyl)-6-O-methyl-5-desosamynyl-3-oxo-2-fluoro-erythronolide A, 11,12-carbamate (17 mg, 0.023 mmol), 3-Ethynyl-phenylamine (5.4 mg, 0.046 mmol), CuI (1 mg, 0.005 mmol), and toluene (0.2 mL) was heated to 70° C. After 16 h, the mixture was concentrated and directly subjected to silica gel chromatography (9:1, chloroform: methanol plus 1% ammonium hydroxide) to give 17 mg of the desired compound, MS $C_{43}H_{65}FN_6O_{10}$ calculated $M^+$=844.47. Found: $M+H^+$=845.5.

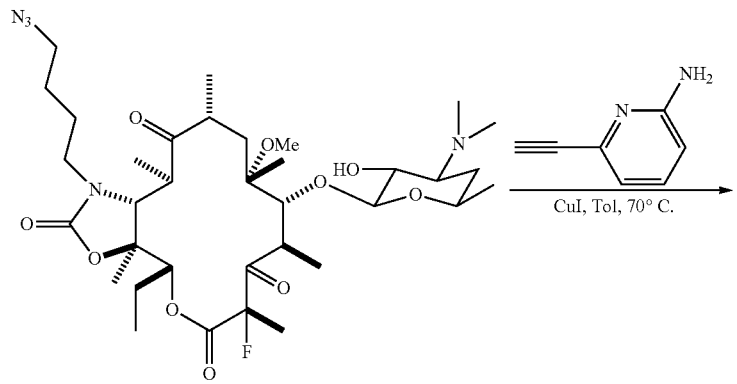

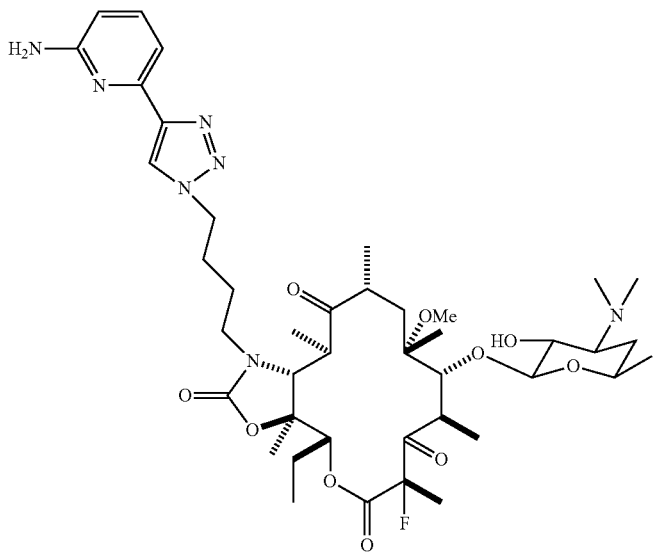

11-N-{4-[4-(6-Amino-pyridin-2-yl)-[1,2,3]triazol-1-yl]-butyl}-5-desosaminyl-3-oxo-2-fluoro-erythronolide A, -11,12-cyclic carbamate. A mixture of 11-N-(4-azido-butyl)-6-O-methyl-5-desosamynyl-3-oxo-2-fluoro-erythronolide A, 11,12-carbamate (15 mg, 0.02 mmol), 6-ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 14 mg of the desired compound OP1357. MS: $C_{42}H_{64}FN_7O_{10}$ calculated $M^+=845.5$. Found: $M+H^+=846.5$.

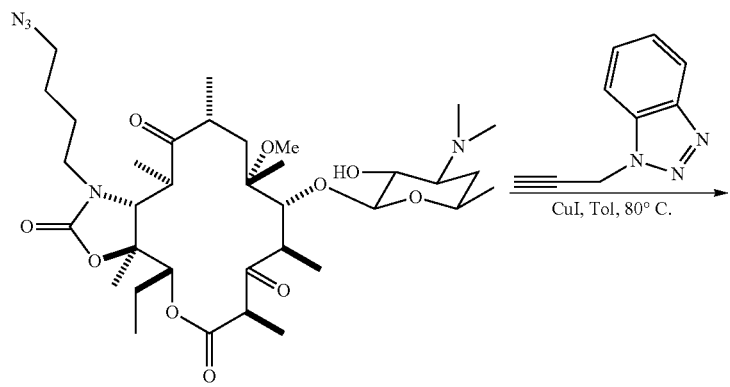

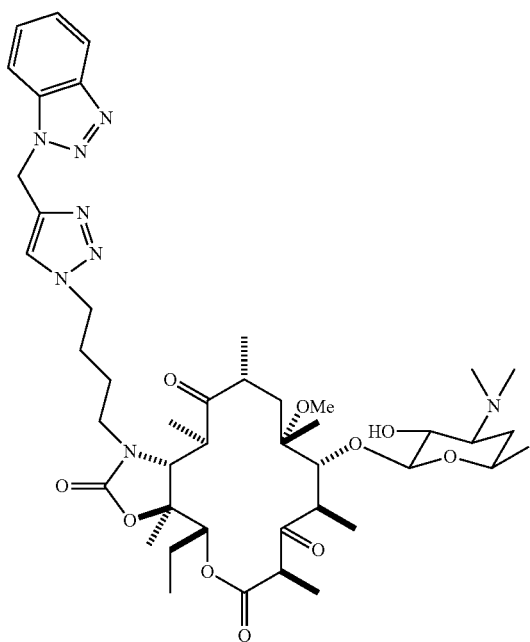

11-N-[4-(4-Benzotriazol-1-ylmethyl-[1,2,3]triazol-1-yl)-butyl]-6-O-methyl-5-O-dasosaminyl-3-oxo-erythronolide A, 11,12-carbamate. A mixture of 11-N-(4-Azido-butyl)-6-O-methyl-5-O-desosaminyl-3-oxo-erythronolide A, 11,12-carbamate (3 mg, 0.0039 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform: methanol plus 1% ammonium hydroxide) to give 3 mg of the desired compound. MS: $C_{44}H_{66}N_8O_{10}$ calculated $M^+=866.5$. Found: $M+H^+867.5$.

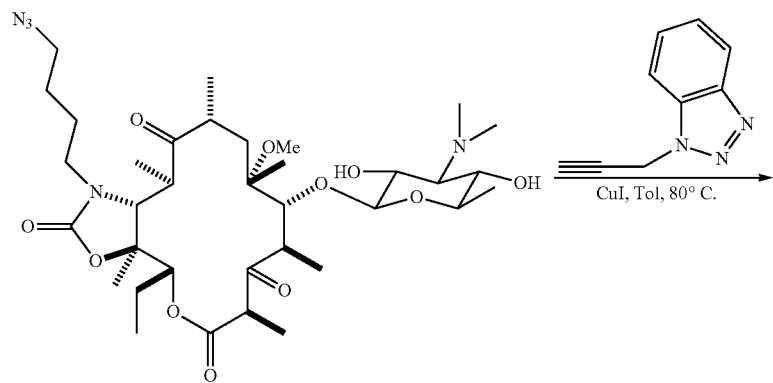

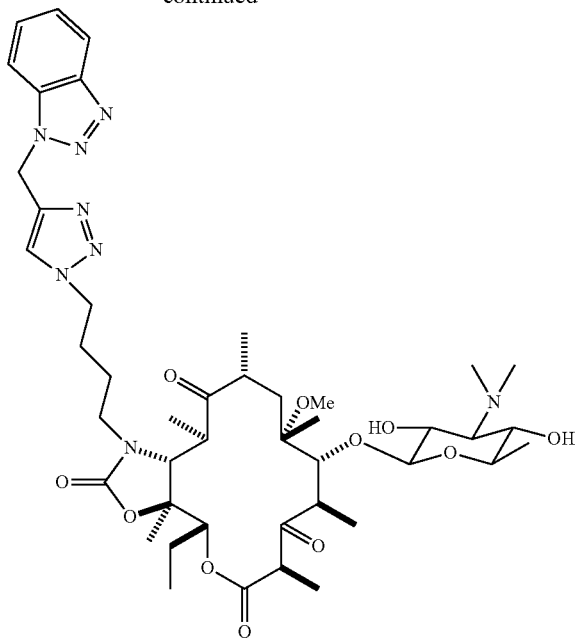

11-N-[4-(4-Benzotriazol-1-ylmethyl-[1,2,3]triazol-1-yl)-butyl]-6-O-methyl-5-mycaminosyl-3-oxo-erythronolide A, 11,12-carbamate. A mixture of 11-N-(4-azido-butyl)-6-O-methyl-5-mycaminosyl-3-oxo-erythronolide A, 11,12-carbamate (3 mg, 0.004 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform: methanol plus 1% ammonium hydroxide) to give 3 mg of the desired compound. MS: $C_{44}H_{66}N_8O_{11}$ calculated $M^+=882.5$. Found: $M+H^+=883.5$.

METHOD EXAMPLES

Example

The in vitro activities of CEM-101 is compared with those of AZI, CLR, TEL and doxycycline against 10 isolates of *C. pneumoniae* and 10 strains of *C. trachomatis* in HEp-2 cells. The MIC at which 50% and 90% of the isolates of *C. pneumoniae* are inhibited by CEM-101 was 0.25 µg/ml (range: 0.25 to 1.0 µg/ml). The MIC at which 50% and 90% of the strains of *C. trachomatis* were inhibited was 0.25 µg/ml (range: 0.125 to 0.5 µg/ml). The MIC90s for both *C. trachomatis* and *C. pneumoniae* against AZI, CLR, TEL, and doxycycline were 0.125, 0.06, 0.06, 0.06 µg/ml, respectively. The MICs of CEM-101 were consistent from isolate to isolate, varying by only one or two dilutions, which is especially impressive given the wide geographical distribution of the isolates tested. These results indicate that CEM-101 and the compounds described herein is an effective antibiotic for treating *C. trachomatis* and respiratory tract infections caused by *C. pneumoniae*.

Example

36 *M. pneumoniae* were collected from the respiratory tract of adults and children with pneumonia between 1992 and 2006. 2 isolates collected from children in Birmingham, Ala. in 2005 were macrolide-resistant (AZI MICs>32 µg/ml); both of which had been shown to have an A2063G mutation in domain V of the rRNA gene. 5 *M. genitalium* included reference strains obtained from the urogenital tracts of patients in the United States (3 isolates) and Denmark (2) isolates. 15 *M. fermentans* from the respiratory or urogenital tracts were obtained from the *Mycoplasma* Collection at the National Institutes of Health and patients in Birmingham, Ala. between 1992 and 2004. 13 *M. hominis* were obtained from clinical specimens of the urogenital tract or wounds between 1994 and 2007. 2 isolates were resistant to doxycycline (MICs 8-16 µg/ml). 10 *Ureaplasma parvum* were obtained from urogenital specimens between 2002 and 2005. 7 were doxycycline-resistant (MICs 4-16 µg/ml). 10 *U. urealyticum* were obtained from various urogenital tract specimens, placentas or neonatal respiratory secretions between 1990 and 2005. 4 were resistant to doxycycline (MICs 4-32 µg/ml).

All *mycoplasma* and *ureaplasma* isolates were inhibited by CEM-101 at concentrations <0.5 µg/ml, making it the most potent compound tested overall. *M. pneumoniae* MICs for CEM-101 ranged from 0.000000063-0.5 µg/ml with MIC90=0.000125, making its activity 4-fold greater than AZI, 8-fold greater than TEL. LZD was inactive against *M. pneumoniae*, but some *M. fermentans* and *M. hominis* had MICs<1 mg/ml. 2 macrolide-resistant MP with AZI and TEL with MICs greater than 32 µg/ml were inhibited by CEM-101 at 0.5 µg/ml. CEM-101 MBCs were greater than 16-fold greater than MICs for 9 *M. pneumoniae* indicating the drug is bacteriostatic against this organism. CEM-101 was active against all doxycycline-resistant *M. hominis* and *Ureaplasma* spp. Excluding 2 macrolide-resistant *M. pneumoniae*, no isolate of any species tested had an MIC greater than 0.063 µg/ml for CEM-101.

MIC Testing. Antimicrobial powders were dissolved as instructed by the manufacturer and frozen in 1 ml aliquots containing 2048 µg/ml. Drugs tested included: CEM-101, AZI, TEL, doxycycline, levofloxacin, and linezolid. A working dilution of each drug was prepared on the day of each assay based on the anticipated MIC ranges for each drug. Serial 2-fold antimicrobial dilutions were performed in 10B broth for *Ureaplasma* spp. and SP4 broth for *Mycoplasma* spp. in 96 well microtiter plates. For macrolides and ketolides tested against *M. pneumoniae*, dilutions were taken down to 0.000000063 µg/ml to measure the endpoint MIC for these potent agents. 0.175 mL inoculum of 104-105 CCU/ml obtained by inoculation of organisms from frozen stock of known concentration into prewarmed broth and incubating 2 hrs at 37° C. was added to the drug dilutions. Plates were sealed, incubated aerobically at 37° C. in air and examined daily until a color change was detected in the drug-free growth control. MIC=the lowest concentration of a drug in which the metabolism of the organisms was inhibited as evidenced by lack of color change at the time the drug free control first showed color change.

Quality Control. The inoculum of each isolate was verified by serial dilutions and plate counts. Quality control strains used to validate accuracy of MICs for comparator antimicrobial agents included *M. pneumoniae* (UAB-834), *M. hominis* (UAB-5155) and *U. urealyticum* (UAB-4817), all of which are low passage clinical isolates for which a 3 dilution MIC range has been established.

|  | MIC Range µg/mL | $MIC_{50}$ µg/mL | $MIC_{90}$ µg/mL |
|---|---|---|---|
| *M. pneumoniae* (36 isolates) | | | |
| CEM-101 | ≤0.000000063-0.5 | 0.000032 | 0.000125 |
| AZI | ≤0.000016-≥32 | 0.00025 | 0.0005 |
| TEL | 0.000031-≥32 | 0.00025 | 0.001 |
| Doxycycline | 0.016-0.25 | 0.125 | 0.25 |
| Levofloxacin | 0.125-1 | 0.5 | 0.5 |
| Linezolid | 32-128 | 64 | 128 |
| *M. genitalium* (5 isolates) | | | |
| CEM-101 | ≤0.000032 | NA | NA |
| AZI | ≤0.000032-0.005 | NA | NA |
| TEL | ≤0.00003-0.00025 | NA | NA |
| Doxycycline | ≤0.008-0.031 | NA | NA |
| Levofloxacin | 0.125-1 | NA | NA |
| Linezolid | 4-128 | NA | NA |
| *M. fermentans* (15 isolates) | | | |
| CEM-101 | ≤0.008 | ≤0.008 | ≤0.008 |
| AZI | 0.125-1 | 0.5 | 0.5 |
| TEL | 0.002-0.031 | ≤0.008 | 0.016 |
| CLN | ≤0.008-0.063 | 0.016 | 0.031 |
| Doxycycline | 0.016-0.5 | 0.125 | 0.5 |
| Levofloxacin | ≤0.008-0.25 | 0.031 | 0.125 |
| Linezolid | 0.5-4 | 1 | 4 |
| *M. hominis* (13 isolates) | | | |
| CEM-101 | 0.002-0.008 | 0.004 | 0.008 |
| AZI | 0.5-4 | 4 | 2 |
| TEL | 0.125-0.5 | 0.25 | 0.5 |
| CLN | ≤0.008-0.031 | ≤0.008 | 0.016 |
| Doxycycline | ≤0.008-0.016 | 0.125 | 8 |
| Levofloxacin | 0.125-0.5 | 0.25 | 0.5 |
| Linezolid | 1-8 | 2 | 4 |
| *U. parvum* (10 isolates) | | | |
| CEM-101 | 0.002-0.031 | 0.008 | 0.016 |
| AZI | 0.5-4 | 2 | 4 |
| TEL | 0.008-0.063 | 0.063 | 0.125 |
| Doxycycline | 0.031-16 | 8 | 16 |
| Levofloxacin | 0.125-2 | 0.5 | 2 |
| Linezolid | 128->256 | >256 | >256 |
| *U. urealyticum* (10 isolates) | | | |
| CEM-101 | 0.004-0.063 | 0.008 | 0.031 |
| AZI | 0.5-4 | 2 | 4 |
| TEL | 0.016-0.25 | 0.063 | 0.25 |
| Doxycycline | 0.031-32 | 1 | 16 |
| Levofloxacin | 0.5-2 | 0.5 | 1 |
| Linezolid | 256->256 | >256 | >256 |

*M. pneumoniae* Macrolide MIC Distribution. All but two isolates tested against CEM-101 showed an MIC of 0.0001 µg/mL or less. In contrast, more than half all isolates tested against AZI or TEL showed an MIC of 0.0001 µg/mL or greater.

MBC Testing. 9 *M. pneumoniae* were tested to determine MBCs for CEM-101. Aliquots (30 µl) from each well that had not changed color at the time the MIC was read were added to 2.97 mL broth (1:100 dilution) to make certain drug is diluted below inhibitory concentration to allow living organisms to grow to detectable levels. Growth control was subcultured to ensure presence of viable organisms in the absence of drug. Broths were incubated at 37° C. MBC=concentration of antimicrobial in which no growth was apparent by lack of color change in broth after prolonged incubation. MBCs for 9 *M. pneumoniae* were all >16-fold greater than the corresponding MICs indicating CEM-101 is bacteriostatic against this organism.

Example

An in vitro model of mycobacterial growth arrest was developed using *Mycobacterium bovis* BCG. When an exponentially growing culture was transferred to an evacuated tube, growth continued; however, treatment with a source of nitric oxide (50 mM DETA-NO) halted growth immediately. Aeration restored growth. When the period of growth arrest exceeded 4 hrs, a time lag occurred before aeration could restore growth. This lag time was maximal after 16 hrs of growth arrest, at which point the lag before growth restoration was 24 hrs. Without being bound by theory, it is believed herein that these time lags may indicate that one transition period was required to achieve full arrest of growth and another to fully recover from growth arrest. Without being bound by theory, it is also believed herein that DETA-NO-induced growth arrest failed to protect from the lethal effects of anaerobic shock, which may have caused rapid cell lysis of both growing and growth-arrested cells. While growth arrest had no effect on the lethal action of rifampicin, it reduced fluoroquinolone lethality by 4- to 20-fold. Two fluoroquinolones, moxifloxacin and gatifloxacin, were equally lethal with exponentially growing cells, but moxifloxacin was 2-fold more active during growth arrest.

Example

The high potency of CEM-101 against *Streptococcus pneumoniae*, β-haemolytic and viridans group streptococci, *Staphylococcus* spp. and enterococci has been documented in early screening studies performed using reference Clinical and Laboratory Standards Institute (CLSI) methods. Since mechanisms and occurrences of resistance are increasing rapidly that may compromise the MLSB-ketolide class, the post-antibiotic effects (PAE), bactericidal activity (MBC and killing curves) and potential synergies of CEM-101 with five selected classes of antimicrobial agents when testing wild type (WT) and phenotypically/genotypically defined resistant organism subsets was assessed. MBC determinations for CEM-101, TEL, and CLR used CLSI methods for 40 strains (6 species groups). KC used 8 strains (6 species groups). PAE was tested (5 strains) at 4× concentration for 1 or 2 hours exposure; TEL control. Drug interaction (synergy) studies were performed on 20 strains (7 *S. aureus*, 6 β-haemolytic streptococci and 7 *S. pneumoniae*) by the checkerboard method. CEM-101 was combined with five agents (ceftriaxone, gentamicin, levofloxacin, trimethoprim/sulfamethoxazole [TMP/SMX] and vancomycin), each representing a distinct antimicrobial class.

The characterization of antimicrobial interactions into categories was defined as: complete synergy=four-fold or greater decrease in the MIC values of both agents; partial synergy=four-fold or greater decrease in the MIC value for one agent and a two-fold reduction in the MIC of the other; additive=twofold decrease in MIC values of both tested agents; antagonism=four-fold or greater increase in the MIC values of both agents; and indifference=no decrease in the MIC values of either agent or only a two-fold decrease or increase in the MIC of one agent.

| | CEM-101 drug interaction (synergy) categories tested in combination with other antimicrobials. | | | | | |
|---|---|---|---|---|---|---|
| | Synergy | | Addi- | Indif- | Antag- | Indeter- |
| Co-drug | Complete | Partial | tive | ferent | onism | minate |
| CRO | 0 | 2 | 5 | 12 | 0 | 1 |
| GEN | 2 | 2 | 4 | 12 | 0 | 0 |
| LEV | 0 | 0 | 3 | 17 | 0 | 0 |
| TMP/SMX | 0 | 2 | 4 | 14 | 0 | 0 |
| VAN | 0 | 1 | 6 | 13 | 0 | 0 |
| All | 2 | 7 | 22 | 68 | 0 | 1 |

The most common interaction category observed for the CEM-101 drug combination studies was indifference (68 occurrences), followed by additive (22), and partial synergy (7) effects. Synergy was only observed with CEM-101 and gentamicin for two *S. pneumoniae* strains. The combinations of CEM-101 with gentamicin, ceftriaxone, TMP/SMX, vancomycin and levofloxacin exhibited favorable interactions (complete/partial synergy or additive; 31% of all results) when testing *S. pneumoniae* strains; but indifferent interactions predominated among tested *S. aureus* and *S. pyogenes*. None of the combinations evaluated demonstrated antagonism.

MBC and killing curve studies: A total of 40 strains (10 *S. pneumoniae*, 10 *S. aureus*, and 5 each of β-haemolytic streptococci, viridans group streptococci, coagulase-negative staphylococci [CoNS] and enterococci) were MIC tested followed by MBC determinations using CLSI procedures (MIC and MBC range, 0.008-16 μg/ml). The lowest concentration of a tested agent that killed≥99.9% of the initial inoculum was defined as the MBC endpoint (Tables 2 and 3). Time kill bactericidal activity was performed for CEM-101, TEL, CLR, and AZI on eight selected strains according to methods described by Moody & Knapp, NCCLS M21-A3 and M26-A. The compounds were tested at 2×, 4×, 8× MIC; and colony counts were performed at T0, T2, T4, T8 and T24.

CEM-101 exhibited low MBC/MIC ratios (≤4) for BSA, SA and coagulase-negative staphylococci; and 2-fold greater potency than TEL. SA, enterococci and some macrolide/CLN-resistant (R) strains had higher ratios. KC results showed more rapid and greater cidal activity (concentration dependant) for CEM-101 compared to TEL. CEM-101/TEL PAE (hours) was: SA (2.3/2.6 hours), SPN (3.0/1.9), BSA (6.1/3.4), *H. influenzae* (3.7/1.2), *M. catarrhalis* (5.3/4.0). Interaction results with CEM-101 showing no antagonism and dominant additive or indifferent effects. CEM-101 exhibited cidal activity against several Gram-positive species at rates and an extent greater than TEL. PAE for CEM-101 was 2.3-6.1 and 3.7-5.3 hours for Gram-positive and Gram-negative strains, respectively. No antagonism was found in synergy analyses, with enhanced inhibition most noted for combinations with CRO, GEN and TMP/SMX.

| Distribution of isolates according to MBC/MIC ratio for CEM-101, TEL, CLR and AZI | | | | | | |
|---|---|---|---|---|---|---|
| Organism/Antimicrobial agent | No. of strains with MBC/MIC value of: | | | | | |
| (no. tested) | 1 | 2 | 4 | 8 | 16 | ≥32 |
| *S. pneumoniae* (10) | | | | | | |
| CEM-101 | 3 | 5 | 0 | 0 | 0 | 2 |
| Telithromycin | 2 | 6$^a$ | 0 | 0 | 0 | 2 |
| Clarithromycin | 2 | 3 | 1 | 0 | 0 | —$^b$ |
| Azithromycin | 2 | 4 | 0 | 0 | 0 | —$^b$ |
| β-haemolytic *streptococci* (5) | | | | | | |
| CEM-101 | 0 | 1 | 2 | 0 | 0 | 2 |
| Telithromycin | 0 | 1 | 1 | 1 | 0 | 2 |
| Clarithromycin | 0 | 0 | 1 | 1 | 0 | 2$^b$ |
| Azithromycin | 0 | 0 | 0 | 0 | 2 | 2$^b$ |
| *Viridans* group *streptococci* (5) | | | | | | |
| CEM-101 | 3 | 0 | 1 | 0 | 0 | 1 |
| Telithromycin | 2 | 1 | 1 | 0 | 0 | 1 |
| Clarithromycin | 0 | 0 | 1 | 0 | 0 | 3$^b$ |
| Azithromycin | 0 | 0 | 0 | 0 | 1 | 3$^b$ |
| *S. aureus* (10) | | | | | | |
| CEM-101 | 1 | 0 | 0 | 0 | 1 | 8 |
| Telithromycin | 0 | 0 | 0 | 0 | 0 | 10 |
| Clarithromycin | 0 | 0 | 0 | 0 | 0 | 6$^b$ |
| Azithromycin | 0 | 0 | 0 | 0 | 0 | 6$^b$ |
| Coagulase-neg. *staphylococci* (5) | | | | | | |
| CEM-101 | 1 | 1 | 0 | 3 | 0 | 0 |
| Telithromycin | 0 | 0 | 0 | 0 | 2 | 3 |
| Clarithromycin | 0 | 0 | 0 | 0 | 0 | 4$^b$ |
| Azithromycin | 0 | 0 | 0 | 0 | 0 | 4$^b$ |
| *Enterococcus* spp. (5) | | | | | | |
| CEM-101 | 0 | 0 | 0 | 0 | 0 | 5 |
| Telithromycin | 0 | 0 | 0 | 0 | 0 | 5 |
| Clarithromycin | 0 | 0 | 0 | 0 | 0 | 2$^b$ |
| Azithromycin | 0 | 0 | 0 | 0 | 0 | 2$^b$ |

$^a$Includes six isolates with a MIC of ≤0.008 µg/ml and a MBC of 0.015 µg/ml (off scale comparisons).
$^b$MBC was not evaluated on isolates with resistant level MIC results.

CEM-101 showed rapid bactericidal activity (reduction of ≥3 log 10 CFU/ml) against macrolide-susceptible strains of *S. aureus*, *S. epidermidis*, *S. pneumoniae*, *S. pyogenes* (only at 8× MIC) and viridans group streptococci, as well as a macrolide-resistant *S. pyogenes*. CEM-101 produced a greater reduction of CFU/ml and more rapid killing when compared to either TEL or the macrolides CLR and AZI.

| Summary of time kill curve results. | | |
|---|---|---|
| Organism | Antimicrobial agent | Antimicrobial activity |
| *S. aureus* (ATCC29213) | CEM-101 | Cidal at 2X, 4X, 8X |
| | Telithromycin | Cidal at 8X only |
| | Clarithromycin | Cidal at 8X only |
| | Azithromycin | Cidal at 8X only |
| *S. epidermidis* (095-2777A) | CEM-101 | Cidal at 2X, 4X, 8X |
| | Telithromycin | Static |
| | Clarithromycin | Static |
| | Azithromycin | Static |
| *E. faecalis* (ATCC 29212) | CEM-101 | Static |
| | Telithromycin | Static |
| | Clarithromycin | Static |
| | Azithromycin | Static |
| *S. pneumoniae* (ATCC 49619) | CEM-101 | Cidal at 2X, 4X, 8X |
| | Telithromycin | Cidal at 2X, 4X, 8X |
| | Clarithromycin | Cidal at 2X, 4X, 8X (slow killing) |
| | Azithromycin | Cidal at 2X, 4X, 8X (slow killing) |
| *S. pneumoniae* (075-241B) | CEM-101 | Static |
| | Telithromycin | Static |
| *S. pyogenes* (117-1612A) | CEM-101 | Cidal at 8X only |
| | Telithromycin | Cidal at 8X only (slow killing) |
| | Clarithromycin | Cidal at 8X only (slow killing) |
| | Azithromycin | Cidal at 8X only (slow killing) |
| *S. pyogenes* (088-11708A) | CEM-101 | Cidal at 2X, 4X, 8X |
| | Telithromycin | Cidal at 2X, 4X, 8X (slow killing) |
| *S. mitis* (112-1885A) | CEM-101 | Cidal at 2X, 4X, 8X |
| | Telithromycin | Cidal at 2X, 4X, 8X |
| | Clarithromycin | Cidal at 8X only (slow killing) |
| | Azithromycin | Cidal at 4X and 8X (slow killing) |

CEM-101 exhibited bactericidal activity when tested against macrolide-susceptible streptococci, CoNS and macrolide-resistant CLN-susceptible *S. pneumoniae*. CEM-101 MBC/MIC ratios can be high for *S. aureus*, but some strains showed MBC results remaining within the susceptible range of concentrations.

PAE testing: PAE values for CEM-101 and TEL were determined using established procedures which are consistent with those recommended by Craig and Gudmundsson. Both antimicrobial agents were tested against each isolate at 4× and 8× the MIC. Colony counts were performed at pre-antimicrobial exposure (T0) and after one or two hours post-antimicrobial exposure (T1 or T2). After "diluting out" the antimicrobial agents (1:1000), colony counts were performed every hour until turbidity was noted (up to 10 hours post dilution) to determine the length of PAE. The tested Gram-positive and Gram-negative pathogens were as follows: *S. aureus* ATCC 29213; *H. influenzae* ATCC 49247; *S. pneumoniae* ATCC 49619; *S. pyogenes* WT (177-1612A); and *M. catarrhalis* WT (117-10142A).

| PAE results for CEM-101 compared to TEL measured in hours. | | | | | |
|---|---|---|---|---|---|
| Antimicrobial concentration | *S. aureus* ATCC 29213 | *S. pneumoniae* ATCC 49619 | *S. pyogenes* 117-1612A | *H. influenzae* ATCC 49247 | *M. catarrhalis* 117-10142A |
| CEM-101 (4X MIC) | 2.3 | 3.0 | 6.1 | 3.2 | 6.3 |
| Telithromycin (4X MIC) | 2.6 | 1.9 | 3.4 | 1.2 | 4.0 |
| Exposure (hours) | 2 | 1 | 2 | 1 | 2 |

After two hours of exposure, the PAE of CEM-101 (2.3 hours) was similar to TEL (2.6 hours) when tested against *S. aureus* at 4× MIC value. By increasing the concentration during the exposure to 8× the MIC, CEM-101 PAE was extended to 3.9 hours (data not shown). CEM-101 PAE tested against *S. pneumoniae* and *S. pyogenes* was 3.0 and 6.1 hours compared to 1.9 and 3.4 hours, respectively for TEL. CEM-101 PAE against Gram-negative pathogens also favored the new agent versus the older ketolide.

The compounds described herein show a significant concentration and exposure-dependent PAE against Gram-positive, as evidenced by CEM-101 (average PAE, 3.8 hours) and Gram-negative (average PAE, 4.5 hours) pathogens commonly associated with CA-RTI and uSSSI. Overall, the PAE of CEM-101 was longer than that of TEL.

Example

Activity on *Chlamydia*. CEM-101, TEL, AZI, CLR, and doxycycline were provided as powders and solubilized according to the instructions of the manufacturers. Drug suspensions were made fresh each time the assay was run.

*C. pneumoniae*: Isolates of *C. pneumoniae* tested included a reference strain (TW 183), 9 isolates from children and adults with pneumonia from the United States (AR39, T2023, T2043, W6805, CWL 029, CM-1), an isolate from a child with pneumonia from Japan (J-21), and 2 strains from bronchoalveolar lavage specimens from patients with human immunodeficiency virus infection and pneumonia from the United States (BAL15 and BAL16).

*C. trachomatis*: 10 isolates of *C. trachomatis*, including standard isolates from the ATCC (E-BOUR, F-IC-CAL3, C-HAR32, J-UW-36, L2434, D-UW-57kx, B-HAR-36) and recent clinical isolates (N18(cervical), N19(cervical), 7015 (infant eye))

In vitro susceptibility testing: Susceptibility testing of *C. pneumoniae* and *C. trachomatis* was performed in cell culture using HEp-2 cells grown in 96-well microtiter plates. Each well was inoculated with 0.1 ml of the test strain diluted to yield $10^3$ to $10^4$ IFU/per ml, centrifuged at 1,700×g for 1 hr. and incubated at 35° C. for 1 hr. Wells were aspirated and overlaid with 0.2 mL of medium containing 1 µg of cycloheximide per mL and serial two-fold dilutions of the test drug. Duplicate plates were inoculated. After incubation at 35° C. for 48-72 hrs, cultures were fixed and stained for inclusions with fluorescein-conjugated antibody to the lipopolysaccharide genus antigen (Pathfinder, Kallestad Diagnostics, Chaska, Minn.). The minimal inhibitory concentration (MIC) is the lowest antibiotic concentration at which no inclusions were seen. The minimal bactericidal concentration (MBC) was determined by aspirating the antibiotic containing medium, washing wells twice with phosphate buffered saline and adding antibiotic-free medium. Cultures were frozen at −70° C., thawed, passed onto new cells, incubated for 72 hrs then fixed and stained as above. The MBC is the lowest antibiotic concentration that results in no inclusions after passage. All tests were run in triplicate.

Activities of CEM-101 and other antibiotics against 10 isolates of *C. pneumoniae*

| Drug | MIC (µg/ml) | | | MBC (µg/ml) | |
|---|---|---|---|---|---|
| | Range | 50% | 90% | Range | 90% |
| CEM 101 | 0.25-1.0 | 0.25 | 0.25 | 0.25-1.0 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

Activities of CEM-101 and other antibiotics against 10 isolates of *C. trachomatis*

| Drug | MIC (µg/ml) | | | MBC (µg/ml) | |
|---|---|---|---|---|---|
| | Range | 50% | 90% | Range | 90% |
| CEM 101 | 0.125-0.5 | 0.25 | 0.25 | 0.125-0.5 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

The results of this study demonstrated that CEM-101 has in vitro activity against *C. trachomatis* and *C. pneumoniae* comparable to other macrolides and ketolides.

Example

Tissue distribution. CEM-101 was well absorbed and distributed to the tissue. In the rat at 250 mg/kg/d, mean lung and liver concentrations of CEM-101 were 17 and 15-fold higher than in plasma. Lung and liver concentrations were 503 and 711-fold higher than plasma concentrations at the 200 mg/kg/d dose in monkeys. Concentrations of CEM-101 in the heart were significantly lower than levels found in lung or liver with levels 5 and 54-fold higher than plasma concentrations in rat and monkey, respectively.

Example

Activity of CEM-101 Against Invasive Isolates of *N. meningitidis* (NM) from a worldwide collection. Colonization of the nasopharynx (NP) by NM can lead to invasive meningococcal disease. Chemoprophylaxis is used to eradicate NP colonization and prevent transmission to nonimmune contacts. Described herein is the determination of the activity of CEM-101 tested against invasive clinical isolates of NM. 62 isolates (91.9% blood culture) of NM were collected from 29 medical centers in North and South America and Europe (1997-2008). Strains were tested for susceptibility (S) to CEM-101 and 10 comparators including β-lactams, fluoroquinolones (FQs), macrolides and three other classes by CLSI broth microdilution methods. Serological identification was performed for serogroups (SGs) B, C, Y and W135.

Susceptibility to penicillin was 82.3% with no resistant (R) strains detected. All isolates were susceptible to ceftriaxone, AZI, minocycline and rifampin. Isolates were susceptible to FQs (≤0.015 µg/ml); however, 13 strains had reduced susceptibility to nalidixic acid (MIC≥8 µg/ml), which may correlate with diminished susceptibility to FQs. Resistance to trimethoprim/sulfamethoxazole (T/S) was 59.7%. Among the MLS$_B$ class agents, CEM-101 was the most active (MIC$_{90}$, ≤0.015 µg/ml) compared to TEL (0.03 µg/ml), AZI and CLR (0.12 µg/ml) and erythromycin (0.25 µg/ml). The prevalence rates (%) of SGs were C (41.7), B (38.3), Y (16.7) and W135 (3.3). CEM-101 was the most active compound tested against MLS$_B$ NM strains (all MICs, ≤0.06 µg/ml) with a potency≥2- to 32-fold greater than other class agents. CEM-101 was active against NM isolates non-S to β-lactams and T/S.

| Antimicrobial agent | MIC (µg/ml) | | | % Susc.[a] | % Res.[a] |
| --- | --- | --- | --- | --- | --- |
| | 50% | 90% | Range | | |
| CEM-101 | ≤0.015 | ≤0.015 | ≤0.015-0.06 | —[b] | — |
| TEL | ≤0.015 | 0.03 | ≤0.015-0.12 | — | — |
| AZI | 0.06 | 0.12 | ≤0.015-0.12 | 100.0 | — |
| CLR | 0.03 | 0.12 | ≤0.015-0.25 | — | — |
| Erythromycin | 0.12 | 0.25 | 0.03-0.5 | — | — |
| Penicillin | 0.03 | 0.12 | ≤0.015-0.25 | 82.3 | 0.0 |
| Ceftriaxone | ≤0.015 | ≤0.015 | ≤0.015 | 100.0 | — |
| Ciprofloxacin | ≤0.008 | ≤0.008 | ≤0.008-0.015 | 100.0 | 0.0 |
| Levofloxacin | ≤0.008 | ≤0.008 | ≤0.008-0.015 | 100.0 | 0.0 |
| Minocycline | 0.12 | 0.12 | ≤0.008-0.25 | 100.0 | — |
| Rifampin | 0.015 | 0.06 | ≤0.008-0.12 | 100.0 | 0.0 |
| Trimethoprim/sulfamethoxazole | 0.5 | 2 | ≤0.06-4 | 37.1 | 59.7 |

[a]Susceptibility criteria based upon the CLSI (M100-S19, 2009).
[b]No susceptibility criteria have been proposed, but AZI at ≤2 µg/ml is considered susceptible.

Example

Ability of CEM-101 to Select Resistant *S. pyogenes* Clones by Multistep Method. It has been reported that *S. pyogenes* retain B-lactam susceptibility but are sometimes macrolide resistant. TEL is active against all macrolide resistant *S. pyogenes* genotypes except for erm(B). It has been discovered herein that CEM is 2 to 4-fold more active than TEL. Described herein is the tested capability of CEM, AZI, CLR, TEL, and CLN to select resistant clones of *S. pyogenes* in 5 strains with varying resistotypes.

One strain each was tested as follows: macrolide susceptible, erm(B), mef(A), erm(A), L4 ribosomal protein mutation. CLSI macrodilution was used for MIC tests. Serial passages were daily in MHB+5% lysed horse blood for each strain at subinhibitory drug concentrations, taking for each subsequent passage an inoculum from the tube 1-2 dilutions below the MIC that matched turbidity of a growth control. Daily passages were continued until the MIC increased>4-fold (max. 50 passages). Resistant clones were subcultured 10× in drug-free medium to test stability of selected resistance. Identity between parents and resistant clones was confirmed by PFGE and macrolide resistant phenotypes identified by PCR.

Parental MICs (µg/ml) were: CEM-101, 0.008-1; AZI, 0.06-4; CLR, 0.03-4; TEL, 0.03-8; and CLN, 0.06 (1 strain with AZI, CLR, CLN MICs>64 µg/ml was not tested). CEM-101 MICs increased after 18-43 days in ⅗ strains, rising from 0.03-1 µg/ml (parents)→0.25-8 µg/ml (resistant clones). MICs for 2 of the clones did not go above 0.25 µg/ml when passages were continued for the maximum 50 days. AZI had resistant clones after 5-35 days in ¾ strains tested, with MICs rising from 0.06-4 µg/ml (parents)→1→64 µg/ml (R clones). CLR had resistant clones after 6 days in ¼ strains tested, with MICs rising from 0.5 µg/ml (parent)→64 µg/ml (resistant clone). TEL had resistant clones after 6-22 days in ¾ strains tested, with MICs rising from 0.03-8 µg/ml (parents)→0.25→64 µg/ml (resistant clones.) CLN had resistant clones after 34-43 days in ⅔ strains tested with MICs rising from 0.06 µg/ml (parents)→0.5→64 µg/ml (resistant clones). In 2 of the 3 resistant clones with CEM-101 [parents erm(A), L4], MICs were 0.25 µg/ml and only in the 1 strain with erm(B) did CEM-101 MICs rise from 1-8 µg/ml.

Example

Capability of CEM-101 to Select for Resistant (R) Pneumococcal Clones by Multistep Method. Drug resistant strains of *S. pneumoniae* occur worldwide. It has been discovered herein that CEM-101 is 2 to 4-fold more active than TEL against macrolide resistant pneumococci. Described herein is the tested ability of CEM to select for resistant clones of *S. pneumoniae* compared to AZI, CLR, TEL, CLN in 8 pneumococcal strains with varying resistotypes.

One strain in each of the following was tested: macrolide susceptible, erm(B), mef(A), ermB+mefA, erm(A), L4, L22, and 23S rRNA ribosomal protein mutations. CLSI macrodilution was used for MIC testing. Serial passages were daily in MHB+5% lysed horse blood for each strain at subinhibitory drug concentrations, taking for each subsequent passage an inoculum from the tube 1-2 dilutions<MIC that matched turbidity of a growth control. Daily passages were continued until the MIC increased>4-fold (min. 14, max. 50 passages). Resistant clones were subcultured 10× in drug-free medium to test stability of selected resistance. Identity between parents and resistant clones was confirmed by PFGE and macrolide resistant phenotypes identified by PCR.

Parental MICs (µg/ml) were: CEM-101, 0.004-1; AZI, 0.03-8; CLA, 0.016-16; TEL, 0.004-0.5; CLI, 0.016-1 (four strains with AZI, 2 CLR, 2 CLN MICs>64 µg/ml were tested). CEM-101 MICs increased after 14-43 days in all 8 strains tested. For 7 strains, MICs rose from 0.004-0.03 µg/ml (parents)→0.06-0.5 µg/ml (resistant clones) in 14-43 days. For the eighth strain, containing erm(B)+mef(A), MICs rose from 1 µg/ml (parent)→32 µg/ml (resistant clone) in 18 days. AZI had resistant clones after 14-29 days in ¾ strains with MICs rising from 0.03-2 µg/ml (parents)→0.5→64 µg/ml (resistant clones). CLR had resistant clones after 14-49 days in ⅚ strains with MICs rising from 0.03-16 µg/ml (parents)→16→64 µg/ml (resistant clones). TEL had resistant clones after 14-38 days in ⅝ strains with MICs rising from 0.004-0.5 µg/ml (parents) to 0.06→64 µg/ml (resistant clones). CLN had resistant clones after 14-43 days in ⅖ strains with MICs rising from 0.03-0.06 µg/ml (parents)→0.25→64 µg/ml (resistant clones). CEM-101 yielded clones with higher MICs in all 8 strains, but 7 of 8 strains had clones with CEM-101 MICs≤0.5 μg/ml and only in the 1 strain with erm(B)+mef(A) with a parental MIC=1 μg/ml was a resistant clone with an MIC=32 μg/ml found.

Example

Human THP-1 macrophages were used. Accumulation was measured by microbiological assay. Intracellular activity was determined against phagocytized *S. aureus* (ATCC 25923; MICs: CEM-101, 0.125 mg/L; AZI, 0.5 mg/L) using a dose-response approach (AAC 2006; 50:841-51). Verapamil (100 μM) and gemfibrozil (250 μM) were used as inhibitors of P-glycoprotein and MRP, respectively (AAC, 2007; 51:2748-57).

Accumulations and activities after 24 h incubation, with and without efflux transporters inhibitors, are shown in the following Table, where Cc/Ce is the apparent cellular to extracellular concentration ratio, and $E_{max}$ is the maximal decrease of intracellular cfu compared to post-phagocytosis inoculum (calculated from non-linear regression [sigmoidal] of dose-effect response experiments).

extents in cells, but with a larger value (Cc/Ce) for CEM-101. In a second stage, whether CEM-101 is a substrate of Pgp or MRP efflux transporters was investigated FIG. 5 (panel B). Using a Pgp (verapamil) or MRPs inhibitor (gemfibrozil), no significant variations of the cellular accumulation of CEM-101 are observed while verapamil increases significantly the cellular accumulation of AZI.

Uptake of CEM-101 was linear over time, reaching accumulation levels about 375-fold within 24 h (AZI, 160×, CLR, 30×, TEL, 21×). Accumulation was suppressed by acid pH or addition of the proton ionophore monensin, but not modified by verapamil or gemfibrozil (preferential inhibitors of Pgp and MRP, respectively). Panel B shows that the accumulation of both CEM-101 and AZI was reduced when the experiments were conducted at acidic pH, with the change occurring almost entirely when the pH was brought from 7 to 6. Panel C shows that monensin, which is known to decrease the cellular accumulation of many weak organic bases, also almost completely suppressed the accumulation of both CEM-101 and AZI. In contrast, verapamil, an inhibitor of the P-glycoprotein

|  | AZI | | | CEM-101 | | |
|---|---|---|---|---|---|---|
|  |  | Intracellular activity ($\Delta$ log cfu at 24 h) | | | Intracellular activity ($\Delta$ log cfu at 24 h) | |
| Condition | Cc/Ce[1] (24 h) | Static dose (mg/L) | $E_{max}$[2] | Cc/Ce[1] (24 h) | Static dose (mg/L) | $E_{max}$[2] |
| control | 127.7 ± 23.5 | ~7.0 | 0.10 ± 0.09 | 268.1 ± 7.1 | ~0.02 | −0.85 ± 0.23 [b] |
| Verapamil | 216.37 ± 46.6 [a] | ~0.2 | −0.37 ± 0.15 | 290.2 ± 12.9 | ~0.03 | −0.59 ± 0.22 [b] |
| Gemfibrozil | 129.12 ± 2.69 | ~3.8 | −0.12 ± 0.20 | 308.2 ± 47.8 | ~0.03 | −0.73 ± 0.20 [b] |

[a] Statistically significant from both control and Gemfibrozil;
[b] not statistically significant.

Example

Intracellular activity of antibiotics. The determination of antibiotic activity against intraphagocytic *S. aureus* strain ATCC 25923 was determined. Full dose-responses studies were performed to assess the impact of active efflux in the modulation of the intracellular activity of CEM-101 and AZI against intraphagocytic *S. aureus* (strain ATCC 25923 [MICs: CEM-101, 0.125 mg/L; AZI, 0.5 mg/L]. Antibiotics were compared at 24 h for: (i) their relative static concentration (Cs), and (ii) their relative maximal efficacy (E). While verapamil (but not gemfibrozil) increases the intracellular activity of AZI, neither inhibitor have significant effect on the activity of CEM-101, suggesting that the latter, in contrast with AZI, is not a substrate of the corresponding eukaryotic transporters.

Example

Cellular accumulation of antibiotics. The cellular content in macrolides was measured in THP-1 macrophages by microbiological assay, using *S. aureus* ATCC 25923 as test organism. Cell proteins was assayed in parallel using the Folin-Ciocalteu/Biuret method. The cell associated content in macrolides was expressed by reference to the total cell protein content, and converted into apparent concentrations using a conversion factor of 5 μL per mg of cell protein (as commonly used for cultured cells).

Figure 5:
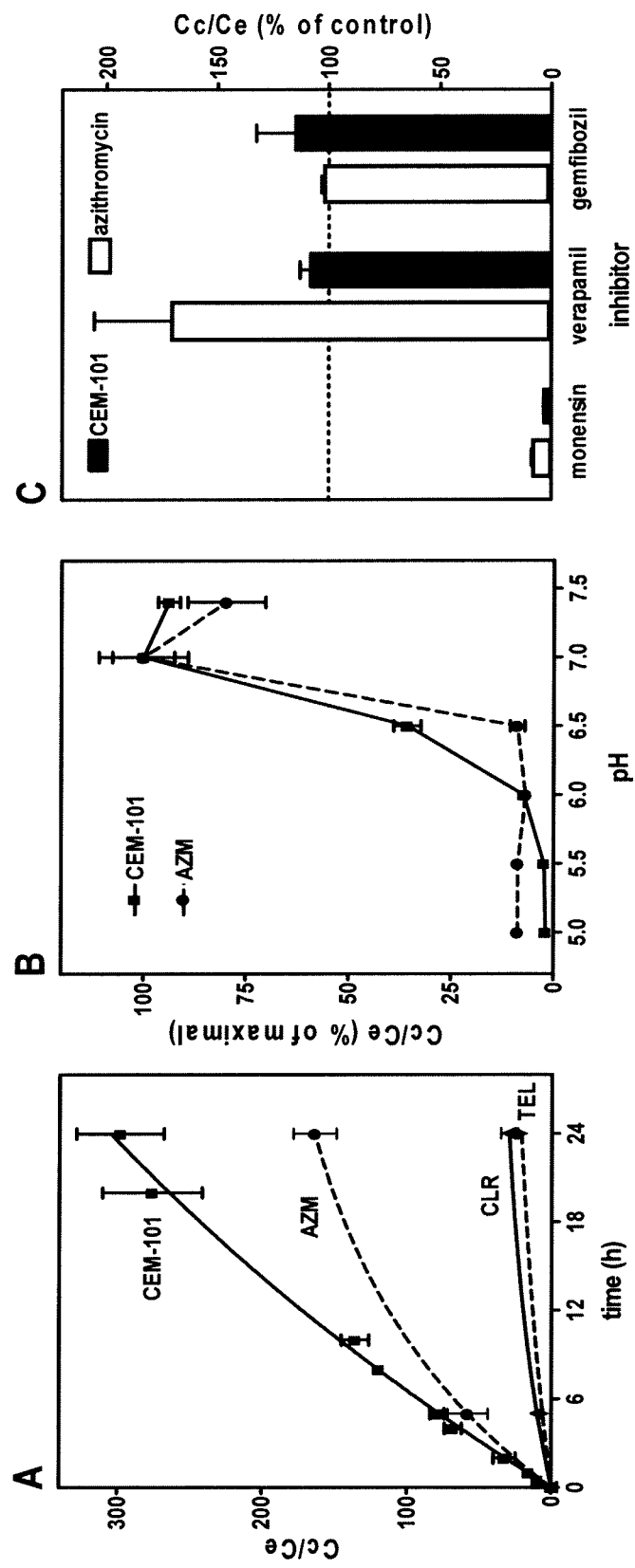
FIG. 5. Accumulation of CEM-101 versus comparators in THP-1 cells at 37° C. (all drugs at an extracellular concentration of 10 mg/liter). (A) Kinetics of accumulation (AZI); Cc, intracellular concentration; Ce, extracellular concentration); (B) influence of the pH of the culture medium on the accumulation (30 min) of CEM-101 (solid symbols and solid line) and AZI (open symbols and dotted line); (C) influence of monensin (50 μM; 2-h incubation), verapamil (150 μM; 24-h incubation), or gemfibrozil (250 μM; 24-h incubation) on the cellular accumulation of AZI and CEM-101. All values are means±standard deviations (SD) of three independent determinations (when not visible, SD bars are smaller than the symbols).

The cellular accumulation of CEM-101 in comparison with that of AZI in THP-1 cells was first measured FIG. 5 (panel A). At 24 h, both antibiotics concentrate to large efflux transporter (Pgp, also known as MDR1), increased the accumulation of AZI without affecting that of CEM-101, whereas gemfibrozil, an inhibitor of multidrug resistance proteins (MRP) and other organic anion transporters did not affect either compound. Neither verapamil nor gemfibrozil affected the accumulation of TEL or CLR (data not shown). The efflux of CEM-101 from cells incubated with 10 mg/L of CEM-101 for 1 h and then transferred into drug-free medium was examined. Efflux proceeded in a bimodal fashion, with half of the cell-associated drug being released within approximately 10 min, followed by a slower release phase of several hours (data not shown).

Example

Macrolides accumulate in eukaryotic cells and are considered advantageous for the treatment of intracellular infections. Ketolides are active against erythromycin-resistant organisms. The cellular accumulation and intracellular activity of CEM-101 towards the intracellular forms of *Staphylococcus aureus* (S. a.), *Listeria monocytogenes* (L. m.), and *Legionella pneumophila* (L. p.) in comparison with AZI, CLR, and TEL is shown in the following table.

|  | MIC[a] | Cs[b] | $E_{max}$[c] |
|---|---|---|---|
|  | CEM-101 | | |
| S.a. | 0.06 | 0.022 | −0.86 |
| L.m. | 0.004 | 0.11 | −0.66 |
| L.p. | 0.004 | 0.018 | −1.03 |

-continued

|  | MIC$^a$ | Cs$^b$ | E$_{max}$$^c$ |
|---|---|---|---|
| AZI | | | |
| S.a. | 0.5 | >50 | 0.04 |
| L.m. | 1 | 11.6 | −0.81 |
| L.p. | 0.016 | 2.90 | −0.83 |
| CLR | | | |
| S.a. | 0.5 | 0.84 | −0.18 |
| L.m. | | | |
| L.p. | 0.007 | 0.12 | −0.71 |
| TEL | | | |
| S.a. | 0.25 | 0.63 | −0.29 |
| L.m. | | | |
| L.p. | 0.007 | 0.06 | −0.63 |

$^a$mg/L;
$^b$static concentration (mg/L) at 24 h;
$^c$Δ log$_{10}$ CFU at 24 h compared to the post-phagocytosis inoculum Example MICs and extracellular activities of antibiotics were determined in MHB at both neutral and acidic pH. Intracellular activity was determined against *S. aureus* (ATCC 25923) phagocytosed by THP-1 macrophages as previously described (AAC, 2006, 50:841-851). Results were expressed as a change of efficacy compared to time 0 h.

| Conditions | CEM-101 | AZI | CLR | TEL |
|---|---|---|---|---|
| MICs (mg/L) | | | | |
| (i) pH 7.4 | 0.125 | 0.5 | 0.5 | 0.5 |
| (ii) pH 5.5 | 1-2 | 256 | 16 | 8 |
| Extracellular activity (24 h): Δ log cfu from time 0 h | | | | |
| (i) Broth pH 7.4 | | | | |
| Emax$^1$ | −1.4 ± 0.1 | −1.2 ± 0.6 | −1.4 ± 0.2 | −1.0 ± 0.4 |
| Static dose$^2$ | ~0.06 | ~3.63 | ~1.41 | ~0.28 |
| R$^2$ | 0.964 | 0.860 | 0.965 | 0.868 |
| (ii) Broth pH 5.5 | | | | |
| Emax$^1$ | −1.6 ± 0.4 | +2.1 ± 0.1 | −1.5 ± 0.8 | −1.4 ± 0.9 |
| Static dose$^2$ | ~1.48 | / | ~10.47 | ~9.33 |
| R$^2$ | 0.915 | / | 0.911 | 0.879 |
| Intracellular activity (24 h): Δ log cfu from time 0 h | | | | |
| Emax$^1$ | −0.8 ± 0.2 | 0.10 ± 0.0 | −0.1 ± 0.1 | −0.4 ± 0.2 |
| Static dose$^2$ | ~0.02 | ~7.8 | ~0.98 | ~0.23 |
| R$^2$ | 0.906 | 0.980 | 0.974 | 0.935 |
| THP-1 | | | | |
| Emax$^1$ | −0.8 ± 0.2 | 0.1 ± 0.1 | −0.1 ± 0.1 | −0.4 ± 0.1 |
| Static dose$^2$ | ~0.02 | ~10 | ~0.98 | ~0.28 |

$^1$Maximal decrease of intracellular cfu compared to initial, post-phagocytosis inoculum (calculated from non-linear regression [sigmoidal] of dose-effect response) run in broth (extracell.) or with infected macrophages (intracell.)
$^2$Extracellular concentration (Cs in mg/L) yielding an apparent static effect. Comparative pharmacological descriptors (Emax and static concentrations [Cs]) obtained from the dose-responses studies. Dose-response studies in Mueller-Hinton broth. Against *S. aureus* ATCC 25923 and in broth, at pH 7.4, CEM-101 is systematically more active than AZI, CLR and TEL; at pH 5.5, AZI, CLR and TEL show significant decrease of their potencies, while CEM-101 shows less change.

Compared to AZI, CLR and TEL, CEM-101 activity was less affected by acidic pH of the broth and showed greater potency (lower static dose) and larger maximal efficacy (Emax) against intracellular *S. aureus*.

Example

Cell lines. Experiments were performed with THP-1 cells (ATCC TIB-202; American Tissue Culture Collection, Manassas, Va.), a human myelomonocytic cell line displaying macrophage-like activity (see, e.g., Barcia-Macay et al., Antimicrob. Agents Chemother. 50:841-851 (2006)). Assay of the cell-associated macrolides and calculation of the apparent cellular-to-extracellular-concentration ratios. Macrolides were assayed by a microbiological method, using *S. aureus* ATCC 25923 as a test organism. Cell proteins were measured in parallel using the Folin-Ciocalteu/biuret method. The cell-associated contents in macrolides were expressed by reference to the total cell protein content and converted into apparent concentrations using a conversion factor of 5 μL per mg of cell protein, an average value found for many cultured cells.

Bacterial strains, susceptibility testing, and 24-h dose-response curve studies with broth. *S. aureus* ATCC 25923 (methicillin [meticillin] sensitive), *L. monocytogenes* strain EGD, and *L. pneumophila* strain ATCC 33153 were used in the present study. MIC determinations were performed in Mueller-Hinton broth (for *S. aureus*) and tryptic soy broth (for *L. monocytogenes*) after a 24-h incubation, or in α-ketoglutarate-buffered yeast extract broth (for *L. pneumophila*) after a 48-h incubation. For *S. aureus* studies, 24-h concentration-response experiments in acellular medium were performed in Mueller-Hinton broth.

Cell infection and assessment of antibiotic intracellular activities. Infection of THP-1 cells and assessment of the intracellular activity of antibiotics were performed using conventional methods for *S. aureus* and *L. monocytogenes* or with minor adaptations for *L. pneumophila* using (i) a multiplicity of infection of 10 bacteria per macrophage and (ii) gentamicin (50 mg/liter) for 30 to 45 min for the elimination of nonphagocytosed bacteria.

Statistical analyses. Curve-fitting statistical analyses were performed with GraphPad Prism version 4.03 and GraphPad Instat version 3.06 (GraphPad Software, San Diego, Calif.).

Example

Susceptibility toward *S. aureus* ATCC 25923, *Listeria monocytogenes* EGD, and *Legionella pneumophila* ATCC 33153. CEM-101 showed lower MICs than AZI against the three selected organisms (*S. aureus*, 0.06 and 0.5 mg/liter; *L. monocytogenes*, 0.004 and 1 mg/liter; and *L. pneumophila*, 0.004 and 0.016 mg/liter) in conventional susceptibility testing. The MICs of CEM-101, TEL, AZI, and CLR against *S. aureus* and *L. monocytogenes* were measured in broths adjusted to pH values ranging from 5.5 to 7.4. The range was selected to cover the values at which the antibiotics could be exposed in the extracellular milieu or intracellularly for the two organisms considered. As illustrated in FIG. 1, all four drugs showed a marked decrease in potency against both organisms when the pH was decreased from 7.4 to 5.5, with AZI demonstrating the most significant loss of activity. CEM-101 retained the most activity, consistently showing the lowest MICs throughout the entire pH range investigated, with values (mg/liter) ranging from 0.06 (pH 7.4) to 0.5 (pH 5.5) for *S. aureus* (ATCC 25923) and 0.0039 (pH 7.4) to 0.25 (pH 5.5) for *L. monocytogenes* (EDG). For *L. pneumophila* (data not shown), the MIC of CEM-101 increased from 0.005 to 0.01 and that of AZI from approximately 0.01 to 0.25 mg/liter when the pH of the broth was decreased from 7.4 to 6.5 (no determination could be made at lower pH values because of absence of growth).

Example 5

Figure 3:
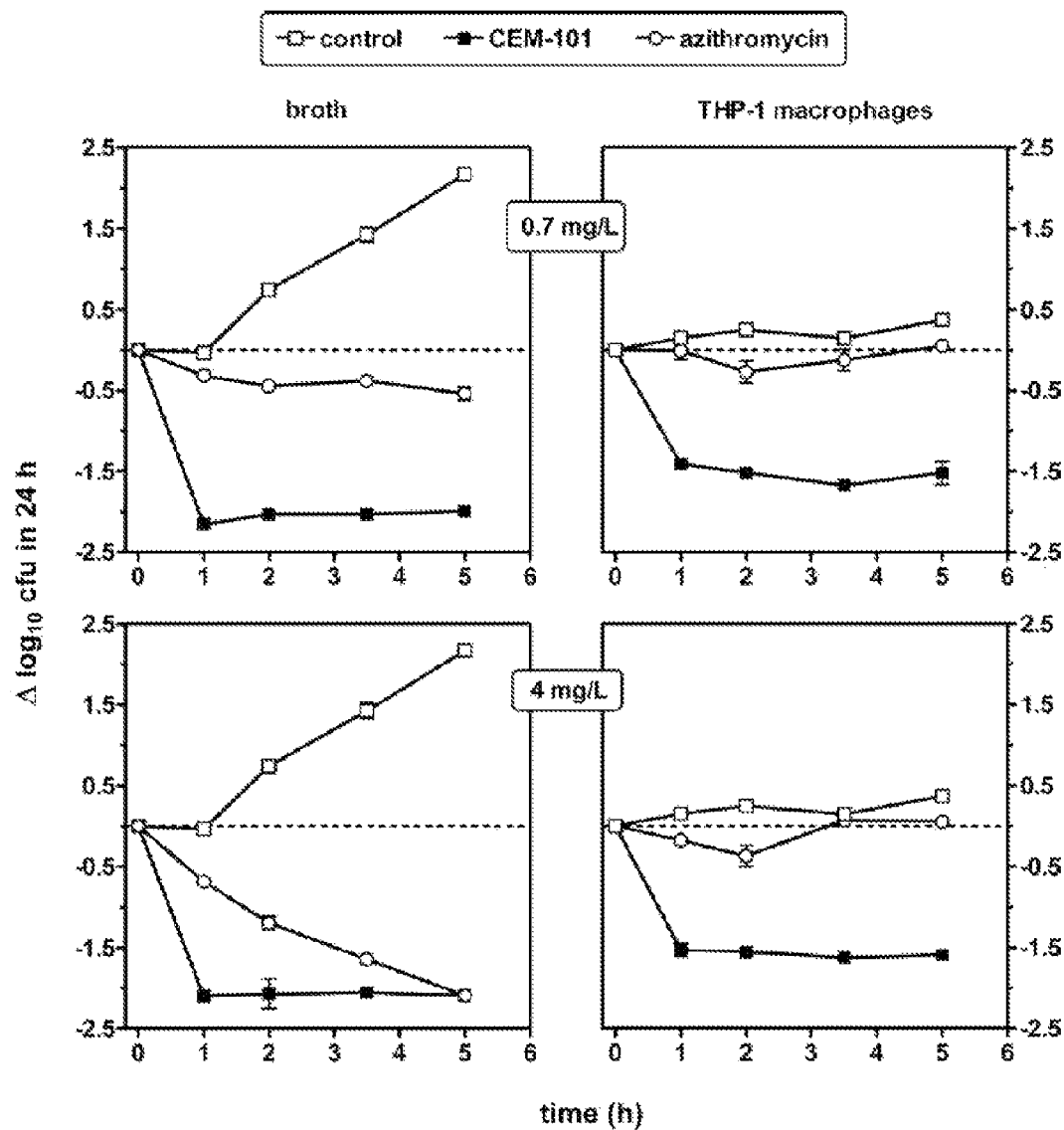
FIG. 3. Concentration-effect relationships for CEM-101, TEL, CLR, and AZI toward *S. aureus* (ATCC 25923) in broth (left panels) and after phagocytosis by THP-1 macrophages (right panels). The ordinate shows the change in CFU (Δ log CFU) per ml (broth) or per mg of cell protein (THP-1 macrophages) at 24 h compared to the initial inoculum. The abscissa shows the concentrations of the antibiotics as follows: (i) top panels, weight concentrations (in mg/liter) in broth (left) or in the culture medium (right) and (ii) bottom panels, multiples of the MIC as determined in broth at pH 7.4. All values are means±standard deviations (SD) of three independent experiments (when not visible, SD bars are smaller than the symbols). Statistical analysis based on global analysis of curve-fitting parameters (one-way analysis of variance); the only significant difference is between CEM-101 and AZI in broth (P=0.04). Numerical values of the pertinent pharmacological descriptors and statistical analysis of their differences are shown in Table 1.

Time and concentration effects against extracellular and intraphagocytic *S. aureus*. Short-term (6-h) time-kill curves were obtained for CEM-101 in comparison with those for AZI against *S. aureus* (ATCC 25923) in broth and after phagocytosis by THP-1 macrophages using two single fixed concentrations of 0.7 and 4 mg/liter. The lower concentration was chosen to be relevant to the serum concentration of AZI and CEM-101, and the higher concentration was selected to be above the MIC of AZI for the organisms of interest. Results presented in FIG. 3 show that under these conditions, only CEM-101 was able to significantly decrease CFU in broth as well as in THP-1 macrophages at the 0.7-mg/liter concentration. At the 4-mg/liter concentration in broth, AZI eventually achieved the same antibacterial effect as CEM-101, but at a lower rate (5 h compared to 1 h). In THP-1 macrophages, no consistent activity was detected for AZI, even at the 4-mg/liter concentration, whereas CEM-101 again achieved a reduction of approximately 1.5 log 10 CFU, similar to the magnitude seen at the 0.7-mg/liter concentration. In all situations with CEM-101, the maximal decrease of CFU was obtained within 1 h and was maintained thereafter.

Figure 2:
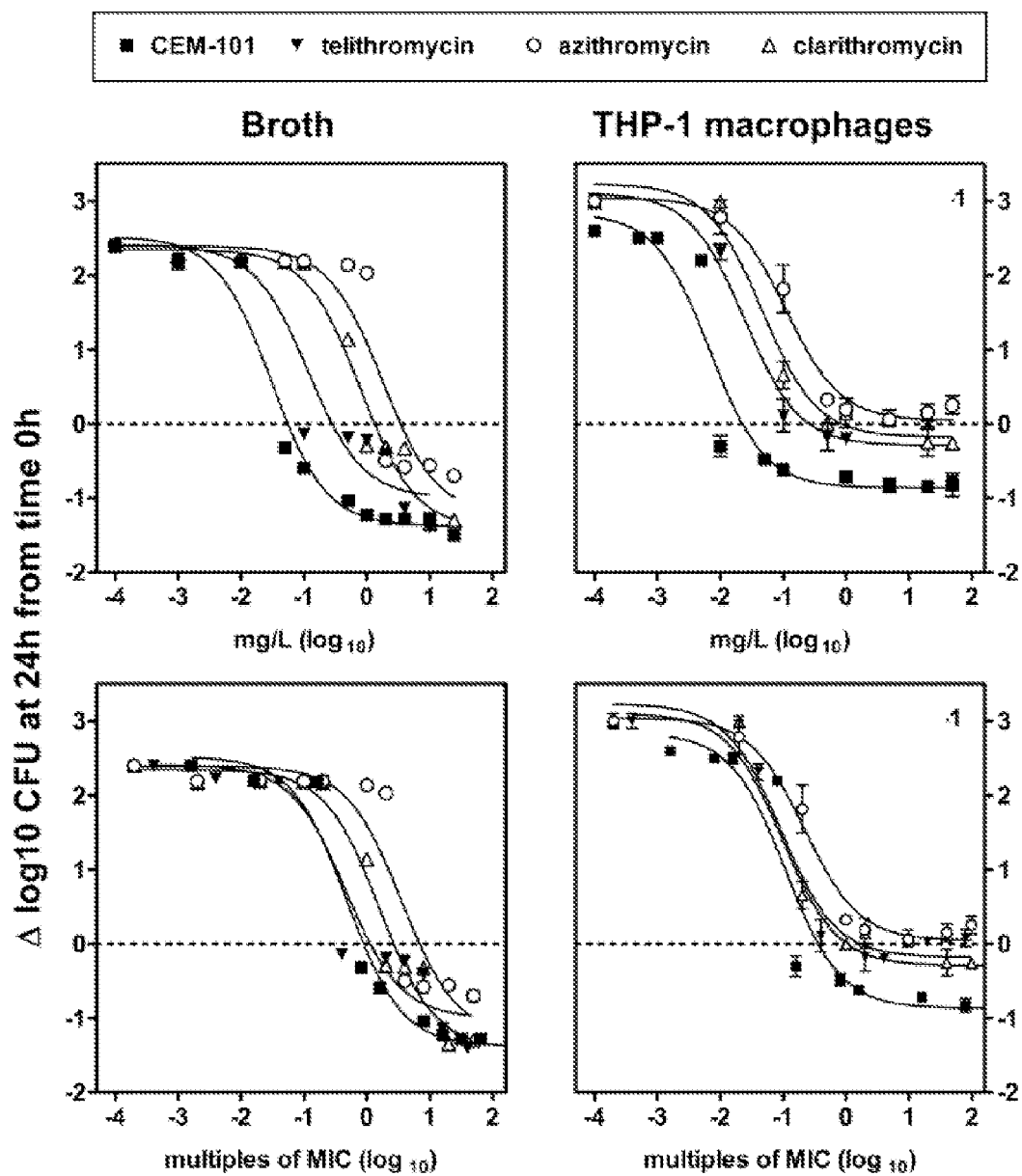
FIG. 2. Short-term time-kill effect of CEM-101 and AZI on *S. aureus* (ATCC 25923) in broth (left panels; pH 7.4) or after phagocytosis by THP-1 macrophages (right panels). Both drugs were used at an extracellular concentration of either 0.7 (top panels) or 4 (bottom panels) mg/liter. MICs of CEM-101 and AZI were 0.06 and 0.5 mg/liter, respectively. All values are means±standard deviations (SD) of three independent experiments (when not visible, SD bars are smaller than the symbols).

We then performed concentration-response experiments at a fixed time point (24 h) to obtain the pertinent pharmacological descriptors of CEM-101 activity (relative potency [50% effective concentration $\{EC_{50}\}$], apparent static concentration $[C_s]$, and relative maximal efficacy $[E_{max}]$ in comparison with CLR, AZI and TEL activity (additional details are described in Barcia-Macay et al., Pharmacodynamic evaluation of the intracellular activities of antibiotics against *Staphylococcus aureus* in a model of THP-1 macrophages Antimicrob. Agents Chemother. 50:841-851 (2006)). Data are presented in FIG. 2 as a function of (i) weight concentrations (mg/liter) and (ii) multiples of the MICs (as determined in broth at pH 7.4). The numerical values of the corresponding pharmacological descriptors are shown in the Table. Pertinent regression parameters[a] (with confidence intervals [CI]), and statistical analysis of the dose-response curves illustrated in FIG. 2.

| antibiotic | $E_{max}$[♦] (CI) | | $EC_{50}$[◊] (CI) | $C_s$[◊◊] | $R^2$ |
|---|---|---|---|---|---|
| broth[+] | | | | | |
| CEM-101 | −1.37 (−1.67 to −1.08) a; A | mg/L | 0.03 (0.02 to 0.06) a; A | 0.06 | 0.973 |
| | | x MIC | 0.48 (0.26 to 0.91) a; A | 0.88 | |
| TEL | −1.00 (−1.78 to −0.22) a; A | mg/L | 0.12 (0.03 to 0.52) b; A | 0.29 | 0.892 |
| | | x MIC | 0.46 (0.11 to 2.06) a; A | 0.96 | |
| AZI | −1.23 (−2.55 to 0.083) a; A | mg/L | 1.78 (0.45 to 7.02) c; A | 3.4 | 0.872 |
| | | x MIC | 3.55 (0.90 to 14.0) b; A | 6.87 | |
| CLR | −1.41 (−1.95 to −0.87) a; A | mg/L | 0.80 (0.41 to 1.56) c; A | 1.32 | 0.956 |
| | | x MIC | 1.59 (0.81 to 3.1) a, b; A | 2.65 | |

| antibiotic | $E_{max}$[♦] (CI) | | $EC_{50}$[◊] (CI) | $C_s$[◊◊] | $R^2$ (CI) |
|---|---|---|---|---|---|
| THP-1 macrophages[++] | | | | | |
| CEM-101 | −0.86 (−1.36 to −0.37) a; B | mg/L | 0.0068 (0.0023 to 0.020) a; B | 0.022 | 0.927 |
| | | x MIC | 0.11 (0.037 to 0.32) a; B | 0.35 | |
| TEL | −0.29 (−0.70 to 0.12) b; B | mg/L | 0.024 (0.007 to 0.088) b; B | 0.63 | 0.954 |
| | | x MIC | 0.097 0.027 to 0.35 a; B | 1.04 | |
| AZI | 0.04 (−0.23 to 0.32) b; B | mg/L | 0.11 (0.05 to 0.22) c; B | >50 | 0.983 |
| | | x MIC | 0.22 0.11 to 0.45 a; B | >100 | |

| | -continued | | | | |
|---|---|---|---|---|---|
| CLR | −0.18 (−0.52 to 0.16) b; B | mg/L | 0.046 (0.018 to 0.12) b, c; B | 0.84 | 0.974 |
| | | x MIC | 0.093 0.035 to 0.25 a; B | 1.68 | |

Figure 4:
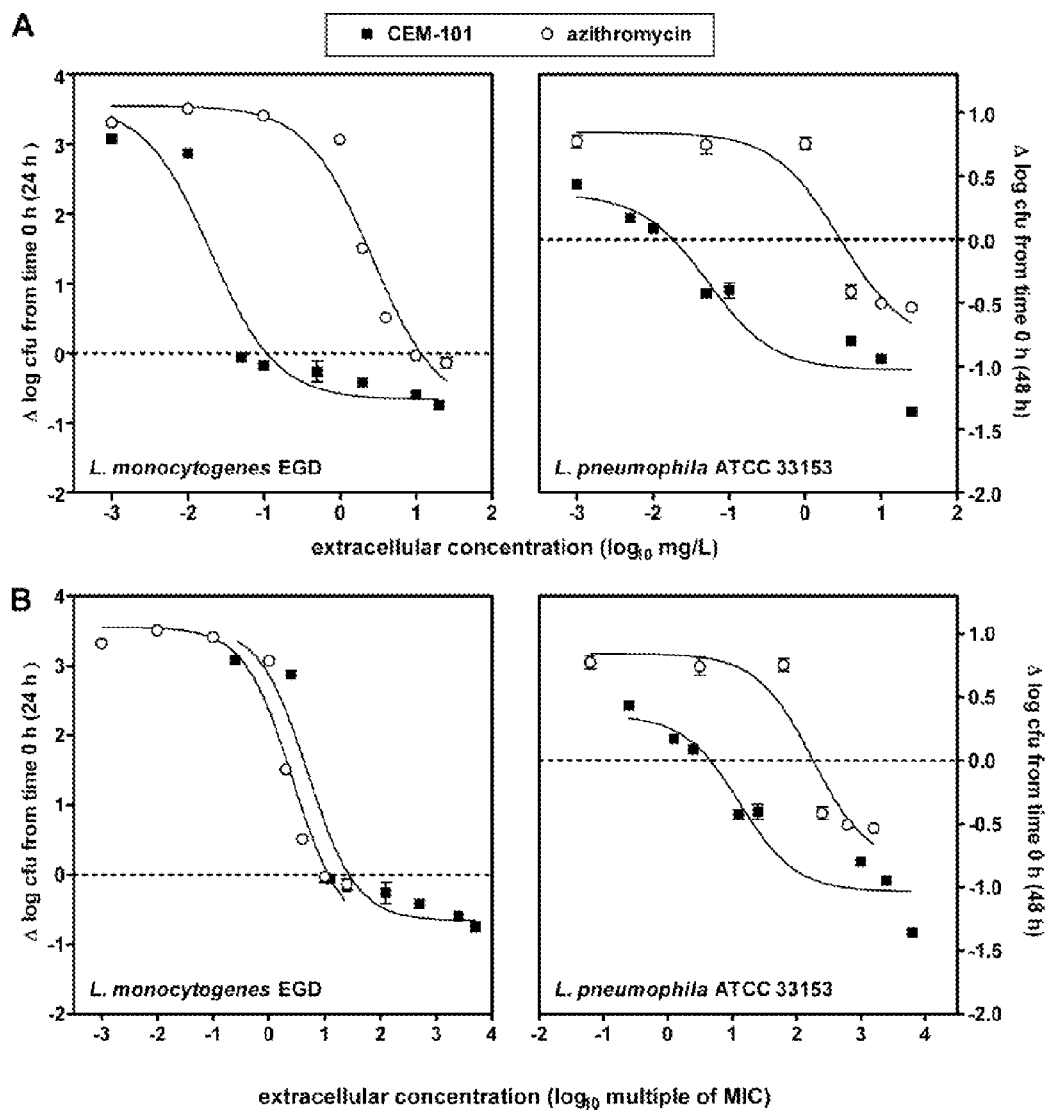
FIG. 4. Concentration-effect relationships for CEM-101 and AZI toward intraphagocytic *L. monocytogenes* (strain EGD, left panels) and *L. pneumophila* (strain ATCC 33153, right panels). The ordinate shows the change in CFU (Δ log CFU) per mg of cell protein at 24 h (*L. monocytogenes*) or 48 h (*L. pneumophila*) compared to the initial postphagocytosis inoculum. The abscissa shows the concentrations of the antibiotics as follows: (i) top panels, weight concentrations (in mg/liter); (ii) bottom panels, multiples of the MIC as determined in broth at pH 7.4. All values are means±standard deviations (SD) of three independent experiments (when not visible, SD bars are smaller than the symbols).

[a] using all data points shown in FIG. 4 (data from samples without antibiotic when the extracellular concentration of an antibiotic is lower than 0.01 x MIC (5)
[+] original inoculum [time = 0 h]: 0.97 ± 0.24 × $10^6$ CFU/mL (n = 3)
[++] original (post-phagocytosis) inoculum [time = 0 h]: 2.74 ± 0.55 × $10^6$ CFU/mg protein (n = 3)
[♦] CFU decrease (in $\log_{10}$ units) at time = 24 h from the corresponding original inoculum, as extrapolated for antibiotic concentration = ∞; samples yielding less than 5 counts were considered below detection level.
[◊] concentration (in mg/L or in x MIC) causing a reduction of the inoculum half-way between initial ($E_0$) and maximal ($E_{max}$) values, as obtained from the Hill equation (using a slope factor of 1);
[◊◊] concentration (in mg/L or in x MIC) resulting in no apparent bacterial growth (number of CFU identical to the original inoculum), as determined by graphical intrapolation; Statistical Analyses. Analysis of the differences between antibiotics (per column for the corresponding rows; one-way ANOVA with Tuckey test for multiple comparisons between each parameter for all drugs): figures with different lower case letters are significantly different from each other ($p < 0.05$). Analysis of the differences between broth and THP-1 macrophages (per row for the corresponding columns; unpaired, two-tailed t-test): figures with different upper case letters are significantly different from each other ($p < 0.05$).

The activities in both broth and THP-1 macrophages developed in a concentration-dependent fashion, as denoted by the sigmoidal shape of each best-fit function (Hill equation). In broth, the relative efficacy of CEM-101 ($E_{max}$ of −1.37 $\log_{10}$) was similar to that of the other drugs ($E_{max}$ values of −1.00 to −1.41 $\log_{10}$). In THP-1 macrophages, the relative efficacy of CEM-101 was significantly decreased compared to that in broth ($E_{max}$ of −0.86 $\log_{10}$), but not to the same extent as those of the other drugs, which essentially became bacteriostatic only ($E_{max}$ values of 0.04 to −0.29 $\log_{10}$). On a weight basis, CEM-101 had higher relative potencies (lower $E_{50}$ values) and lower static concentrations (lower $C_s$ values) than all three comparator drugs in both broth and in THP-1 macrophages. When the data were analyzed as a function of equipotent concentration (multiples of the MIC), these differences in $EC_{50}$ values were reduced, indicating that the MIC was the main driving parameter in this context. In broth, even when analyzed as multiples of the MIC, CEM-101 and CLR still showed significantly lower $EC_{50}$s than TEL and AZI.

Example

Activity against intraphagoctic *L. monocytogenes* and *L. pneumophila*. The same approach was used as that for *S. aureus* to assess the activities of CEM-101 and AZI against phagocytized *L. monocytogenes* and *L. pneumophila* to obtain information on concentration-effect relationships and on the corresponding pertinent pharmacological descriptors. As shown in FIG. 4, a relationship compatible with the Hill equation was observed in all cases, although the limited growth of *L. pneumophila* made the fitting of functions somewhat more uncertain. When the data were plotted against weight concentration, it appeared that CEM-101 had a higher relative potency (lower EC50) than AZI for both *L. monocytogenes* and *L. pneumophila*. This difference was reduced but nevertheless remained significant when data for *L. pneumophila* were plotted against multiples of the MIC, indicating that the MIC was an important but not the exclusive driver of intracellular activity against this organism. Conversely, no difference in the responses was seen for *L. monocytogenes* when data were expressed as multiples of the MIC. Numerical values of the pertinent pharmacological descriptors and statistical analysis of their differences are shown in the Table.

Pertinent regression parameters[a] (with confidence intervals [CI]), and statistical analysis of the dose-response curves illustrated in FIG. 4.

| *L. monocytogenes* EGD+ | | | | | |
|---|---|---|---|---|---|
| anti-biotic | $E^{max}$[♦] (CI) | | $EC_{50}$[◊] (CI) | $C_S$[◊◊] | $R^2$ |
| CEM-101 | −0.66 (−1.28 to −0.037) a | mg/L | 0.020 (0.005 to 0.073) a | 0.11 | 0.934 |
| | | x MIC | 5.00 (1.36 to 18.5) a | 0.88 | |
| AZI | −0.81 (−2.11 to 0.48) a | mg/L | 2.66 (0.91 to 7.73) b | 11.6 | 0.953 |
| | | x MIC | 2.66 (0.81 to 3.1) a | 11.6 | |

| *L. pneumophila* ATCC 33153++ | | | | | |
|---|---|---|---|---|---|
| anti-biotic | $E_{max}$[♦] (CI) | | $EC_{50}$[◊] (CI) | $C_S$[◊◊] | $R^2$ |
| CEM-101 | −1.03 (−1.34 to −0.72) a | mg/L | 0.052 (0.012 to 0.23) a | 0.018 | 0.920 |
| | | x MIC | 13.1 (3.02 to 57.0) a | 4.56 | |
| AZI | −0.83 (−2.00 to 0.34) a | mg/L | 2.86 (0.17 to 48.6) b | 2.90 | 0.903 |
| | | x MIC | 179.0 (10.5 to 3038) b | 181 | |

[a] using all data points shown in FIG. 4 (data from samples without antibiotics were not used because of evidence of extracellular growth when the extracellular concentration of an antibiotic is lower than 0.01 x MIC (5).
[+] original (post-phagocytosis) inoculum [time = O h; CFU/mg protein]): *L. monocytogenes*, 1.67 ± 0.22 × $10^6$ (n = 3); *L. pneumophila*, 0.94 ± 0.60 × $10^6$.
[♦] CFU decrease (in logo units) at time = 24 h (*L. monocytogenes*) or 48 h (*L. pneumophila*) from the corresponding original inoculum, as extrapolated for antibiotic concentration ∞; samples yielding less than 5 counts were considered below detection level.
[◊] concentration (in mg/L or in x MIC) causing a reduction of the inoculum half-way between initial ($E_0$) and maximal ($E_{max}$) values, as obtained from the Hill equation (using a slope factor of 1).
[◊◊] concentration (in mg/L or in x MIC) resulting in no apparent bacterial growth (number of CFU identical to the original inoculum), as determined by graphical intrapolation. Statistical analyses: analysis of the differences between the two antibiotics (per column for the corresponding rows; unpaired, two-tailed t-test): figures with different lower case letters are significantly different from each other ($p < 0.05$).

Example

Dose-response studies in infected THP-1 macrophages Against intraphagocytic *S. aureus* ATCC 25923, CEM-101 is more potent than AZI, CLR and TEL (lower Cs), In addition, CEM-101 is able to reduce the intracellular inoculum ($E_{max}$ ~1 log), which is not observed with any of AZI, CLR and TEL.

| CEM-101 uptake within cells (ii): role of the cell type | | | | |
|---|---|---|---|---|
| Cells | THP-1 (human macrophages) | J774 (murine macrophages) | MDCK (canine epith. cells) | MDCK sur-expressing the MDR1 efflux transporters |
| Cc/Ce at 5 h | ~50-150 | ~60 | ~45 | ~30 |

Example

Figure 7:
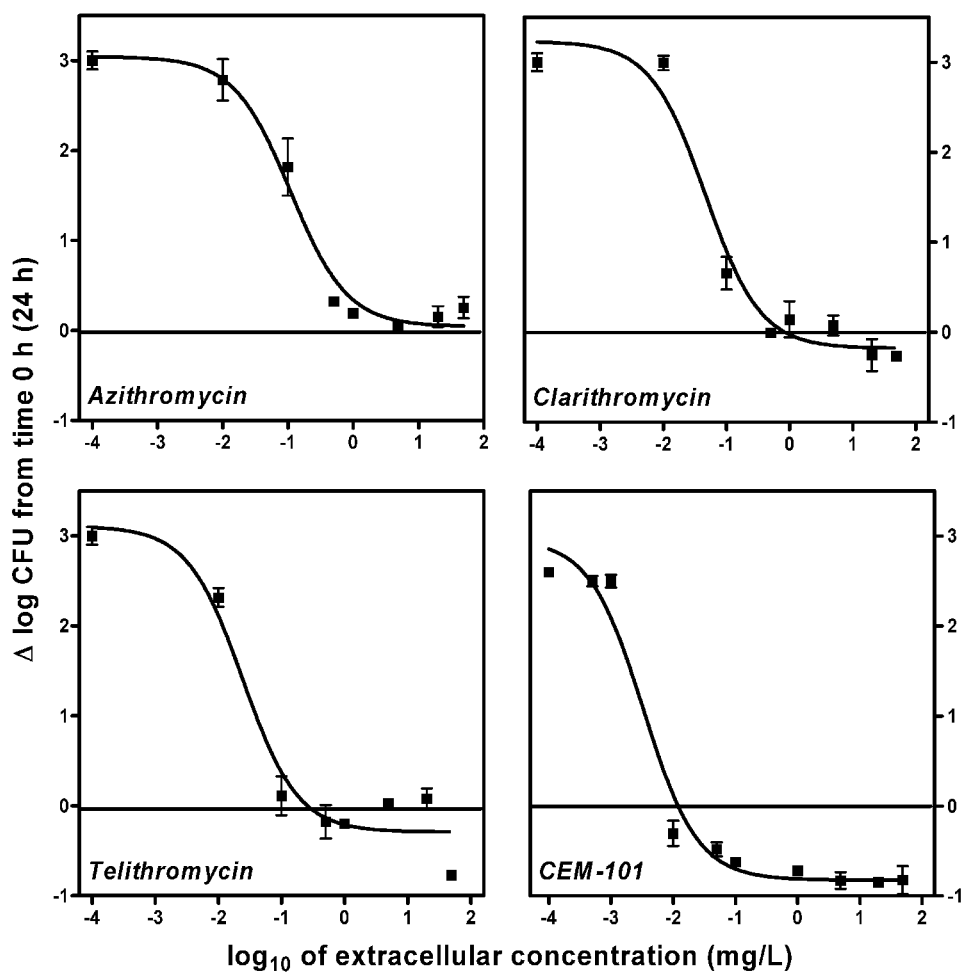
FIG. 7. Intracellular Activity of CEM-101 compared to AZI, CLR, and TEL, expressed as a dose response curve of Δ log CFU from time 0 to 24 hours versus log dose.

Example Dose-response studies of CEM-101 vs. comparators (AZI, CLR and TEL) against intracellular *S. aureus* ATCC 25923 (THP-1 macrophages). See FIG. 7 and the Table.

|  | CEM-101 | AZI | CLR | TEL |
|---|---|---|---|---|
| Emax | −0.80 ± 0.11 | 0.04 ± 0.11 | −0.18 ± 0.13 | −0.29 ± 0.16 |
| Cs (mg/L) | ~0.01 | >50 | ~0.86 | ~0.27 |

Example

Figure 6:
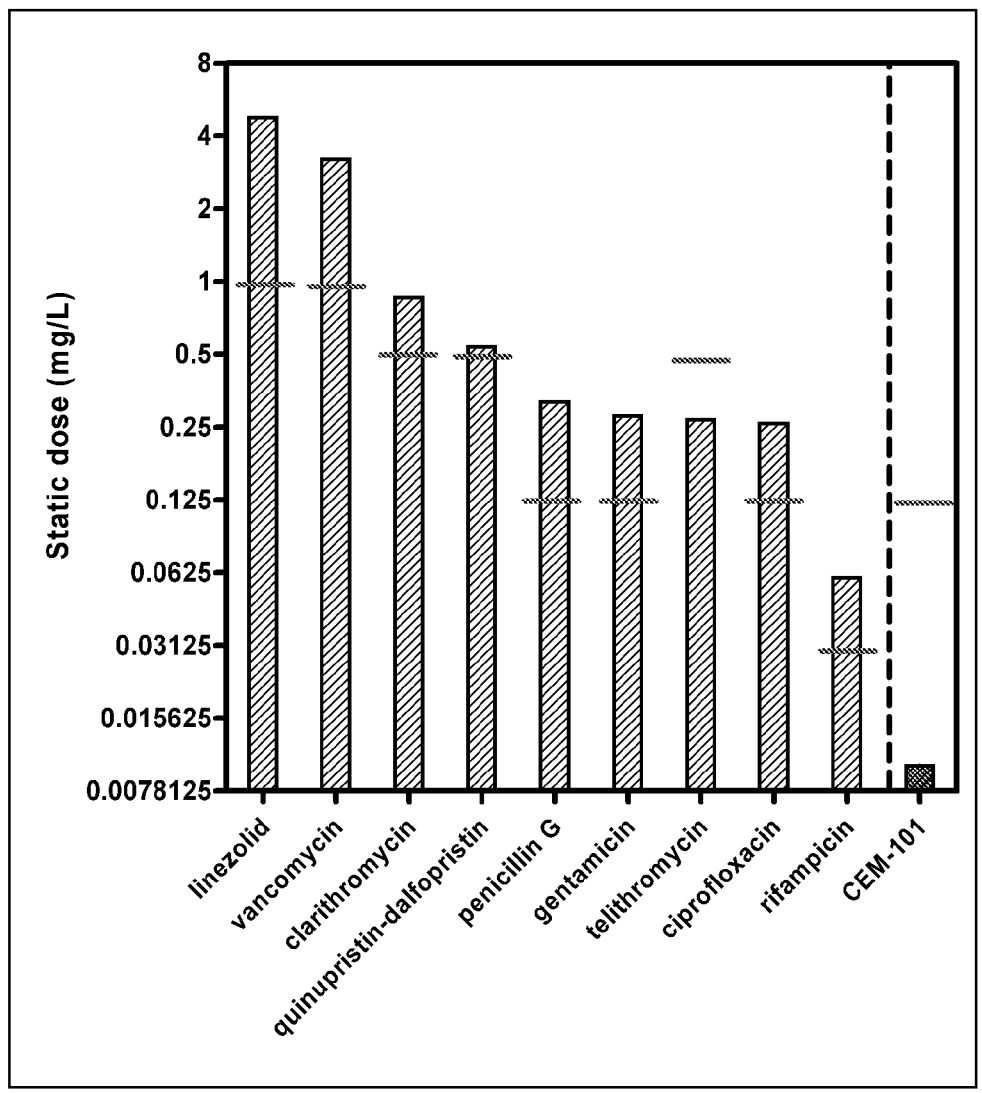
FIG. 6. Intracellular activity: comparative studies with other anti-staphylococcal agents. Comparative dose-static response of antibiotics against intracellular *Staphylococcus aureus* (strain ATCC 25923) in THP-1 macrophages. Bars represent the MICs (in mg/L) or the extracellular static dose.

Intracellular activity: comparative studies with other anti-staphylococcal agents. Comparative dose-static response of antibiotics against intracellular Staphylococcus aureus (strain ATCC 25923) in THP-1 macrophages were measured. See FIG. 6 bars represent the MICs (in mg/L) or the extracellular static dose.

METHOD. Mouse peritoneal macrophages were infected with viable *M. leprae*, the drugs are added and incubated at 33° C. for 3 days. After 3 days macrophages were lysed to release the intracellular *M. leprae* which were then assayed for viability by radiorespirometry and viability staining. CEM-101 shows efficacy against intracellular *M. leprae* viability.

The Thai-53 isolate of *M. leprae*, maintained by serial passages in athymic nu/nu mice footpads, was used for all experiments. For axenic testing freshly harvested viable *M. leprae* were incubated in medium along with different concentrations of the drugs (CEM-101, CLR and rifampin) for 7 days at 33° C. At the end of this incubation drug-treated *M. leprae* were subjected to radiorespirometry to assess viability based on oxidation of palmitate and staining with viability dyes to assess the extent of membrane damage. For intracellular testing peritoneal macrophages from Swiss mice were infected with freshly harvested viable *M. leprae* at an MOI of 20:1 for 12 hours. At the end of the infection extracellular bacteria were washed and drugs added at different concentrations and incubated for 3 days at 33° C. At the end of 3 days cells were lysed to obtain the intracellular *M. leprae* for radiorespirometry and viability staining.

CEM-101 at 0.15 μg/ml was able to significantly ($P<0.001$) reduce the viability of *M. leprae* in both axenic and intracellular cultures when compared to controls. Inhibition by CEM-101 was not statistically different from inhibition obtained with CLR under identical conditions and at the same concentration.

Example

Emerging Telithromycin-Resistant β-Haemolytic Streptococci (BHS). CEM-101 was tested against a collection of 43 TEL-R BHS. A total of 53 (1.3%) BHS were identified among 3,958 in the SENTRY Antimicrobial Surveillance Program (2003-2006) that were TEL-R (MIC, ≥2 μg/ml). 43 strains (36 group A, 1 group C, 6 group G) were available for testing, from 20 hospitals in Europe (31 strains), North America (11) and Latin America (1). Susceptibility (S) testing used CLSI broth microdilution methods and 3 strains were erythromycin (ERY)-R, CLN (CC)-S requiring D-test. Nine comparison agents were tested (4 in Table).

| MIC distributions for CEM-101 as MLSB-macrolide comparisons agents: Occurrences at MIC (μg/ml): | | | | | | | | | | |
|---|---|---|---|---|---|---|---|---|---|---|
| Anti-microbial | ≤0.015 | 0.03 | 0.06 | 0.12 | 0.25 | 0.5 | 1 | 2 | 4 | >4 |
| CEM-101 | 4 | 0 | 1 | 18 | 10 | 6 | 4 | 0 | 0 | 0 |
| TEL | 0 | 0 | 0 | 0 | 0 | 0 | 0 | 8 | 16 | 19 |
| Erythromycin | 0 | 0 | 0 | 0 | 0 | 0 | 0 | 0 | — | 43 |
| CLN | — | — | — | — | 2 | 1 | 0 | 0 | — | 40 |
| Q/D | — | — | — | — | 37 | 6 | 0 | 0 | — | 0 |

CEM-101 remained active against all TEL-R (MIC, ≥2 μg/ml) BHS with all MICs at ≤1 μg/ml (MIC50, 0.12 μg/ml). Highest occurrence of TEL-R strains was in Europe (greatest in Italy). CEM-101 warrants further development for infections caused by BHS.

The potency of CEM-101 against each BHS serogroup was the same with an overall MIC50 and MIC90 of 0.12 and 0.5 μg/ml, respectively. CEM-101 activity was 32-fold (MIC50 comparisons) greater than TEL. All strains were ERY-resistant, but quinupristin/dalfopristin (Q/D) was 100% S. Three CC-S strains (*S. pyogenes*) were D-test (+) and 2 had (+) induction of CEM-101. The susceptibility rates for other comparators were: penicillin, tetracycline, ceftriaxone, amoxicillin/clavulanate, and levofloxacin (100.0%); and tetracycline (46.8%).

Example

Susceptibility testing in broth: Studies with additional strains (including CA-MRSA): MICs at pH 7.4

| Strains | MSSA/MRSA | CEM-101 | AZI | CLR | TEL |
|---|---|---|---|---|---|
| ATCC 25923 | MSSA | 0.125 | 0.5 | 0.5 | 0.5 |
| NRS 192 (US) | CA-MRSA | 0.25 | 1 | 0.5 | 0.25 |
| N4090440 (BE) | CA-MRSA | 0.06 | 0.5-1 | 0.5 | 0.5 |
| N7112046 (BE; Animal MRSA) | MRSA | 0.06 | 2 | 1 | 0.25 |
| STA 44 (Asia) | CA-MRSA | 0.5 | 256 | 128 | 8 |
| CHU (Asia) | CA-MRSA | 2 | 256 | 256 | 32 |
| STA 268 (Asia) | CA-MRSA | 0.5-1 | 128 | 128 | 16 |
| MEH (Asia) | CA-MRSA | 0.125 | 1 | 0.5 | 0.25 |

| In vivo: Intraperitoneal (IP) - Mouse Infection Models (ED$_{50}$) | | |
|---|---|---|
| Compound | MAC-S S. pneumoniae ATCC 49619 (MIC) | MAC-R S. pyogenes 3029 (MIC) |
| CEM-101 | 2.5 mg/kg (<=0.125) | 2.5 mg/kg (<=0.125) |
| AZI | 15 mg/kg (<=0.125) | >150 mg/kg (>64) |
| TEL | 1 mg/kg (<=0.125) | >150 mg/kg (16) |

Example

Antimicrobial activity was assessed in a murine systemic infection model against several bacterial strains including resistant isolates such as MRSA, MRSA 300, mefR S. pneumoniae, an erythromycin resistant S. pyogenes, and a serotype 19A S. pneumoniae isolate.

Example

Efficacy was evaluated in several infection models. CD-1 female mice were infected IP; CEM-101 or comparators were administered as a single oral dose 1 hr post infection. PD50s were determined 24 hr post infection. CEM-101 was further evaluated in a subcutaneous abscess mouse model against S. pneumoniae. CD-1 female mice were infected via SC injection of bacteria mixed with cyclodextran beads. Two hr post infection, mice received a single oral dose of CEM 101 or control agents. At 48 hr post dose, mice were euthanized, abscesses aseptically removed and bacteria enumerated. CFU per abscess was determined and compared to the untreated control. Further evaluation of CEM-101 was performed in cyclophosphamide induced neutropenic mice. At 1.5 hr post thigh infection with S. pneumoniae, mice were orally dosed with CEM-101 or control drugs. 24 hr post treatment, the thighs were processed and CFU/gram of thigh determined.

| Mouse Systemic Infection Model (mg/kg) | | | |
|---|---|---|---|
| | CEM-101 | TEL | CLR |
| S. aureus | 16.3 (11.2-21.3) | >30 | 22.7 (11.3-34.1) |
| MRSA | 7.5 (6.0-8.9) | ND | 5.0 |
| S. pneumoniae (macrolide susceptible) | 6.0 (2.0-10.0) | 19.9 (9.6-30.2) | 32.1 (12.3-52.0) |
| S. pneumoniae (mef R) | 23.2 (15.6-30.7) | 10.6 (2.6-18.6) | >30 |
| S. pyogenes (macrolide susceptible) | 9.4 (7.3-11.5) | 7.8 (5.7-9.8) | 24.8 (18.1-30.4) |
| S. pyogenes (erythromycin R) | 5.1 (4.2-6.1) | 4.4 (3.8-4.9) | 22.8 (14.6-30.9) |

ND = not determined

In the abscess, a 10 mg/Kg QD dose of CEM-101 demonstrated a 4.2 log$_{10}$ decrease while CLR (CL) only achieved a 1.5 log$_{10}$ reduction from untreated mice. CEM-101 in the thigh required 8.0 mg/Kg to achieve a 3 log$_{10}$ reduction from the untreated mice. TEL and CL required 15.5 and 13.5 mg/Kg to achieve the same log$_{10}$ CFU reductions.

Example

Media. Trypicase Soy Agar (TSA) plates-BBL, Franklin Lakes, N.J.; TrypicaseSoy Agar with 5% sheep blood (TSA-II)-BBL, Franklin Lakes, N.J.; Brain Heart Infusion (BHI) Broth-BBL, Franklin Lakes, N.J.; Type III Hog Gastric Mucin-Sigma Aldrich, St Louis Mo.; Cyclodextran Beads-Sigma-Aldrich, St. Louis, Mo.; Cyclophosphamide Sigma-Aldrich, St. Louis, Mo.

Example

Experimental Design. CD-1 Female mice (weighing 18 to22 grams) from Charles River Laboratories (Wilmington, Mass.) were acclimated for 5 days prior to start of studies. All studies were performed under approved IACUC protocols and conform to OLAW standards. Animals had free access to food and water throughout the study as well as provided enrichment.

Mouse Systemic Infection Studies. Eight bacterial isolates were evaluated in this model. For each strain, an overnight culture was utilized. The bacteria were re-suspended in media and diluted either in BHI, 5% or 8% hog gastric mucin to a concentration that would result in 0% survival in mice by 48 hours post infection as determined by initial virulence studies. Bacterial counts were performed to determine inoculum size. Mice received treatment via oral gavage1 hour post infection. At termination of study, percent survival was calculated and the dose effecting 50% survival, the protective dose 50% (PD50), was reported along with 95% confidence intervals as calculated by Probit analysis using GraphPad Prism version 4.03 (GraphPad Software).

Example

Mouse Subcutaneous Abscess. Bacteria were prepared from an overnight plate culture by re-suspending in saline and adjusting the suspension to a 0.1 OD at 625 nm of a 1:10 dilution. The adjusted bacterial suspension was mixed 1:2 with cyclodextran beads prepared as per package instructions. The right flanks of the mice were shaven and injected subcutaneously with 0.2 ml of the bacterial inoculum. Two hours post infection mice were treated via oral gavage with either test article or control drug. 48 hours post infection, mice were euthanized, abscesses aseptically removed, homogenized, serially diluted and plated on bacterial growth agar. After overnight incubation, colonies were counted and CFUs/gram of abscess were determined.

Example

Neutropenic Mouse Thigh Infection. Mice were rendered neutropenic with IP injections of cyclophosamide at day-4 and day-1 of 150 mg/Kg and 100 mg/Kg, respectively. On day 0 mice were infected with approximately 5×10$^5$ CFU/ml of bacteria in a 0.1 ml volume into the right thigh. At 1.5 hours post infection mice received treatment via oral gavage. One group of infected mice were euthanized and thigh processed for bacterial titers to serve as T=0 controls. Twenty-four hours post treatment, the remaining mice were euthanized, thighs aseptically removed, weighed, homogenized, serially diluted and plated on bacterial growth media. CFUs per gram of thigh were calculated after overnight incubation of bacterial plates. The amount of test article required to achieve 1, 2, and 3 log$_{10}$ reductions from 24 hour control thighs were calculated. Additional studies were performed that fractionated the single treatment dose (Q24) into two (Q12), three (Q8) and four (Q6) equivalent doses to determine the pharmacodynamic nature of this compound. Further analysis includes static dose, EC50, 1 log kill and maximal effect (Emax).

Example

Pharmacokinetics. Mouse Pharmacokinetics of CEM-101

| Dose (mg/kg) | Route | Tmax (h) | Cmax (ng/ml) | AUC0-24, (ng*hr/mL) | Half-life (h) |
|---|---|---|---|---|---|
| 2.5 | PO | 1 | 359.15 | 1172.63 | 2.85 |
| 10.0 | PO | 0.5 | 1436.60 | 4757.93 | 2.85 |

It is appreciated herein that the subcutaneous abscess model and the neutropenic thigh model in mice described herein may be more relevant to the understanding and/or predictability of efficacy of the compounds described herein in treating human infection in vivo than the mouse protection model, which may be a better model for the understanding and/or predictability of efficacy of the compounds described herein for treating blood-borne infections, such as bacteremia. For example, relative to CLR and TEL, if a triazole-containing compound, such as CEM-101, has a lower $C_{max}$ in the mouse at the same doses, the MICs are reflected accurately in the mouse protection tests for the susceptible strains. It is observed that CEM-101 is very active when the dose is adjusted for $C_{max}$ in the mouse. Against resistant strains, only CEM-101 is effective even in the mouse protection tests. In contrast, in more relevant models of human infection such as the subcutaneous abscess model or the neutropenic thigh model, CEM-101 performs extraordinarily well and reflects its in vitro potency.

Example

The ability of CEM101 to reduce the microbial load in abscess infection model was also assessed against *S. pneumoniae* isolates.

Example

Mouse Systemic Infections.

Example

Mouse Subcutaneous Abscess~*S. pyogenes* ATCC 8668 (Average $Log_{10}$ CFU/gram of Abscess). Abscess processing 48 hours post infection.

|  | Dose (mg/Kg) | 48 hr. |
|---|---|---|
| Control | — | 8.22 |
| CEM-101 | 10 | 5.35 |
|  | 20 | 2.53 |
| CLR | 10 | 7.63 |
|  | 20 | 7.82 |
| TEL | 10 | 7.06 |
|  | 20 | 6.10 |

Example

Neutropenic Thigh Model. Mouse Neutropenic Thigh *S. pneumoniae* 1629 (Dose (mg/Kg) QD, PO at 2 h post infection; Reduction from 24 hour controls).

| Compound | Dose Route | 1 log10 Reduction | 2 log10 Reduction | 3 log10 Reduction | Max. change in log10CFUs from 24 hr. controls |
|---|---|---|---|---|---|
| CEM-101 | PO | 6.0 | 7.0 | 8.0 | −5.81 |
| TEL | PO | 11.0 | 13.2 | 15.5 | −6.82 |
| CLR | PO | 4.5 | 9.0 | 13.5 | −5.75 |

In the equivalent Mouse Subcutaneous Abscess~*S. pneumoniae* 1629 (10 mg/Kg PO@2 hours post infection) CEM-101 and CLR average $log_{10}$ CFU/gram of abscess remained constant at about 3 and 5.5, respectively from 24 hours to 48 hours; TEL increased from about 3 to about 4.5.

Example

Mouse Neutropenic Thigh *S. pneumoniae* 6303 (Dose (mg/Kg) QD, PO; Reduction from 24 hour controls)

|  | CEM-101 MIC (µg/ml) | PD50 (mg/Kg; 95% CI)) | TEL MIC (µg/ml) | PD50 (mg/Kg; 95% CI)) | CLR MIC (µg/ml) | PD50 (mg/Kg; 95% CI)) |
|---|---|---|---|---|---|---|
| *S. aureus* | 0.12 | 16.3 (11.2-21.3) | 0.06 | >30 | >16 | 22.7 (11.3-34.1) |
| MRSA | 0.12 | 7.5 (6.0-8.9) | 0.5 | ND | >16 | 5.0 |
| MRSA 300 (CA) | 0.12 | 9.5 (5.0-13.9) | 0.25 | 9.2 (6.3-12.1) | >16 | 19.5 (8.2-30.5) |
| *S. pneumoniae* (macrolide susceptible) | <0.03 | 6.0 (2.0-10.0) | <0.06 | 19.9 (9.6-30.2) | >16 | 32.1 (12.3-52.0) |
| *S. pneumoniae* (mefR) | <0.03 | 23.2 (15.6-30.7) | 0.25 | 10.6 (2.6-18.6) | 0.5 | >30 |
| *S. pneumoniae* serotype 19A | 0.25 | 6.6 (4.4-8.9) | 0.5 | 5.7 (4.8-6.7) | >16 | 5.03 (4.8-5.3) |
| *S. pyogenes* (macrolide susceptible) | 0.015 | 9.4 (7.3-11.5) | 0.015 | 7.8 (5.7-9.8) | 0.015 | 24.8 (18.1-30.4) |
| *S. pyogenes* (erythromycin R) | 1.0 | 5.1 (4.2-6.1) | 1.0 | 4.4 (3.8-4.9) | 1.0 | 22.8 (14.6-30.9) |

ND = not determined

| Compound | Dose Route | 1 log10 Reduction | 2 log10 Reduction | 3 log10 Reduction | Max. change in log10CFUs from 24 hr. controls |
|---|---|---|---|---|---|
| CEM-101 | PO | 1.2 | 3.0 | 5.0 | −6.17 |
| TEL | PO | 4.75 | 6.5 | 8.75 | −5.27 |
| CLR | PO | 5.5 | 9.2 | 14.0 | −5.20 |

Example

Mouse Neutropenic thigh Model Fractionated dosing studies: S. pneumoniae 6303 vs. CEM-101 PO

|  | Q24 | Q12 | Q8 | Q6 |
|---|---|---|---|---|
| Static dose (mg/Kg) | 8.2 | 19.2 | 12.1 | 20.5 |
| EC50(mg/Kg) | 5.7 | 14.5 | 9.0 | 16.7 |
| 1 log kill (mg/Kg) | 10.8 | 24.0 | 23.0 | 23.0 |
| Emax (log10CFU/thigh) | 6.38 | 4.95 | 5.01 | 5.83 |

Example

Mouse Lung Infection. The ability of CEM101 to reduce the microbial load in lung infection model was also assessed against S. pneumoniae isolates. Bacteria were prepared from an overnight plate culture by re-suspending in saline and adjusting the suspension to a 0.1 OD at 625 nm of a 1:10 dilution. Mice, under light anesthesia, were inoculated with 50 μl of the S. pneumoniae 1629 bacterial inoculum via intranasal inhalation. Mice received treatment via oral gavage 5, 24, and 36 hours post infection. 48 hours post end of treatment, mice were euthanized, lungs aseptically removed, homogenized, serially diluted and plated on bacterial growth agar. After overnight incubation, colonies were counted and CFUs/gram of lung were determined Average $\log_{10}$ CFU/gram of lung was increased more in the CLR treated mice, from 3 to greater than 7, compared to CEM-101 treated mice, from 5 to about 5.5, from 24 hours to 48 hours.

Example

A worldwide sample of organisms included S. pneumoniae (SPN; 168, 59.3% erythromycin [ERY]-R and 18 multidrug-resistant [MDR]-19A strains), M. catarrhalis (MCAT; 21, 11β-lactamase[+]), H. influenzae (HI; 100, 48 β-lactamase [+]), H. parainfluenzae and H. haemolyticus (12) and Legionella pneumophila (LPN; 30). All S tests were by reference CLSI methods (M7-A7, M100-S18) and breakpoints per CLSI (2008) for comparison agents such as AZI (AZ), CLR (CLR), ERY, TEL (TEL), CLN (CC), Synercid® (SYN), levofloxacin (LEV), linezolid, and rifampin (RIF). SPN were very sensitive to CEM ($MIC_{90}$, 0.25 μg/ml; highest MIC at 0.5 μg/ml) and CEM was 2- and 8-fold more potent than TEL and CC, respectively.

Eighteen serogroup 19A strains exhibited high levels of nonsusceptibility to: macrolides (100.0%), CLN (83.3%), penicillin (83.3%), amox/clav (88.9%), ceftriaxone (33.3%), tetracyclines (83.3% and TMP/SMX (100.0%). Few therapeutic options remain with only TEL ($MIC_{90}$, 1 μg/ml; 100.0% susceptible), Q/D ($MIC_{90}$, 1 μg/ml; 100.0% susceptible) and fluoroquinolones ($MIC_{90}$, 1 μg/ml; 100.0% susceptible) having usable potencies (Table 3). CEM-101 showed a potency two-fold greater than TEL.MDR-19A replacement strains were also CEM-S ($MIC_{90}$, 0.5 μg/ml), compared to TEL ($MIC_{90}$, 1 μg/ml), ERY ($MIC_{90}$, >32 μg/ml), AZI ($MIC_{90}$, >16 μg/ml), CLR ($MIC_{90}$, >32 μg/ml), and CLN ($MIC_{90}$, >16 μg/ml).

LPN were most S to CEM with all MIC values at ≤0.015 μg/ml (TEL MIC90, 0.03 μg/ml). Haemophilus RTI pathogens were less CEM-S ($MIC_{90}$, CEM/TEL): HI (2/4 μg/ml) and others (2/4 μg/ml) with no variations for β-lactamase (+) strains. MCAT CEM-101 MICs were all at ≤0.5 μg/ml, equal to TEL.

S. pneumoniae were very susceptible to CEM-101 with a $MIC_{90}$ of only 0.25 μg/ml. This documented potency (Table 1) was two-fold greater than TEL and eight-fold superior to linezolid ($MIC_{90}$, 2 μg/ml). β-haemolytic streptococci were also susceptible to CEM-101 ($MIC_{90}$, 0.03 μg/ml) with this new agent showing a four-fold advantage (MIC90, 0.12 μg/ml; 100.0% susceptibility) over TEL. Five groups of β-haemolytic strains were tested and all strains showed a monomodal MIC (0.015 μg/ml) distribution and the highest CEM-101 MIC was only 0.12 μg/ml (Table 1).

CEM-101, like TEL, was active against all macrolide- and CLN-resistant viridans group streptococci (five species groups; 51 strains), but all CEM-101 MIC values were at ≤0.12 μg/ml, four-fold more potent than TEL and 64-fold more active than erythromycin.

All CEM-101 MIC results for Haemophilus spp. had a narrow range of only 0.5-4 μg/ml (exception two strains of 0.12 μg/ml that did not exhibit an efflux pump). The overall $MIC_{90}$ for strains in this genus was 2 μg/ml, equal to AZI and two-fold more active than TEL. The various species (H. influenzae, H. parainfluenzae) and β-lactamase production did not significantly alter CEM-101 activity ($MIC_{90}$, 2 μg/ml; Table 1).

Among the MLSB agents, the rank order of potency ($MIC_{90}$ in μg/ml) against M. catarrhalis was: AZI(0.06) >CEM-101=CLR(0.12)>erythromycin=TEL(0.25)>Q/D (0.5)>CLN (2; see Table 1). The β-lactamase activity had no significant effect on the CEM-101 $MIC_{90}$ values (0.12 μg/ml).

CEM-101 ($MIC_{90}$, ≤0.015 μg/ml) was the most active agent tested against Legionella spp. (Table 1), superior to other macrolides, levofloxacin and rifampin. Note that the charcoal content of the test media can interfere with the reference MIC testing of this species.

| Organism (no.) | CEM MIC (μg/ml) 50% | 90% | Range | TEL MIC (μg/ml) 50% | 90% | Range |
|---|---|---|---|---|---|---|
| SPN (150) | 0.015 | 0.25 | ≤0.008-0.5 | 0.03 | 0.5 | ≤0.008-1 |
| MDR-19A (18) | 0.25 | 0.5 | 0.06-0.5 | 0.5 | 1 | 0.12-1 |
| MCAT (21) | 0.12 | 0.12 | ≤0.008-0.5 | 0.12 | 0.25 | ≤0.015-0.5 |
| HI (100) | 1 | 2 | 0.12-4 | 2 | 4 | 0.25-16 |

-continued

| Organism (no.) | CEM MIC (µg/ml) 50% | 90% | Range | TEL MIC (µg/ml) 50% | 90% | Range |
|---|---|---|---|---|---|---|
| Other *Haemophilus* (12) | 2 | 2 | 0.12-2 | 2 | 4 | 0.25-8 |
| LPN (30) | ≤0.015 | ≤0.015 | ≤0.015 | 0.03a | 0.03a | 0.03-0.06a |

1. RIF results, not TEL.

Screening in vitro studies of the compounds described herein indicates a potency comparable or superior to TEL, ERY, AZI and CLR, as well as activity against Gram-positive isolates having documented resistances to macrolides or lincosamides. CEM-101 activity is generally focused against Gram-positive pathogens, but also possesses measurable potencies versus fastidious Gram-negative species (*Haemophilus, Moraxella*), some Enterobacteriaceae (*Salmonella, Shigella*) and pathogens causing various sexual transmitted diseases (STD). CEM-101 activity was measured by reference Clinical and Laboratory Standards Institute (CLSI) methods when testing organisms associated with CARTI (streptococci, *Haemophilus* spp., *Moraxella catarrhalis, Legionella pneumophila*), emerging resistant subsets (serogroup 19A *S. pneumoniae*) and various patterns of MLSB-ketolide resistance among the tested streptococci.

Organism collection: All organisms tested were collected from patients in the USA and European medical centers from 2005 to present. Sources of recovered isolates included bloodstream, skin and soft tissue and respiratory tract infections. Unusual/rare organism species and phenotypes required use of strains isolated prior to 2005 or from other geographic areas. Organisms tested: Streptococci (319), *S. pneumoniae* (150 wild type), *S. pneumoniae* (18 serogroup 19A, USA only), β-haemolytic species (100, five groups), viridans group (51, five species), *Haemophilus* species (111), *H. influenzae* (100, 48 β-lactamase producers), *H. parainfluenzae* (11), *M. catarrhalis* (21, 11 β-lactamase producers), *L. pneumophila* (30).

Susceptibility testing: Ninety-six well frozen-form assay panels were produced by JMI Laboratories and consisted of three media types: cation-adjusted Mueller-Hinton broth, cation adjusted Mueller-Hinton broth with 2.5-5% lysed horse blood (for testing streptococci) and Haemophilus Test Medium (HTM). CLSI broth microdilution and agar dilution methods per M7-A7 [2006] were used. Quality control (QC) ranges and interpretive criteria for comparator compounds were those published in CLSI M100-S18 [2008]. Tested QC strains included *S. aureus* ATCC 29213, *E. faecalis* ATCC 29212, *S. pneumoniae* ATCC 49619 and *H. influenzae* ATCC 49247 and 49766. All QC results were within published limits. Agar dilution methods were used for *L. pneumophila* tested on BCYE agar. Comparison agents were tested by Etest, also on BCYE media. A wide variety of comparison agents were utilized including: amoxicillin/clavulanate (amox/clav), AZI, cefdinir, CLR, CLN, erythromycin, levofloxacin, linezolid, quinupristin/dalfopristin (Q/D), TEL and trimethoprim/sulfamethoxazole (TMP/SMX) all assessed by broth microdilution; and ciprofloxacin, tetracycline, ampicillin and rifampin were additionally tested on agar.

The Table shows excellent CEM-101 potency against streptococci (all MICs, ≤0.5 µg/ml) and moderate activity against Gram-negative CA-RTI pathogens (MICs, ≤0.008-4 µg/ml).

| CEM-101 MIC distributions for all tested RTI organisms (398 strains) showing Occurrences at MIC (µg/ml). | | | | | | | | | | | | |
|---|---|---|---|---|---|---|---|---|---|---|---|---|
| Organism (no. tested) | ≤0.008 | 0.015 | 0.03 | 0.06 | 0.12 | 0.25 | 0.5 | 1 | 2 | 4 | 8 | ≥16 |
| *S. pneumoniae* (150) | 62 | 25 | 8 | 9 | 7 | 33 | 6 | 0 | 0 | 0 | 0 | 0 |
| β-haemolytic *streptococci* (100) | 21 | 65 | 4 | 8 | 2 | 0 | 0 | 0 | 0 | 0 | 0 | 0 |
| Viridans group *streptococci* (15) | 27 | 11 | 4 | 7 | 2 | 0 | 0 | 0 | 0 | 0 | 0 | 0 |
| *M. catarrhalis* (21) | 1 | 1 | 1 | 5 | 12 | 0 | 1 | 0 | 0 | 0 | 0 | 0 |
| *H. influenzae* (100) | 0 | 0 | 0 | 0 | 1 | 0 | 5 | 48 | 42 | 4 | 0 | 0 |
| *Haemophilus*, other (12) | 0 | 0 | 0 | 0 | 1 | 0 | 0 | 4 | 7 | 0 | 0 | 0 |

CEM-101 exhibited potent activity against streptococci (MIC50, 0.015 µg/ml), and various other Gram-positive cocci including strains resistant to erythromycin and CLN. CEM-101 showed complete activity against MDR serogroup 19A pneumococci (16 of 18 MIC values at 0.25 or 0.5 µg/ml) and was two-fold more active than TEL and Q/D. CEM-101 also inhibited Gram-negative species associated with CA-RTI (*H. influenzae* [MIC90, 2 µg/ml], *Legionella* spp. [MIC90, ≤0.015 µg/ml], and *M. catarrhalis* [MIC90, 0.12 µg/ml]).

Example

Macrolide resistant isolates (29) (based on CLR MICs determination; 19 MLSB, 10 M-phenotype based on erythromycin and CLN resistance dissociation) were selected (for which 6 were TEL-I and 7 TEL-R based on EUCAST breakpoints [S<=0.25–R>0.5]). MICs were determined by geometric microdilution in CAMH broth+2.5% lysed horse blood according to CLSI, using SP ATCC-49619 as a control.

Example

ATCC-49619 MICs were ≤0.008 mg/L for TEL and CEM-101. Data for ML-resistant isolates are shown in the Table. In this Belgian collection of *S. pneumoniae* from confirmed CAP resistant to macrolides, CEM-101 shows globally lower MICs compared to TEL, especially with respect to TEL-I and TEL-R isolates.

| Phenotype* | No. | TEL range | TEL geom. mean | TEL MIC$_{90}$ | CEM-101 range | CEM-101 geom. mean | CEM-101 MIC$_{90}$ |
|---|---|---|---|---|---|---|---|
| TEL-S | 16 | 0.008-0.25 | 0.021 | 0.25 | 0.008-0.063 | 0.022 | 0.063 |
| TEL-I | 6 | 0.5-0.5 | 0.5 | 0.5 | 0.063-0.5 | 0.223 | 0.5 |
| TEL-R | 7 | 1-3 | 1.426 | 3.0 | 0.5-1.0 | 0.906 | 1.0 |

*MLS$_B$ for 7/16 of TEL-S, 5/6 pf TEL-I, and 7/7 of TEL-R isolates (S/I/R are defined based on EUCAST breakpoints (S ≤ 0.25-R > 0.5)

CEM-101 shows globally lower MICs compared to TEL, especially with respect to TEL-I and TEL-R isolates tested against this Belgian collection of *S. pneumoniae* from confirmed cases of CAP which are resistant to macrolides. As described herein, CEM-101 has the potential to be useful as an alternative to telithromcyin in areas with high ML resistance and emerging resistance to TEL.

|  | S. pneumoniae ATCC 49619 | S. pneumoniae ErmB 303 | S. pneumoniae 163 (Mef A) | S. pneumoniae 3773 (Erm B) | S. pneumoniae 5032 |
|---|---|---|---|---|---|
| AZI | ≤0.125 | >64 | 8 | >64 | >64 |
| TEL | ≤0.125 | ≤0.125 | ≤0.125 | 1 | 0.5 |
| CEM-101 | ≤0.125 | ≤0.125 | ≤0.125 | 0.5 | 0.5 |

|  | S. pyogenes 1721 | S. pyogenes 1850 | S. pyogenes 3029 | S. pyogenes 3262 | H. influenzae ATCC 49247 |
|---|---|---|---|---|---|
| AZI | >64 | >64 | >64 | >64 | 2 |
| TEL | 64 | 8 | 16 | 32 | 4 |
| CEM-101 | 0.5 | ≤0.125 | ≤0.125 | 0.5 | 2 |

| MIC$_{50}$ and MIC$_{90}$ [µg/mL] | | | | | | | |
|---|---|---|---|---|---|---|---|
|  | # Of Strains | CEM-101 MIC$_{50}$ | CEM-101 MIC$_{90}$ | OP 1055 MIC$_{50}$ | OP 1055 MIC$_{90}$ | TEL MIC$_{50}$ | TEL MIC$_{90}$ |
| S. pneumoniae PEN-S, TEL S; Macr-S | 10 | 0.03 | 0.03 | 0.03 | 0.03 | 0.03 | 0.03 |
| S. pneumoniae PEN-R, TEL I/R; Macr-R | 12 | 0.5 | 0.5 | 4 | 4 | 2 | 8 |
| S. pneumoniae PEN-S, TEL S; Macr-R | 24 | 0.03 | 0.03 | 0.06 | 0.06 | 0.06 | 0.06 |
| S. pyogenes TEL S; Macr-S | 10 | 0.03 | 0.03 | 0.03 | 0.03 | 0.03 | 0.03 |
| S. pyogenes TEL R; Macr-R | 10 | 0.125 | 0.25 | 2 | 2 | 32 | 32 |
| S. pyogenes TEL S; Macr-R | 30 | 0.03 | 0.03 | 0.125 | 0.25 | 0.125 | 0.5 |

|  | # Of Strains | 2-F-TEL MIC$_{50}$ | 2-F-TEL MIC$_{90}$ | AZI MIC$_{50}$ | AZI MIC$_{90}$ | PEN MIC$_{50}$ | PEN MIC$_{90}$ |
|---|---|---|---|---|---|---|---|
| S. pneumoniae PEN-S, TEL S; Macr-S | 10 | 0.03 | 0.03 | 0.03 | 0.03 | 0.03 | 0.03 |
| S. pneumoniae PEN-R, TEL I/R; Macr-R | 12 | 1 | 8 | >32 | >32 | 4 | 8 |
| S. pneumoniae PEN-S, TEL S; Macr-R | 24 | 0.03 | 0.06 | >32 | >32 | 0.03 | 0.03 |
| S. pyogenes TEL S; Macr-S | 10 | 0.03 | 0.03 | 0.125 | 0.125 | 0.03 | 0.03 |
| S. pyogenes TEL R; Macr-R | 10 | 32 | 32 | >32 | >32 | 0.03 | 0.03 |
| S. pyogenes TEL S; Macr-R | 30 | 0.25 | 0.5 | >32 | >32 | 0.03 | 0.03 |

Example

Where on-scale MIC results were available, CEM-101 (MIC90, 0.015 µg/ml) was two- and eight-fold more active than CLR or TEL and AZI, respectively, against streptococci susceptible to erythromycin. For streptococci non-susceptible to erythromycin, CEM-101 had an elevated MIC (MIC90, 0.25 µg/ml); however, CEM-101 was at least two-fold more active than either TEL or CLN. When tested against erythromycin- and CLN-non-susceptible streptococci, all but one strain remained susceptible to TEL, but all were inhibited by CEM-101 at ≤0.5 µg/ml.

Activity of CEM-101 and selected comparison agents against *streptococci* having various $MLS_B$ resistance patterns (three groups, 300 strains*).

| $MLS_B$-ketolide resistance pattern | Anti-microbial | MIC (µg/ml) | | |
|---|---|---|---|---|
| (No. tested)[a] | agent | 50% | 90% | Range |
| ERY-S (164)[b] | CEM-101 | ≤0.008 | 0.015 | ≤0.008-0.03 |
| | TEL | 0.03 | 0.03 | 0.008-0.06 |
| | CLR | 0.03 | 0.03 | ≤0.008-0.25 |
| | AZI | 0.06 | 0.12 | ≤0.008-0.5 |
| | CLN | ≤0.12 | ≤0.12 | ≤0.12-0.5 |
| | Q/D | 0.5 | 0.5 | ≤0.12-2 |
| | Amox/clav | ≤0.25 | 2 | ≤0.25->4 |
| | Levofloxacin | 1 | 1 | 0.25->4 |
| | Linezolid | 1 | 2 | 0.25-2 |
| ERY-NS, CLN-and TEL-S (48)[c] | CEM-101 | 0.03 | 0.12 | ≤0.008-0.25 |
| | TEL | 0.12 | 0.5 | 0.03-1 |
| | CLN | ≤0.12 | 0.25 | ≤0.12-0.25 |
| | Q/D | 0.5 | 1 | 0.25-2 |
| | Amox/clav | ≤0.25 | 2 | ≤0.25->4 |
| | Levofloxacin | 1 | 2 | 0.25->4 |
| | Linezolid | 1 | 2 | 0.5-2 |
| ERY-and CLN-NS, TEL-S (88)[d] | CEM-101 | 0.06 | 0.25 | ≤0.008-0.5 |
| | TEL | 0.12 | 1 | 0.03-1 |
| | Q/D | 0.5 | 1 | 0.25-2 |
| | Amox/clav | 2 | >8 | ≤0.25->8 |
| | Levofloxacin | 1 | 1 | 0.25-2 |
| | Linezolid | 1 | 1 | 0.5-2 |

[a]S = susceptible and NS = non-susceptible e.g. includes intermediate and resistant strains.
[b]Includes: *Streptococcus anginosus* (9 strains), *S. constellatus* (8 strains), *S. intermedius* (7 strains), *S. mitis* (2 strains), *S. oralis* (3 strains), *S. pneumoniae* (61 strains), Group A (29 strains), Group B (17 strains), Group C (11 strains), Group F (6 strains) and Group G *Streptococcus* (11 strains).
[c]Includes: *Streptococcus anginosus* (2 strains), *S. constellatus* (2 strains), *S. intermedius* (3 strains), *S. mitis* (7 strains), *S. oralis* (7 strains), *S. pneumoniae* (14 strains), Group A (1 strain), Group B (7 strains), and Group G *Streptococcus* (5 strains),
[d]Includes: *Streptococcus constellatus* (1 strain), *S. pneumoniae* (75 strains), Group B (7 strains), Group C (2 strains), and Group F *Streptococcus* (3 strains).
One strain (group C *streptococcus*) was NS to ER, CLN and TEL, but had a CEM-101 MIC at 0.06 µg/ml. This is an important emerging pattern, especially in Europe

Example

Macrolide-Susceptible And Macrolide-Resistant Streptococci. The activity of CEM-101 compared to those of erythromycin, AZI, CLR, TEL, CLN, penicillin G, amoxicillin/clavulanate, levofloxacin, and moxifloxacin against a range of pneumococci was tested. The potency of CEM-101, erythromycin, AZI, CLR, TEL, CLN, penicillin G, amoxicillin/clavulanate, levofloxacin and moxifloxacin against 124 *S. pyogenes* strains was also tested.

Pneumococcal MIC50 and MIC90 values (µg/ml)

| Drug | Macrolide susceptible (50) Range | MIC50 | MIC90 | Macrolide resistant (171) Range | MIC50 | MIC90 |
|---|---|---|---|---|---|---|
| CEM-101 | 0.002-0.015 | 0.03 | 0.25 | 0.004-1 | 0.06 | 0.25 |
| ERY | 0.03-0.25 | 0.06 | 0.125 | 1->64 | >64 | >64 |
| AZI | 0.06-0.25 | 0.125 | 0.125 | 1->64 | >64 | >64 |
| CLR | 0.015-0.06 | 0.03 | 0.06 | 0.25->64 | 32 | >64 |
| TEL | 0.015-0.03 | 0.03 | 0.03 | 0.03-2 | 0.125 | 0.5 |
| CLN | 0.015-0.06 | 0.03 | 0.06 | 0.03->64 | 0.125 | >64 |
| Amox/clav | 0.015-8 | 0.5 | 2 | 0.015-16 | 1 | 8 |
| Pen G | 0.015-8 | 1 | 2 | 0.008->16 | 1 | 4 |
| Levo | 1-32 | 1 | 16 | 0.06-32 | 1 | 2 |
| Moxi | 0.125-8 | 0.25 | 4 | 0.125-4 | 0.25 | 0.5 |

MICs for group A *streptococci*

| Drug | Macrolide susceptible (26) Range | MIC50 | MIC90 | Macrolide resistant (98) Range | MIC50 | MIC90 |
|---|---|---|---|---|---|---|
| CEM-101 | 0.008-0.03 | 0.015 | 0.3 | 0.015-1 | 0.06 | 0.5 |
| ERY | 0.03-0.25 | 0.06 | 0.125 | 2->64 | 16 | >64 |
| AZI | 0.06-0.25 | 0.125 | 0.25 | 0.5->64 | 8 | >64 |
| CLR | 0.015-0.06 | 0.03 | 0.06 | 0.25->64 | 4 | >64 |
| TEL | 0.03-0.06 | 0.06 | 0.06 | 0.03-16 | 0.25 | 8 |
| CLN | 0.03-0.125 | 0.06 | 0.06 | 0.03->64 | 0.125 | >64 |
| Amox/clav | 0.015-0.03 | 0.03 | 0.03 | <0.015-0.125 | 0.03 | 0.03 |
| Pen G | <0.008-0.125 | 0.015 | 0.015 | <0.008-0.125 | 0.015 | 0.015 |
| Levo | 0.5-1 | 0.5 | 0.5 | 0.5-2 | 0.5 | 1 |
| Moxi | 0.125-0.25 | 0.25 | 0.25 | 0.125-0.5 | 0.25 | 0.25 |

All group A streptococcal strains were penicillin G susceptible. Against macrolide susceptible strains, CEM-101 MICs were 0.008-0.03 µg/ml and those against macrolide resistant strains (all phenotypes) MICs were 0.008-0.5 µg/ml. TEL MICs were up to four fold higher than those of CEM-101. Importantly, 11/13 erm(B) strains were TEL resistant with MICs of 4 and 8 µg/ml (6) while all had low CEM-101 MICs, similar to those of other resistance phenotypes (range 0.016-0.5 µg/ml).

Example

Bacteria and Antimicrobials. MICs were determined for 221 clinical pneumococcal strains, including 50 macrolide-susceptible and 171 macrolide-resistant organisms. Macrolide-resistant strains all had defined genotypes and comprised strains with erm(B) (54 strains), mef(A) (51 strains), erm(B)+mef(A) (31 strains), erm(A) (4 strains) and mutations in L4 ribosomal protein (27 strains), and 23S rRNA (4 strains). These 221 strains also included 27 quinolone non-susceptible phenotypes with defined quinolone resistance determinant regions (QRDRs) (levofloxacin MICs 4-32 µg/ml) and the entire spectrum of penicillin G resistance phenotypes using the latest Clinical Laboratory Standards Institute (CLSI) oral penicillin V susceptibility classification (4). The 124 group A streptococci tested by MIC included 26 macrolide-susceptible and 98 macrolide-resistant strains. The latter included 19 strains with erm(B), 38 mef(A), 40 erm(A) and 1 strain with an L4 mutation. Because strains of both species were chosen for their macrolide resistance phenotype, only susceptible strains were consistently recent (2003-2008) isolates; some resistant strains were isolated up to five years earlier (1998). *Streptococcus pneumoniae* ATCC 49619 was included as the quality control strain for each species in each run.

For resistance selection testing, one each of the following pneumococcal resistance phenotypes was tested: macrolide-susceptible, erm(B) positive, mef(A) positive, erm(B)+mef(A) positive, erm(A) positive and with mutation in ribosomal proteins (L4, L22) and 23S rRNA. Five strains of group A streptococci were tested with one each macrolide-susceptible, erm(B) positive, mef(A) positive, erm(A) positive and with L4 mutation.

MICs were done by the agar dilution technique which. Mueller-Hinton agar (BD Diagnostics, Sparks, Md.) +5% sheep blood agar was used, with $10^4$ CFU/spot and overnight incubation at 35° C. in ambient air. The usual quality control strains were included in each run. For resistance selection, CLSI macrodilution was used for MIC testing.

All macrolide-resistant parental strains were tested for the presence of the erm(B), erm(A), mef(E) and mef(A) genes by PCR amplification. The presence of mutations in the L4 and L22 ribosomal proteins and 23S rRNA (II and V domain) were examined in all parental isolates and in CEM-101 resistant clones (CEM-101 MIC>1 µg/ml) using conventional primers and conditions. The nucleotide sequences were obtained by direct sequencing with a CEQ8000 genetic analysis system (Beckman Coulter, Fullerton, Calif.).

Serial passages were performed daily from each strain in sub-inhibitory concentrations of all antimicrobials. In all cases, broth medium was 1 ml per tube of cation-adjusted Mueller-Hinton broth (BD Diagnostics, Sparks, Md.) +5% lysed horse blood. For each subsequent daily passage, an inoculum (10 µl) was taken from the tube one to two dilutions below the MIC that matched the turbidity of a growth control tube. This inoculum was used to determine the next MIC. Daily passages were performed until a significant increase in MIC (≥8 times) was obtained. A minimum of 14 passages was performed unless MICs≥32 µg/ml were obtained. The maximal number of passages was 50. Stability of the acquired resistance was determined by MIC determinations after 10 daily passages of the mutants on blood agar without antibiotics. MICs of each resistant pneumococcal clone to each compound were determined by macrodilution MIC. Identity of the obtained mutants and their respective parents was confirmed by pulsed-field gel electrophoresis (PFGE) at the end of the study. PFGE of SmaI digested DNA was performed using a CHEF DR III apparatus (Bio-Rad, Hercules, Calif.) with the following run parameters: switch time of 5 to 20 s and a run time of 16 h.

The frequency of spontaneous single step mutations was determined by spreading suspensions (approximately $10^{10}$ CFU/ml) on Mueller Hinton Agar (BD Diagnostics, Sparks, Md.) with 5% sheep blood at 2, 4 and 8× MIC. After incubation at 35° C. in 5% $CO_2$ for 48 h, the resistance frequency was calculated as the number of colonies with MICs increased at least 4× parental MIC per inoculum. Single step studies were not performed with AZI, CLR, CLN and TEL for strains with MICs≥4 µg/ml. Results of pneumococcal MIC testing are presented in the following Tables.

| MICs (µg/ml) of drugs against *pneumococcal* strains | | | |
|---|---|---|---|
| Drug | MIC range | $MIC_{50}$ | $MIC_{90}$ |
| Penicillin G (221ª) | 0.008->16 | 1 | 4 |
| Penicillin S (53) | 0.008-0.06 | .03 | .06 |
| Penicillin I (63) | 0.125-1 | .5 | 1 |
| Penicillin R (105) | 2->16 | 4 | 8 |
| Macrolide S (50) | 0.015-8 | 1 | 2 |
| erm(B) (54) | 0.03-16 | 1 | 4 |
| mef(A) (51) | 0.008-4 | 0.125 | 4 |
| erm(A) (4) | 0.03-0.03 | — | — |
| erm(B) + mef(A) (31) | 0.03-8 | 2 | 4 |
| L4 (27) | 1->16 | 4 | 16 |
| 23S rRNA (4) | 0.015-0.5 | — | — |
| Quinolone S (195) | 0.008->16 | 1 | 4 |
| Quinolone R (27) | 0.015-8 | 0.25 | 4 |
| CEM-101 | 0.002-1 | 0.03 | 0.25 |
| Penicillin S | 0.002-0.25 | 0.03 | 0.125 |
| Penicillin I | 0.002-0.25 | 0.03 | 0.25 |
| Penicillin R | 0.004-1 | 0.06 | 0.25 |
| Macrolide S | 0.002-0.015 | 0.008 | 0.015 |
| erm(B) | 0.004-1 | 0.03 | 0.5 |
| mef(A) | 0.008-0.25 | 0.03 | 0.125 |
| erm(A) | 0.008-0.015 | — | — |
| erm (B) + mef(A) | 0.015-1 | 0.125 | 0.25 |
| L4 | 0.03-0.125 | 0.06 | 0.125 |
| 23S rRNA | 0.002-0.03 | — | — |
| Quinolone S | 0.002-1 | 0.03 | 0.25 |
| Quinolone R | 0.004-.25 | 0.008 | 0.06 |
| Erythromycin | 0.03->64 | 64 | >64 |
| Penicillin S | 0.03->64 | 4 | >64 |
| Penicillin I | 0.03->64 | >64 | >64 |
| Penicillin R | 0.03->64 | >64 | >64 |
| Macrolide S | 0.03-0.25 | 0.06 | 0.125 |
| erm(B) | 16->64 | >64 | >64 |

| MICs (μg/ml) of drugs against *pneumococcal* strains | | | |
|---|---|---|---|
| Drug | MIC range | MIC₅₀ | MIC₉₀ |
| mef(A) | 1->64 | 4 | 32 |
| erm(A) | 2-4 | — | — |
| erm(B) + mef(A) | 4->64 | >64 | >64 |
| L4 | 4->64 | >64 | >64 |
| 23S rRNA | 8->64 | — | — |
| Quinolone S | 0.03->64 | >64 | >64 |
| Quinolone R | 0.03->64 | 0.06 | >64 |
| AZI | 0.06->64 | 16 | >64 |
| Penicillin S | 0.06->64 | 4 | >64 |
| Penicillin I | 0.06->64 | >64 | >64 |
| Penicillin R | 0.06->64 | >64 | >64 |
| Macrolide S | 0.06-0.25 | 0.125 | .0125 |
| erm(B) | >64->64 | >64 | >64 |
| mef(A) | 1->64 | 4 | 8 |
| erm(A) | 2-8 | — | — |
| erm (B) + mef(A) | 2->64 | >64 | >64 |
| L4 | 2->64 | >64 | >64 |
| 23S rRNA | 32->64 | — | — |
| Quinolone S | 0.06->64 | >64 | >64 |
| Quinolone R | 0.06->64 | 0.125 | >64 |
| CLR | 0.125->64 | 8 | >64 |
| Penicillin S | 0.015->64 | 1 | >64 |
| Penicillin I | 0.03->64 | 16 | >64 |
| Penicillin R | 0.015->64 | 16 | >64 |
| Macrolide S | 0.015-0.06 | 0.03 | 0.06 |
| erm(B) | 4->64 | >64 | >64 |
| mef(A) | 0.5-32 | 2 | 4 |
| erm(A) | 0.25-0.5 | — | — |
| erm (B) + mef(A) | 1->64 | >64 | >64 |
| L4 | 1-32 | 16 | 32 |
| 23S rRNA | 8-16 | — | — |
| Quinolone S | 0.015->64 | 16 | >64 |
| Quinolone R | 0.015->64 | 0.03 | >64 |
| TEL | 0.015-2 | 0.06 | 0.5 |
| Penicillin S | 0.015-1 | 0.06 | 0.25 |
| Penicillin I | 0.015-1 | 0.06 | 0.5 |
| Penicillin R | 0.015-2 | 0.125 | 0.5 |
| Macrolide S | 0.015-0.03 | 0.03 | 0.03 |
| erm (B) | 0.03-2 | 0.06 | 1 |
| mef(A) | 0.03-0.5 | 0.125 | 0.25 |
| erm (A) | 0.03-0.06 | — | — |
| erm (B) + mef(A) | 0.03-2 | 0.5 | 1 |
| L4 | 0.06-0.25 | 0.125 | 0.25 |
| 23S rRNA | 0.03-0.06 | — | — |
| Quinolone S | 0.015-2 | 0.125 | 0.5 |
| Quinolone R | 0.015-1 | 0.03 | 0.125 |
| CLN | 0.015->64 | 0.06 | >64 |
| Penicillin S | 0.03->64 | 0.06 | >64 |
| Penicillin I | 0.03->64 | 0.125 | >64 |
| Penicillin R | 0.015->64 | 0.06 | >64 |
| Macrolide S | 0.015-0.06 | 0.03 | 0.06 |
| erm (B) | 0.06->64 | >64 | >64 |
| mef(A) | 0.03-0.125 | 0.06 | 0.06 |
| erm (A) | 0.125-0.25 | — | — |
| erm (B) + mef(A) | 0.03->64 | 0.06 | >64 |
| L4 | 0.03-0.125 | 0.06 | 0.125 |
| 23S rRNA | 0.03-1 | — | — |
| Quinolone S | 0.015->64 | 0.06 | >64 |
| Quinolone R | 0.03-64 | 0.03 | 64 |
| Amoxicillin/Clavulanate | 0.015-16 | 0.05 | 8 |
| Penicillin S | 0.015-0.125 | 0.03 | 0.06 |
| Penicillin I | 0.03-2 | 0.5 | 1 |
| Penicillin R | 0.125-16 | 2 | 8 |
| Macrolide S | 0.015-8 | 0.5 | 2 |
| erm(B) | 0.015-8 | 0.5 | 8 |
| mef(A) | 0.015-8 | 0.125 | 2 |
| erm (A) | 0.03-0.03 | — | — |
| erm (B) + mef(A) | 0.03-16 | 2 | 8 |
| L4 | 0.125-8 | 4 | 8 |
| 23S rRNA | 0.03-0.06 | — | — |
| Quinolone S | 0.015-16 | 1 | 8 |
| Quinolone R | 0.015-4 | 0.5 | 2 |
| Levofloxacin | 0.06-32 | 1 | 8 |
| Penicillin S | 0.06-32 | 1 | 16 |
| Penicillin I | 1-32 | 1 | 2 |
| Penicillin R | 0.5-16 | 1 | 2 |
| Macrolide S | 1-32 | 1 | 16 |
| erm (B) | 0.5-32 | 1 | 2 |
| mef(A) | 0.5-8 | 1 | 2 |
| erm (A) | 1-1 | — | — |
| erm (B) + mef(A) | 1-16 | 1 | 16 |
| L4 | 0.5-16 | 1 | 2 |
| 23S rRNA | 0.06-1 | — | — |
| Quinolone S | 0.06-2 | 1 | 2 |
| Quinolone R | 4-32 | 16 | 16 |
| Moxifloxacin | 0.125-8 | 0.25 | 2 |
| Penicillin S | 0.125-8 | 0.5 | 4 |
| Penicillin I | 0.125-4 | 0.25 | 0.5 |
| Penicillin R | 0.125-4 | 0.25 | 0.5 |
| Macrolide S | 0.125-8 | 0.25 | 4 |
| erm (B) | 0.125 | 0.25 | 0.5 |
| mef(A) | 0.125-4 | 0.25 | 0.5 |
| erm (A) | 0.25-0.5 | — | — |
| erm (B) + mef(A) | 0.125-2 | 0.25 | 0.5 |
| L4 | 0.125-4 | 0.25 | 0.5 |
| 23S rRNA | 0.25-0.5 | — | — |
| Quinolone S | 0.125-1 | 0.25 | 0.5 |
| Quinolone R | 0.5-8 | 4 | 4 |

[a] No. strains tested.

| MIC50 and MIC90 values (μg/ml) of pneumococcal strains with defined macrolide-resistant mechanism | | | | | | | | |
|---|---|---|---|---|---|---|---|---|
| | erm(B) (54) | | mef(A) (51) | | erm(B) + mef(A) (31) | | L4 mutations (27) | |
| Drug | MIC₅₀ | MIC₉₀ | MIC₅₀ | MIC₉₀ | MIC₅₀ | MIC₉₀ | MIC₅₀ | MIC₉₀ |
| CEM-101 | 0.03 | 0.5 | 0.03 | 0.125 | 0.125 | 0.25 | 0.06 | 0.125 |
| Erythromycin | >64 | >64 | 4 | 32 | >64 | >64 | >64 | >64 |
| AZI | >64 | >64 | 4 | 8 | >64 | >64 | >64 | >64 |
| CLR | >64 | >64 | 2 | 4 | >64 | >64 | 16 | 32 |
| TEL | 0.06 | 1 | 0.125 | 0.25 | 0.5 | 1 | 0.125 | 0.25 |
| CLN | >64 | >64 | 0.06 | 0.06 | 0.06 | >64 | 0.06 | 0.125 |
| Amoxicillin Clavulanate | 0.5 | 8 | 0.125 | 2 | 2 | 8 | 4 | 8 |
| Levofloxacin | 1 | 2 | 1 | 2 | 1 | 16 | 1 | 2 |
| Moxifloxacin | 0.25 | 0.5 | 0.25 | 0.5 | 0.25 | 0.5 | 0.25 | 0.5 |
| Penicillin G | 1 | 4 | 0.125 | 4 | 2 | 4 | 4 | 16 |

CEM-101 had an MIC range against macrolide-susceptible pneumococci of 0.002-0.015 µg/ml and a range against macrolide-resistant pneumococci (all phenotypes) of 0.004-1 µg/ml. Only 3 strains with erm(B) [with and without mef(A)] had CEM-101 MICs of 1.0 µg/ml and 218/221 strains had CEM-101 MICs of <0.5 µg/ml. By contrast, corresponding TEL MIC ranges were 0.015-0.03 µg/ml for macrolide-susceptible and 0.015-2 µg/ml for macrolide-resistant strains. CEM-101 MICs were up to four-fold lower than those of TEL against macrolide-susceptible and -resistant strains. All group A streptococcal strains were penicillin G-susceptible. MICs are presented in the following Tables,

| MICs (µg/ml) of drugs against group A *streptococci* | | | |
|---|---|---|---|
| Drug | MIC Range | MIC 50 | MIC 90 |
| CEM - 101 (124[a]) | 0.008-1 | 0.06 | 0.5 |
| Macrolide S (26) | 0.008-0.03 | 0.015 | 0.03 |
| Erm(B) (19) | 0.03-1 | 0.5 | 1 |
| Mef(A) (38) | 0.06-0.25 | 0.125 | 0.25 |
| Erm(A) (40) | 0.016-0.5 | 0.03 | 0.125 |
| L4 (1) | 0.06 | — | — |
| Erythromycin | 0.03->64 | 16 | >64 |
| Macrolide S | 0.03-0.25 | 0.06 | 0.125 |
| Erm(B) | >64->64 | >64 | >64 |
| Mef(A) | 8-32 | 16 | 32 |
| Erm(A) | 2->64 | 4 | >64 |
| L4 | 2 | — | — |
| AZI | 0.06->64 | 8 | >64 |
| Macrolide S | 0.06-0.25 | 0.125 | 0.25 |
| Erm(B) | >64->64 | >64 | >64 |
| Mef(A) | 0.5-16 | 8 | 8 |
| Erm(A) | 2->64 | 16 | >64 |
| L4 | 2 | — | — |
| CLR | 0.015->64 | 4 | >64 |
| Macrolide S | 0.015-0.06 | 0.03 | 0.06 |
| Erm(B) | 32->64 | >64 | >64 |
| Mef(A) | 0.5-8 | 4 | 8 |
| Erm(A) | 0.25->64 | 2 | >64 |
| L4 | 1 | — | — |
| TEL | 0.03-16 | 0.125 | 8 |
| Macrolide S | 0.03-0.06 | 0.06 | 0.06 |
| Erm(B) | 0.03-16 | 8 | 16 |
| Mef(A) | 0.125-1 | 0.5 | 1 |
| Erm(A) | 0.03-0.25 | 0.06 | 0.125 |
| L4 | 0.06 | — | — |
| Amoxicillin/Clavulanate | <0.015-0.125 | 0.03 | 0.03 |
| Macrolide S | 0.015-0.03 | 0.03 | 0.03 |
| Erm(B) | <0.015-0.125 | <0.015 | 0.03 |
| Mef(A) | <0.015-0.125 | 0.015 | 0.06 |
| Erm(A) | <0.015-0.03 | 0.03 | 0.03 |
| L4 | 0.03 | — | — |
| Levofloxacin | 0.5-2 | 0.5 | 1 |
| Macrolide S | 0.5-1 | 0.5 | 0.5 |
| Erm(B) | 0.5-1 | 0.5 | 1 |
| Mef(A) | 0.5-2 | 0.5 | 1 |
| Erm(A) | 0.5-2 | 0.5 | 1 |
| L4 | 0.5 | — | — |
| Moxifloxacin | 0.0125-0.5 | 0.25 | 0.25 |
| Macrolide S | 0.125-0.25 | 0.25 | 0.25 |
| Erm(B) | 0.125-0.25 | 0.25 | 0.25 |
| Mef(A) | 0.25-0.5 | 0.25 | 0.25 |
| Erm(A) | 0.125-0.5 | 0.25 | 0.25 |
| L4 | 0.25 | — | — |
| Pen G | <0.008-0.125 | 0.015 | 0.015 |
| Macrolide S | 0.008-0.015 | 0.015 | 0.015 |
| Erm(B) | <0.008-0.125 | 0.015 | 0.015 |
| Mef(A) | <0.008-0.125 | 0.015 | 0.03 |
| Erm(A) | <0.008-0.015 | 0.015 | 0.015 |
| L4 | 0.015 | — | — |
| CLN | 0.03->64 | 0.125 | >64 |
| Macrolide S | 0.03-0.125 | 0.06 | 0.06 |
| Erm(B) | 0.06->64 | >64 | >64 |
| Mef(A) | 0.03-0.125 | 0.06 | 0.125 |
| Erm(A) | 0.06-0.5 | 0.125 | 0.25 |
| L4 | 0.06 | — | — |

[a]Number of strains tested

| MIC50 and MIC90 values (µg/ml) of group A streptococcal strains with defined macrolide-resistant mechanisms | | | | | | |
|---|---|---|---|---|---|---|
| | erm(B) (19) | | mef(A) (38) | | erm(A) (40) | |
| Drug | MIC50 | MIC90 | MIC50 | MIC90 | MIC50 | MIC90 |
| CEM-101 | 0.5 | 1 | 0.125 | 0.25 | 0.03 | 0.125 |
| Erythromycin | >64 | >64 | 16 | 32 | 4 | >64 |
| AZI | >64 | >64 | 8 | 8 | 16 | >64 |
| CLR | >64 | >64 | 4 | 8 | 2 | >64 |
| TEL | 8 | 16 | 0.5 | 1 | 0.06 | 0.125 |
| CLN | >64 | >64 | 0.06 | 0.125 | 0.125 | 0.25 |
| Amoxicillin/clavulanate | <0.015 | 0.03 | 0.015 | 0.06 | 0.03 | 0.03 |
| Levofloxacin | 0.5 | 1 | 0.5 | 1 | 0.5 | 1 |
| Moxifloxacin | 0.25 | 0.25 | 0.25 | 0.25 | 0.25 | 0.25 |
| Penicillin G | 0.015 | 0.015 | 0.015 | 0.03 | 0.015 | 0.015 |

Against macrolide-susceptible strains, CEM-101 MICs were 0.008-0.03 µg/ml and those against macrolide-resistant strains (all phenotypes) MICs were 0.015-1 µg/ml. TEL MICs were up to four-fold higher than those of CEM-101. The majority (17/19) of erm(B) strains were TEL-resistant with MICs between 4 and 16 µg/ml while all had low CEM-101 MICs, similar to those of other resistance phenotypes (range 0.03-1 µg/ml). Results of pneumococcal multistep resistance selection studies are presented in the following Table.

| *S. pneumoniae* multistep selection results. | | | | | | | | |
|---|---|---|---|---|---|---|---|---|
| Strain No. Phenotype [R-determinates] Drug | Initial MIC (µg/ml) | Selected Resistance | | Retest MIC after 10 Antibiotic-Strain number Drug free Subcultures | | | | |
| | | MIC | # Pass. | CEM | AZI | CLA | TEL | CLI |
| 1077 Macrolide-S | | | | | | | | |
| CEM-101 | 0.008 | 0.06 | 43 | 0.06 | 0.03 | 0.06 | 0.06a | 0.03 |
| AZI | 0.03 | >64 | 29 | 0.03 | >64 | >64 | 0.125 | 4 |
| CLR | 0.016 | 0.008 | 50 | — | — | — | — | — |
| TEL | 0.004 | 0.25 | 15 | 0.06 | >64 | >64 | 0.25 | 8 |
| CLN | 0.016 | 4 | 49 | 0.06 | >64 | >64 | 0.06 | 8 |

-continued

S. pneumoniae multistep selection results.

| Strain No. Phenotype [R-determinates] Drug | Initial MIC (μg/ml) | Selected Resistance | | Retest MIC after 10 Antibiotic-Strain number Drug free Subcultures | | | | |
|---|---|---|---|---|---|---|---|---|
| | | MIC | # Pass. | CEM | AZI | CLA | TEL | CLI |
| 24 Macrolide-R[erm(B)] | | | | | | | | |
| CEM-101 | 0.004 | 0.06 | 14 | 0.06 | >64 | >64 | 0.125 | >64 |
| AZI | >64 | NT | NT | — | — | — | — | — |
| CLR | >64 | NT | NT | — | — | — | — | — |
| TEL | 0.25 | 32 | 14 | 0.06 | >64 | >64 | 16 | >64 |
| CLN | >64 | NT | NT | — | — | — | — | — |
| 3665 Macrolide-R [mef(A)] | | | | | | | | |
| CEM-101 | 0.03 | 0.5 | 14 | 0.5 | 16 | 4 | 0.25 | 0.03 |
| AZI | 8 | 16 | 50 | — | — | — | — | — |
| CLR | 2 | 16 | 26 | 0.06 | 8 | 8 | 0.06 | 0.03 |
| TEL | 0.125 | 2 | 14 | 0.03 | 4 | 2 | 0.25 | 0.03 |
| CLN | 0.016 | 0.03 | 50 | — | — | — | — | — |
| 1076 Macrolide-R [erm(B)&mef(A)] | | | | | | | | |
| CEM-101 | 1 | 32 | 18 | 32 | >64 | >64 | 32 | >64 |
| AZI | >64 | NT | NT | — | — | — | — | — |
| CLR | >64 | NT | NT | — | — | — | — | — |
| TEL | 0.5 | >64 | 14 | 2 | >64 | >64 | >64 | >64 |
| CLN | 64 | NT | NT | — | — | — | — | — |
| 1635 Macrolide-R [erm(A)] | | | | | | | | |
| CEM-101 | 0.008 | 0.06 | 32 | 0.125 | 4 | 1 | 0.03 | 0.03 |
| AZI | 2 | >64 | 14 | 0.004 | >64 | >64 | 0.004 | 0.03 |
| CLR | 0.5 | >64 | 49 | 0.008 | >64 | >64 | 0.016 | 0.25 |
| TEL | 0.004 | 0.008 | 50 | — | — | — | — | — |
| CLN | 0.06 | >64 | 14 | 0.004 | 4 | 0.5 | 0.008 | >64 |
| 2686 Macrolide-R [L4 mutation] | | | | | | | | |
| CEM-101 | 0.03 | 0.5 | 22 | 1 | >64 | 32 | 0.25 | 0.03 |
| AZI | >64 | NT | NT | — | — | — | — | — |
| CLR | 8 | >64 | 14 | 0.03 | >64 | >64 | 0.06 | 0.03 |
| TEL | 0.06 | 0.5 | 25 | 0.016 | >64 | 16 | 0.5 | 0.03 |
| CLN | 0.03 | 0.125 | 50 | — | — | — | — | — |
| 7127 Macrolide-S [S20N in L4, A105V in L22] | | | | | | | | |
| CEM-101 | 0.008 | 0.125 | 16 | 0.06 | 0.06 | 0.125 | 0.06 | 0.03 |
| AZI | 0.06 | 0.5 | 29 | 0.016 | 1 | 0.5 | 0.016 | 0.06 |
| CLR | 0.03 | 16 | 15 | 0.008 | >64 | 16 | 0.008 | 1 |
| TEL | 0.008 | 0.06 | 38 | 0.008 | 0.06 | 0.06 | 0.03 | 0.03 |
| CLN | 0.03 | 0.25 | 43 | 0.004 | 0.03 | 0.016 | 0.008 | 0.25 |
| 3009 Macrolide-R [23SrRNA mutation] | | | | | | | | |
| CEM-101 | 0.016 | 0.25 | 20 | 0.25 | >64 | >64 | 0.06 | 1 |
| AZI | >64 | NT | NT | — | — | — | — | — |
| CLR | 16 | >64 | 25 | 0.03 | >64 | 64 | 0.06 | 1 |
| TEL | 0.016 | 0.03 | 50 | — | — | — | — | — |
| CLN | 1 | 2 | 50 | — | — | — | — | — | bCross-reactivity denoted in bold.

For pneumococci, parental MICs (μg/ml) were: CEM-101, 0.004-1; AZI, 0.03-8; CLR, 0.016-16; TEL, 0.004-0.5; CLN, 0.016-1. Four strains with AZI, two with CLR, and two with CLN MICs≥64 μg/ml were not tested. CEM-101 MICs increased after 14-43 days in all 8 strains tested. For 7 strains, MICs rose from 0.004-0.03 μg/ml (parents) to 0.06-0.5 μg/ml (resistant clones) in 14-43 days. For the eighth strain, containing erm(B)+mef(A), MICs rose from 1 μg/ml (parent) to 32 μg/ml (resistant clone) in 18 days. This CEM-101 resistant clone was subjected to sequencing analysis, which revealed no alterations in L4, L22 proteins and II and V domain of 23S rRNA compared to parental sequences. AZI had resistant clones after 14-29 days in ⅜ strains with MICs rising from 0.03-2 μg/ml (parents) to 0.5→64 μg/ml (resistant clones). CLR had resistant clones after 14-49 days in ⅝ strains with MICs rising from 0.03-16 μg/ml (parents) to 16→64 μg/ml (resistant clones). TEL had stable resistant clones after 14-38 days in ⅝ tested with MICs rising from 0.004-0.5 μg/ml (parents) to 0.06→64 μg/ml (resistant clones). CLN had resistant clones after 14-43 days in ⅖ strains with MICs rising from 0.03-0.06 μg/ml (parents) to 0.25→64 μg/ml (resistant clones).
Results for *S. pyogenes* are shown in the following Table.

the maximum 50 days. AZI had resistant clones after 5-35 days in ¾ strains tested, with MICs rising from 0.06-4 μg/ml (parents) to 1→64 μg/ml (resistant clones). CLR had resistant clones after 6 days in ¼ strains tested, with MICs rising from

| Strain number Phenotype [Rdeterminates] Antibiotic | Initial MIC (μg/ml) | Selected Resistance | | Retest MIC after 10 Antibioticfree Subcultures | | | | |
|---|---|---|---|---|---|---|---|---|
| | | | | CEM | AZI | CLA | TEL | CLI |
| 2132 Macrolide-S | | | | | | | | |
| CEM-101 | 0.008 | 0.016 | 50 | 0.016 | 1 | 0.25b | 0.03 | 0.03 |
| AZI | 0.06 | 1 | 28 | | | | | |
| CLR | 0.03 | 0.016 | 50 | — | — | — | — | — |
| TEL | 0.008 | 0.03 | 50 | — | — | — | — | — |
| CLN | 0.06 | 0.06 | 50 | — | — | — | — | — |
| 2368 Macrolide-R [erm(B)] | | | | | | | | |
| CEM-101 | 1 | 8 | 18 | 8 | >64 | >64 | >64 | >64 |
| AZI | >64 | NT | NT | — | — | — | — | — |
| CLR | >64 | NT | NT | — | — | — | — | — |
| TEL | 8 | >64 | 6 | 0.5 | >64 | >64 | >64 | >64 |
| CLN | >64 | NT | NT | — | — | — | — | — |
| 2094 Macrolide-R [erm(A)] | | | | | | | | |
| CEM-101 | 0.03 | 0.25 | 43 | 0.25 | 4 | 8 | 0.5 | 0.06 |
| AZI | 4 | >64 | 5 | 0.016 | >64 | 1 | 0.03 | 0.06 |
| CLR | 0.5 | >64 | 6 | 0.016 | >64 | >64 | 0.03 | 0.06 |
| TEL | 0.03 | 0.25 | 22 | 0.03 | >64 | 8 | 0.125 | >64 |
| CLN | 0.06 | >64 | 34 | 0.03 | 16 | 1 | 0.03 | >64 |
| 2011 Macrolide-R [mef(A)] | | | | | | | | |
| CEM-101 | 0.125 | 0.125 | 50 | — | — | — | — | — |
| AZI | 4 | 32 | 35 | 0.06 | 16 | 4 | 0.25 | 0.06 |
| CLR | 4 | 8 | 50 | — | — | — | — | — |
| TEL | 0.5 | 1 | 50 | — | — | — | — | — |
| CLN | 0.06 | 0.06 | 50 | — | — | — | — | — |
| 237 Macrolide-R [L4 mutation] | | | | | | | | |
| CEM-101 | 0.03 | 0.25 | 20 | 0.5 | 4 | 1 | 1 | 0.03 |
| AZI | 4 | 8 | 50 | — | — | — | — | — |
| CLR | 0.25 | 1 | 50 | — | — | — | — | — |
| TEL | 0.06 | 0.125 | 50 | — | — | — | — | — |
| CLN | 0.06 | 0.5 | 43 | 0.03 | 8 | 0.5 | 0.06 | 1 | bCross-reactivity denoted in bold.

Parental MICs (μg/ml) were: CEM-101, 0.008-1; AZI, 0.06-4; CLR, 0.03-4; TEL, 0.008-8; CLN 0.06. One strain with AZI, CLR and CLN MICs>64 μg/ml was not tested. CEM-101 MICs increased after 18-43 days in ⅗ strains, rising from 0.03-1 μg/ml (parents) to 0.25-8 μg/ml (resistant clones). The resistant clone with a CEM-101 MIC of 8 μg/ml was subjected to sequencing analysis, which showed no changes in all genes (L4, L22 and II and V domain of 23S rRNA) tested. CEM-101 MICs for the remaining 2 clones did not go above 0.25 μg/ml when passages were continued for the maximum 50 days. AZI had resistant clones after 5-35 days in ¾ strains tested, with MICs rising from 0.06-4 μg/ml (parents) to 1→64 μg/ml (resistant clones). CLR had resistant clones after 6 days in ¼ strains tested, with MICs rising from 0.5 μg/ml (parent) to >64 μg/ml (resistant clone). TEL had resistant clones after 6-22 days in ⅖ strains tested, with MICs rising from 0.03-8 μg/ml (parents) to 0.25→64 μg/ml (resistant clones). CLN had resistant clones after 34-43 days in ⅔ strains tested with MICs rising from 0.06 μg/ml (parents) to 0.5→64 μg/ml (resistant clones). Results of single step resistance selection studies for pneumococci are presented in the following Table.

| Strain number | Phenotype [R-determinates] | Selecting Drug | 2x MIC | 4xMIC | 8xMIC |
|---|---|---|---|---|---|
| 1077 | Macrolide-S[a] | CEM-101 | $<9.1 \times 10^{-9}$ | $<9.1 \times 10^{-9}$ | $<9.1 \times 10^{-9}$ |
| | | Azithromycin | $7.2 \times 10^{-9}$ | $<1.9 \times 10^{-10}$ | $<1.9 \times 10^{-10}$ |
| | | Clarithromycin | $1.1 \times 10^{-9}$ | $<1.2 \times 10^{-10}$ | $<1.2 \times 10^{-10}$ |
| | | Telithromycin | $1.1 \times 10^{-9}$ | $<5.5 \times 10^{-10}$ | $<5.5 \times 10^{-10}$ |
| | | Clindamycin | $<3.8 \times 10^{-10}$ | $<3.8 \times 10^{-10}$ | $<3.8 \times 10^{-10}$ |

| Strain number | Phenotype [R-determinates.] | Selecting Drug | 2x MIC | 4xMIC | 8xMIC |
|---|---|---|---|---|---|
| 24 | Macrolide-R[a] [erm(B)] | CEM-101 | $1.8 \times 10^{-7}$ | $<5.0 \times 10^{-9}$ | $<5.0 \times 10^{-9}$ |
| | | Azithromycin | NT | NT | NT |
| | | Clarithromycin | NT | NT | NT |
| | | Telithromycin | $1.3 \times 10^{-4}$ | $2.5 \times 10^{-6}$ | $1.7 \times 10^{-6}$ |
| | | Clindamycin | NT | NT | NT |
| 3665 | Macrolide-R [mef(A)] | CEM-101 | $6.8 \times 10^{-7}$ | $1.4 \times 10^{-7}$ | $<4.5 \times 10^{-10}$ |
| | | Azithromycin | NT | NT | NT |
| | | Clarithromycin | $5.0 \times 10^{-7}$ | $<5.0 \times 10^{-10}$ | $<5.0 \times 10^{-10}$ |
| | | Telithromycin | $7.5 \times 10^{-9}$ | $2.5 \times 10^{-9}$ | $<2.5 \times 10^{-10}$ |
| | | Clindamycin | $<2.4 \times 10^{-10}$ | $<2.4 \times 10^{-10}$ | $<2.4 \times 10^{-10}$ |
| 1076 | Macrolide-R [erm(B)&mef(A)] | CEM-101 | $<2.5 \times 10^{-8}$ | $7.5 \times 10^{-9}$ | $2.0 \times 10^{-9}$ |
| | | Azithromycin | NT | NT | NT |
| | | Clarithromycin | NT | NT | NT |
| | | Telithromycin | $6.5 \times 10^{-6}$ | $9.7 \times 10^{-6}$ | $4.8 \times 10^{-6}$ |
| | | Clindamycin | NT | NT | NT |
| 1635 | Macrolide-R [erm(A)] | CEM-101 | $1.6 \times 10^{-8}$ | $<2.0 \times 10^{-10}$ | $<2.0 \times 10^{-10}$ |
| | | Azithromycin | $<2.0 \times 10^{-10}$ | $<2.0 \times 10^{-10}$ | $<2.0 \times 10^{-10}$ |
| | | Clarithromycin | $<3.1 \times 10^{-9}$ | $<3.1 \times 10^{-9}$ | $<3.1 \times 10^{-9}$ |
| | | Telithromycin | $<2.7 \times 10^{-9}$ | $<2.7 \times 10^{-9}$ | $<2.7 \times 10^{-9}$ |
| | | Clindamycin | $7.3 \times 10^{-7}$ | $5.5 \times 10^{-7}$ | $5.6 \times 10^{-7}$ |
| 2686 | Macrolide-R [L4 mutation] | CEM-101 | $<2.5 \times 10^{-9}$ | $<2.5 \times 10^{-9}$ | $<2.5 \times 10^{-9}$ |
| | | Azithromycin | NT | NT | NT |
| | | Clarithromycin | NT | NT | NT |
| | | Telithromycin | $2.2 \times 10^{-5}$ | $2.2 \times 10^{-9}$ | $<1.1 \times 10^{-9}$ |
| | | Clindamycin | $<1.2 \times 10^{-9}$ | $<1.2 \times 10^{-9}$ | $<1.2 \times 10^{-9}$ |
| 7127 | Macrolide-S [S20N in L4, A105V in L22] | CEM-101 | $<2.0 \times 10^{-10}$ | $<2.0 \times 10^{-10}$ | $<2.0 \times 10^{-10}$ |
| | | Azithromycin | $<2.0 \times 10^{-10}$ | $<2.0 \times 10^{-10}$ | $<2.0 \times 10^{-10}$ |
| | | Clarithromycin | $<1.0 \times 10^{-9}$ | $<1.0 \times 10^{-9}$ | $<1.0 \times 10^{-9}$ |
| | | Telithromycin | $<5.0 \times 10^{-9}$ | $<5.0 \times 10^{-9}$ | $<5.0 \times 10^{-9}$ |
| | | Clindamycin | $<2.9 \times 10^{-8}$ | $<2.9 \times 10^{-8}$ | $<2.9 \times 10^{-8}$ |
| 3009 | Macrolide-R [23S rRNA mutation] | CEM-101 | $<5.9 \times 10^{-9}$ | $<5.9 \times 10^{-9}$ | $<5.9 \times 10^{-9}$ |
| | | Azithromycin | NT | NT | NT |
| | | Clarithromycin | NT | NT | NT |
| | | Telithromycin | $3.8 \times 10^{-7}$ | $<1.5 \times 10^{-10}$ | $<1.5 \times 10^{-10}$ |
| | | Clindamycin | $1.7 \times 10^{-4}$ | $7.3 \times 10^{-9}$ | $<1.2 \times 10^{-10}$ |

[a] S = Susceptible; R = Resistant

The same 4 comparators used in multistep selection were tested for their propensity to produce spontaneous mutations. Mutant selection frequencies for CEM-101 ranged from $<2.0 \times 10^{-10}$-$6.8 \times 10^{-7}$ at 2x MIC to $<2.0 \times 10^{-10}$-$9.1 \times 10^{-9}$ at 8x MIC. These comparators had higher frequencies of resistance: TEL, $1.1 \times 10^{-9}$-$1.3 \times 10^{-4}$ at 2x MIC to $<1.5 \times 10^{-10}$-$4.8 \times 10^{-6}$ at 8x MIC; CLN, $<2.4 \times 10^{-10}$-$1.7 \times 10^{-4}$ at 2x MIC to $<1.2 \times 10^{-10}$-$5.6 \times 10^{-7}$ at 8x MIC; and CLR, $<1.0 \times 10^{-9}$-$5.0 \times 10^{-7}$ at 2x MIC to $<1.2 \times 10^{-10}$-$3.1 \times 10^{-9}$ at 8x MIC. A small number, 3 strains, were tested with AZI; mutant selection frequencies were $<2.0 \times 10^{-10}$-$7.2 \times 10^{-9}$ at 2x MIC to $<1.9 \times 10^{-10}$-$<2.0 \times 10^{-10}$ at 8x MIC. Results of single step resistance selection studies for *S. pyogenes* are presented in the following Table.

S. pyogenes single step mutation frequencies

| Strain number | Phenotype [R-determinates.] | Selecting Drug | 2× MIC | 4×MIC | 8×MIC |
|---|---|---|---|---|---|
| 2132 | Macrolide-S[a] | CEM-101 | $<1.0 \times 10^{-10}$ | $<1.0 \times 10^{-10}$ | $<1.0 \times 10^{-10}$ |
| | | Azithromycin | $<1.0 \times 10^{-10}$ | $<1.0 \times 10^{-10}$ | $<1.0 \times 10^{-10}$ |
| | | Clarithromycin | $<1.0 \times 10^{-10}$ | $<1.0 \times 10^{-10}$ | $<1.0 \times 10^{-10}$ |
| | | Telithromycin | $<8.3 \times 10^{-11}$ | $<8.3 \times 10^{-11}$ | $<8.3 \times 10^{-11}$ |
| | | Clindamycin | $<7.7 \times 10^{-11}$ | $<7.7 \times 10^{-11}$ | $<7.7 \times 10^{-11}$ |
| 2368 | Macrolide-R[a] [erm(B)] | CEM-101 | $<5.9 \times 10^{-11}$ | $<5.9 \times 10^{-11}$ | $<5.9 \times 10^{-11}$ |
| | | Azithromycin | NT | NT | NT |
| | | Clarithromycin | NT | NT | NT |
| | | Telithromycin | NT | NT | NT |
| | | Clindamycin | NT | NT | NT |
| 2094 | Macrolide-R [erm(A)] | CEM-101 | $5.3 \times 10^{-8}$ | $2.1 \times 10^{-9}$ | $5.3 \times 10^{-10}$ |
| | | Azithromycin | NT | NT | NT |
| | | Clarithromycin | $1.7 \times 10^{-7}$ | $1.0 \times 10^{-7}$ | $5.0 \times 10^{-9}$ |
| | | Telithromycin | $7.7 \times 10^{-8}$ | $<1.5 \times 10^{-10}$ | $<1.5 \times 10^{-10}$ |
| | | Clindamycin | $2.1 \times 10^{-7}$ | $1.3 \times 10^{-7}$ | $1.1 \times 10^{-7}$ |
| 2011 | Macrolide-R [mef(A)] | CEM-101 | $3.9 \times 10^{-8}$ | $<1.1 \times 10^{-10}$ | $<1.1 \times 10^{-10}$ |
| | | Azithromycin | NT | NT | NT |
| | | Clarithromycin | NT | NT | NT |
| | | Telithromycin | $3.8 \times 10^{-8}$ | $<6.3 \times 10^{-10}$ | $<6.3 \times 10^{-10}$ |
| | | Clindamycin | $<1.0 \times 10^{-10}$ | $<1.0 \times 10^{-10}$ | $<1.0 \times 10^{-10}$ |
| 237 | Macrolide-R [L4 mutation] | CEM-101 | $<1.3 \times 10^{-10}$ | $<1.3 \times 10^{-10}$ | $<1.3 \times 10^{-10}$ |
| | | Azithromycin | NT | NT | NT |
| | | Clarithromycin | $<3.3 \times 10^{-10}$ | $<3.3 \times 10^{-10}$ | $<3.3 \times 10^{-10}$ |
| | | Telithromycin | $<2.0 \times 10^{-10}$ | $<2.0 \times 10^{-10}$ | $<2.0 \times 10^{-10}$ |
| | | Clindamycin | $<1.0 \times 10^{-10}$ | $<1.0 \times 10^{-10}$ | $<1.0 \times 10^{-10}$ |

[a]S = Susceptible; R = Resistant

As with the pneumococci, the 4 comparators used in multistep selection were tested for their propensity to produce spontaneous mutations. Mutant selection frequencies for CEM-101 ranged from <5.9×10−11-5.3×10−8 at 2× MIC to <5.9×10−11-<5.3×10−10 at 8× MIC. The following comparators had higher frequencies of resistance than CEM-101: CLN, <7.7×10−11-2.1×10−7 at 2× MIC to <7.7×10−11-1.1×10−7 at 8× MIC; and CLR, <1.0×10−10-1.7×10−7 at 2× MIC to <1.0×10−10-5.0×10−9 at 8× MIC. TEL frequencies were similar to CEM-101: <8.3×10−11-7.7×10−8 at 2× MIC to <8.3×10−11-<6.3×10−10 at 8× MIC. The mutation frequency for the one macrolide-sensitive strain tested with AZI was $<1.0 \times 10^{-10}$ at 2× and 8× MIC.

The compounds described herein demonstrate enhanced potency compared to TEL, with activity against TEL-intermediate and TEL resistant organisms. The compounds described herein show significantly greater potency against phagocytized S. aureus when compared to TEL, AZI, and CLR. The compounds described herein are also about 50-fold and 100-fold more potent than AZI against phagocytized L. monocytogenes and L. pneumophila. The compounds described herein exhibit the widest spectrum of activity against respiratory tract pathogens, including multi drug-resistant pneumococcus type 19A, compared to AZI, CLR, erythromycin, TEL, CLN, and quinupristin/dalfopristin. The compounds described herein are also potent against C. trachomatis, C. pneumoniae, human mycoplasmas and ureaplasmas, and the MICs also point to clinical utility against most enterococci, gonococci, and Gram positive anaerobes. The compounds described herein are active against common organisms that cause gastroenteritis, such as Campylobacter jejuni, Salmonella and Shigella, and is also active against Helicobacter pylori. The compounds described herein are shown to be more bactericidal against several gram-positive species than TEL, with post-antibiotic effects of 2.3-6.1 and 3.7-5.3 against gram-positive and -negative strains, respectively. The compounds described herein demonstrate significant in vivo activity in a variety of murine infection models.

Preliminary multistep studies show that the compounds described herein have no or only low variation in MICs in one strain each of S. aureus, Enterococcus faecalis, and 2 S. pneumoniae; low rates of spontaneous mutants are found in single step experiments.

The compounds described herein have MICs that are generally at least 1 or 2 dilutions lower than those of TEL against all resistance phenotypes of S. pneumoniae and S. pyogenes tested, including drug-resistant pneumococcus type 19A and erm(B) positive S. pyogenes. CEM-101 yielded clones with higher MICs in all 8 pneumococcal strains, but 7 of the 8 strains have clones with CEM-101 MICs≤0.5 μg/ml and in only 1 erm(B)+mef(A) strain with a parental MIC of 1 μg/ml was a resistant clone found with an MIC of 32 μg/ml. In 2 of the 3 resistant S. pyogenes CEM-101 clones [parents erm(A), L4] MICs were 0.25 μg/ml and only in the 1 strain with erm(B) did CEM-101 MICs rise from 1 to 8 μg/ml. Single step studies also showed low yields of spontaneous mutations compared to other agents tested.

Based on pharmacokinetics reported from Phase 1 clinical trials recommendations for tentative CEM-101 susceptibility breakpoints have been set at ≤1 μg/ml as susceptible and ≥4 μg/ml as resistant against streptococci.

Example

Staphylococci, β-Haemolytic and Viridans Group Streptococci. A collection of 2006-2007 clinical isolates were S tested by CLSI methods (M7-A7) with associated interpretive criteria (M100-S18) and supplements (2-5% LHB) for streptococcal tests. CEM-101, TEL (TEL) and 10 comparators were used versus 201 S. aureus (75 WT-MRSA, 75 WT-MSSA, 30 CA-MRSA, 17 VISA or hVISA, 7 VRSA), 100 coagulase-negative staphylococci (CoNS; 10 species), 100 β-haemolytic (BHS; 30 group A, 31 group B, 14 group C, 9 group F, 16 group G) and 51 viridans group streptococci (VGS; 5 species), see Table.

MSSA strains were slightly more CEM-101-S (MIC50, 0.06 μg/ml) that MRSA or CA-MRSA strains (MIC50, 0.12

µg/ml). VISA, hVISA and VRSA were generally more refractory to CEM-101 and TEL. CEM-101 was 2-fold more potent than TEL against all staphylococci. Streptococci were very S to CEM-101 (MIC90, 0.03-0.06 µg/ml) and TEL was 4-fold less active with non-S isolates of BHS observed. ERY-R staphylococci remained CEM-101-S except for TEL- and CLN (CC)-R isolates, but all BHS and VGS were S to CEM-101.

| Organisms (no.) | CEM-101 MIC (µg/ml) | | | TEL MIC (µg/ml) | | |
|---|---|---|---|---|---|---|
| | 50% | 90% | Range | 50% | 90% | Range |
| MSSA (75) | 0.06 | 0.12 | 0.03->16 | 0.12 | 0.25 | 0.06->16 |
| MRSA (75) | 0.12 | >16 | 0.03->16 | 0.25 | >16 | 0.06->16 |
| CA-MRSA (30) | 0.12 | 0.12 | 0.06-0.12 | 0.25 | 0.25 | 0.12-0.5 |
| VISA, hVISA (14) | >16 | >16 | 0.06->16 | >16 | >16 | 0.25->16 |
| VRSA (7) | >16 | — | 0.12->16 | >16 | — | 0.12->16 |
| CoNS (100) | 0.06 | >16 | 0.03->16 | 0.12 | >16 | 0.03->16 |
| BHS (100) | 0.015 | 0.03 | ≤0.008-0.12 | 0.03 | 0.12 | ≤0.008-2 |
| VGS (51) | ≤0.008 | 0.06 | ≤0.008-0.12 | 0.015 | 0.25 | ≤0.008-0.5 |

CEM-101 was potent against all staphylococci (MIC50, 0.06 µg/ml), except CC-R strains; and inhibited all streptococci at ≤0.12 µg/ml. The activity was greater than TEL by 2- to 4-fold.

What is claimed is:

1. A method for inhibiting the growth of bacteria in a host animal, having the bacteria that is resistant to one or more penicillins, cephalosporins, quinolones, macrolides, vancomycin, or a combination thereof, the method comprising the step of administering to the host animal an effective amount of a compound of the formula

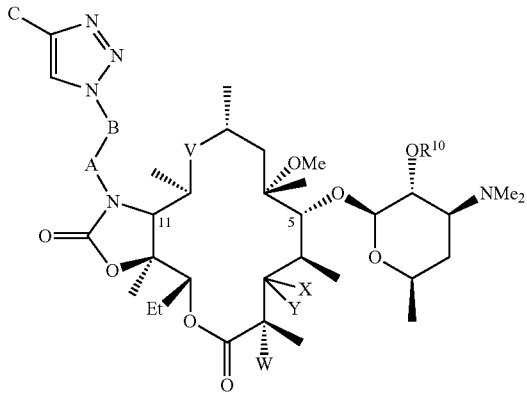

or pharmaceutically acceptable salt thereof, wherein:
$R^{10}$ is hydrogen or acyl;
X is H; and Y is $OR^7$; where $R^7$ is monosaccharide, disaccharide, alkyl, arylalkyl, or heteroarylalkyl, each of which is optionally substituted, or acyl or $C(O)NR^8R^9$; where $R^8$ and $R^9$ are each independently selected from the group consisting of hydrogen, hydroxy, alkyl, heteroalkyl, alkoxy, aryl, arylalkyl, heteroaryl, and heteroarylalkyl, each of which is optionally substituted, and dimethylaminoalkyl, acyl, sulfonyl, ureido, and carbamoyl; or X and Y are taken together with the attached carbon to form carbonyl;
V is C(O), C(=NR$^{11}$), CH(NR$^{12}$,R$^{13}$), or N(R$^{14}$)CH$_2$; where N(R$^{14}$) is attached to the C-10 carbon; where R$^{11}$ is hydroxy or alkoxy; R$^{12}$ and R$^{13}$ are each independently selected from the group consisting of hydrogen, hydroxy, alkyl, alkoxy, heteroalkyl, aryl, arylalkyl, heteroaryl, and heteroarylalkyl, each of which is optionally substituted, and dimethylaminoalkyl, acyl, sulfonyl, ureido, and carbamoyl; $R^{14}$ is hydrogen, hydroxy, alkyl, alkoxy, heteroalkyl, aryl, arylalkyl, heteroaryl, or heteroarylalkyl, each of which is optionally substituted, or dimethylaminoalkyl, acyl, sulfonyl, ureido, or carbamoyl;

W is H, F, Cl, Br, I, or OH;
A is CH$_2$, C(O), C(O)O, C(O)NH, S(O)$_2$, S(O)$_2$NH, or C(O)NHS(O)$_2$;
B is (CH$_2$)$_n$ where n is an integer from 0 to 10; or an unsaturated carbon chain of 2 to 10 carbons; and
C is hydrogen, hydroxy, alkyl, alkoxy, heteroalkyl, aryl, arylalkyl, heteroaryl, or heteroarylalkyl, each of which is optionally substituted, or acyl, acyloxy, sulfonyl, ureido, or carbamoyl, where C is other than 2-pyridinyl;
or an antibacterial composition thereof further comprising one or more pharmaceutically acceptable carriers, excipients, or diluents therefor, or a combination thereof.

2. A method for killing one or more bacteria in a host animal, having at least one of the bacteria that is resistant to one or more penicillins, cephalosporins, quinolones, macrolides, vancomycin, or a combination thereof, the method comprising the step of administering to the host animal an effective amount of the compound recited in claim 1, or an antibacterial composition thereof further comprising one or more pharmaceutically acceptable carriers, excipients, or diluents therefor, or a combination thereof.

3. The method of claim 1 wherein $R^{10}$ is hydrogen.
4. The method of claim 1 wherein C is aryl or heteroaryl, each of which is optionally substituted.
5. The method of claim 1 wherein C is 3-aminophenyl or 3-pyridinyl.
6. The method of claim 1 wherein V is C(O).
7. The method of claim 1 wherein W is H or F.
8. The method of claim 1 wherein W is F.
9. The method of claim 1 wherein X and Y are taken together with the attached carbon to form carbonyl.
10. The method of claim 1 wherein V is C(O); X and Y are taken together with the attached carbon to form carbonyl; and W is F.
11. The method of claim 1 wherein A is CH$_2$, B is (CH$_2$)$_n$, and n is an integer from 2-4.
12. The method of claim 11 wherein C is 3-aminophenyl.
13. The method of claim 12 wherein V is C(O).
14. The method of claim 13 wherein X and Y are taken together with the attached carbon to form carbonyl.
15. The method of claim 14 wherein W is F.
16. The method of claim 15 wherein n is 3.
17. The method of claim 16 wherein $R^{10}$ is hydrogen.

18. The method of claim 1 wherein the organism is a MRSA, VRSA, Macrolide-Lincosamide-Streptogramin B (MLS$_B$) resistant organism, MDR pneumococcus, *S. pneumoniae* serotype 19A, erythromycin resistant *S. pyogenes*, erythromycin resistant staphylococci, or *S. pneumoniae* with at least one erm(B), erm(A), mef(A), mef(E), mef(I), erm (B)+mef(A), L4, or 23S ribosomal protein mutation, or a combination thereof.

19. The method of claim 1 wherein the organism is a *S. pneumoniae* with at least one erm(B), erm(A), mef(A), mef (E), mef(I), erm(B)+mef(A), L4, or 23S ribosomal protein mutation, or a combination thereof.

20. The method of claim 1 wherein the organism is macrolide or ketolide resistant.

21. The method of claim 1 wherein the organism is a *Neisseria gonorrhoeae, Mycoplasma, Ureaplasma, Legionella pneumophila, Moraxella catarrhalis, Enterococcus faecalis*, or *Chlamydia*, or a combination thereof.

22. The method of claim 1 wherein the therapeutically effective amount is bactericidal to at least one of *S. aureus, S. epidermidis, S. pneumoniae, S. pyogenes*, and *S. mitis*.

23. The method of claim 1 wherein the MBC/MIC ratio is about 16 or less.

24. The method of claim 1 wherein C is substituted aryl.

25. The method of claim 1 wherein the compound recited in claim 1 is of the formula 26. The method of claim 1 wherein the compound recited in claim 1 is of the formula

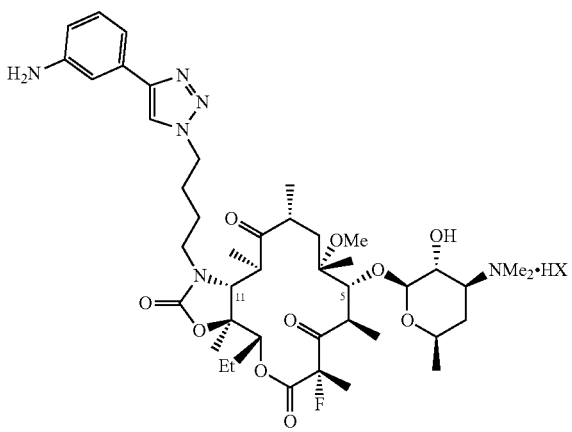

where HX is a pharmaceutically acceptable salt forming acid.

27. The method of claim 26 wherein HX is selected from the group consisting of hydrochloric acid, tartaric acid, and combinations thereof.

28. The method of claim 17 wherein the host animal is a human.

29. The method of claim 17 wherein the bacteria is resistant to one or more penicillins, quinolones, tetracyclines, clindamycin, trimethoprim, sulfamethoxazole, or a combination thereof.

30. The method of claim 17 wherein the bacteria is resistant to one or more macrolides selected from the group consisting of clarithromycin, azithromycin, and telithromycin.

* * * * *